US012742004B2

(12) United States Patent
Wu et al.

(10) Patent No.: US 12,742,004 B2
(45) **Date of Patent: *Sep. 22, 2026**

(54) PHARMACEUTICAL COMPOSITION CONTAINING ANTIBODY AGAINST IL-5 AND USE THEREOF

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Tingting Wu, Shanghai (CN); Hao Li, Shanghai (CN); Xun Liu, Shanghai (CN); Weikang Tao, Shanghai (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 1394 days.

This patent is subject to a terminal disclaimer.

(21) Appl. No.: 17/598,610

(22) PCT Filed: Mar. 27, 2020

(86) PCT No.: PCT/CN2020/081701

§ 371 (c)(1),
(2) Date: Sep. 27, 2021

(87) PCT Pub. No.: WO2020/200099

PCT Pub. Date: Oct. 8, 2020

(65) Prior Publication Data

US 2022/0144937 A1 May 12, 2022

(30) Foreign Application Priority Data

Mar. 29, 2019 (CN) ......................... 201910249953.4

(51) Int. Cl.
*C07K 16/24* (2006.01)
*A61K 39/00* (2006.01)
*A61P 11/06* (2006.01)

(52) U.S. Cl.
CPC ............ *C07K 16/244* (2013.01); *A61P 11/06* (2018.01); *A61K 2039/505* (2013.01); *C07K 2317/24* (2013.01); *C07K 2317/76* (2013.01); *C07K 2317/92* (2013.01)

(58) Field of Classification Search
CPC ........................ C07K 16/244; A61K 2039/505
See application file for complete search history.

(56) References Cited

U.S. PATENT DOCUMENTS

| | | | | |
|---|---|---|---|---|
| 5,096,704 A | | 3/1992 | Coffman et al. | |
| 9,505,826 B2 | | 11/2016 | Wilson et al. | |
| 11,365,247 B2 | * | 6/2022 | Ying | A61P 11/06 |
| 12,258,394 B2 | * | 3/2025 | Ying | C07K 16/244 |
| 12,258,405 B2 | * | 3/2025 | Ying | A61P 35/00 |

FOREIGN PATENT DOCUMENTS

| | | | | | |
|---|---|---|---|---|---|
| CN | 1175263 A | | 3/1998 | |
| WO | 1995014040 A1 | | 5/1995 | |
| WO | 1995035375 A1 | | 12/1995 | |
| WO | 2012138958 A1 | | 10/2012 | |
| WO | 2014141149 A1 | | 9/2014 | |
| WO | WO-2015061584 A1 | * | 4/2015 | A61K 38/00 |
| WO | 2015095539 A1 | | 6/2015 | |
| WO | WO-2015173782 A1 | * | 11/2015 | A61K 39/395 |
| WO | 2016040007 A1 | | 3/2016 | |
| WO | 2017033121 A1 | | 3/2017 | |
| WO | 2018119016 A1 | | 6/2018 | |
| WO | WO-2018204368 A1 | * | 11/2018 | A61K 39/3955 |
| WO | 2018/226339 A1 | | 12/2018 | |
| WO | 2019062831 A1 | | 4/2019 | |
| WO | WO-2020114478 A1 | * | 6/2020 | A61P 1/16 |

OTHER PUBLICATIONS

Kiyoshi Takatsu et al., Interleukin-5 and Its Receptor System: Implications in the Immune System and Inflammation, Advances in Immunology (1998), vol. 57, pp. 145-190, Academic Press, Inc., Tokyo, Japan (46 pages).
Emma D. Deeks et al., Reslizumab in Eosinophilic Asthma: A Review, ADIS Drug Evaluation, Drugs (2017), vol. 77, pp. 777-784, Springer International Publishishing Switzerland (8 pages).
Vivian C. Agumadu et al., A Review of Three New Anti-interleukin-5 Monoclonal Antibody Therapies for Severe Asthma, Cureus 10(8): e3216. (2018), pp. 1-7 (7 pages).
Mao Li-Chao et al., Research Progress of a New Agent-Mepolizumab, Practical Pharmacy and Clinical Remedies (2016), vol. 19, No. 10, pp. 1306-1309, China (4 pages).
Hector G. Ortega, M.D., Sc.D. et al., Mepolizumab Treatment in Patients with Severe Eosinophilic Asthma, The New England Journal of Medicine, Sep. 25, 2014, vol. 371, pp. 1198-1207, DOI: 10.1056/NEJMoa1403290 (10 pages).
Min Sung Choy MS et al., Mepolizumab (Nucala) for Severe Eosinophilic Asthma, Pharmacy and Therapeutics Oct. 2016, vol. 41, No. 10, pp. 619-622, PMID: 27757000; PMCID: PMC5046999 (4 pages).

* cited by examiner

*Primary Examiner* — Gary B Nickol
(74) *Attorney, Agent, or Firm* — Morgan, Lewis & Bockius LLP

(57) ABSTRACT

Disclosed in the present application are a pharmaceutical composition containing an antibody against IL-5 and use thereof. In particular, disclosed in the present application is a pharmaceutical composition, which contains an IL-5 antibody or an antigen binding fragment thereof in a buffer solution. In addition, the pharmaceutical composition further contains a saccharide and a nonionic surfactant.

20 Claims, 5 Drawing Sheets

Specification includes a Sequence Listing.

PHARMACEUTICAL COMPOSITION CONTAINING ANTIBODY AGAINST IL-5 AND USE THEREOF

CROSS-REFERENCE TO RELATED APPLICATIONS

The present application is the national stage of International Patent Application No. PCT/CN2020/081701, filed on Mar. 27, 2020, which claims the benefit of and priority to Chinese Application No. CN201910249953.4, filed on Mar. 29, 2019, both of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 29, 2019, is named "702030CPUS_126268-5023-US_Sequence_Listing.TXT" and is 98 kilobytes in size.

FIELD OF THE INVENTION

The present disclosure belongs to the field of pharmaceutical formulation, and in particular relates to a pharmaceutical composition comprising an anti-IL-5 antibody or an antigen-binding fragment thereof, and the use of the same as a diagnostic and therapeutic agent for IL-5 related disease (s).

BACKGROUND OF THE INVENTION

The statements herein only provide background information related to the present disclosure, and do not necessarily constitute the prior art.

Interleukin-5 (IL-5) is one of the important members of interleukin family, also known as T cell replacing factor (TRF), B cell growth factor-II (BCGF-II), IgA-enhancing factor (IgA-EF), or eosinophil differentiation factor (EDF) which is a homo-dimeric glycoprotein secreted mainly by helper T cells 2 (Th2). Human IL-5 is composed of 134 amino acid residues, including a signal peptide composed of 22 amino acids and two glycosylation sites. The active IL-5 is in a form of oligo-dimer, wherein two peptide chains in antiparallel configuration are linked by disulfide bond(s); whereas the IL-5 monomer does not have biological activity (Adv Immunol. 1994; 57:145-90).

Eosinophil (EOS) is related to a variety of inflammatory diseases of the lungs, including allergic diseases related to allergic reactions. Asthma is a chronic respiratory inflammatory disease. There are about 300 million patients worldwide with an incidence rate of 10%. The pathogenesis of asthma is related to a variety of cytokines. IL-5 and the receptor IL-5R play an important role in the pathogenesis of asthma. At present, the most effective way to treat asthma is to administer sterols by nasal or oral route, so as to inhibit the expression of several key mediators (including IL-5) involving in asthma and thereby reduce lung inflammation. However, long-term application of steroid agents has many side effects. Therefore, it is necessary to find novel pharmaceutical target for the treatment of asthma. Studies have shown that the administration of anti-IL-5 antibody inhibits the binding of IL-5 to its receptor; significantly reduces the accumulation of eosinophils in lung, and reduces the level of eosinophils in blood, tissues and sputum; reduces the inflammatory response mediated by eosinophils; improves lung function; and have a favorable effect on severe eosinophilic asthma and recurrent asthma (Drugs. 2017 May; 77 (7): 777-784).

Antibody agents have large molecular weight and complex structures. In the process of production, transportation and storage, antibodies often encounter problems due to denaturation, aggregation, contamination and formation of particles. In order to keep the antibody effective, the biological activity of antibody must be maintained during production, purification, transportation and storage. At present, new technologies for production and purification have been developed to produce large number of highly purified monoclonal antibodies. However, how to stabilize these antibodies during transportation and storage and to provide antibodies in dosage forms suitable for administration has been always a challenge.

For anti-IL-5 antibodies, only Mepolizumab from GSK and Reslizumab from Teva Pharma are currently approved for marketing. Related patents involve WO2018119016, WO2017033121, WO2014141149, WO2016040007, WO2015095539, WO2012138958 and WO9535375 etc.

SUMMARY OF THE INVENTION

The present disclosure provides a pharmaceutical composition which comprises an IL-5 antibody or an antigen-binding fragment thereof, a buffer and a surfactant, wherein the buffer is any one selected from the group consisting of acetic acid-sodium acetate, succinic acid-sodium succinate, histidine-hydrochloride and citric acid-sodium citrate buffer, preferably acetic acid-sodium acetate or succinic acid-sodium succinate buffer; wherein, the anti-IL-5 antibody or the antigen-binding fragment thereof comprises a heavy chain variable region and a light chain variable region, wherein:

(i) the heavy chain variable region comprises HCDR1, HCDR2 and HCDR3 as shown in amino acid sequence SEQ ID NOs: 16, 17 and 18, respectively, and the light chain variable region comprises LCDR1, LCDR2 and LCDR3 as shown in amino acid sequence SEQ ID NOs: 19, 20 and 21, respectively;

(ii) the heavy chain variable region comprises HCDR1, HCDR2 and HCDR3 as shown in amino acid sequence SEQ ID NOs: 22, 23 and 24, respectively, and the light chain variable region comprises LCDR1, LCDR2 and LCDR3 as shown in amino acid sequence SEQ ID NOs: 25, 26 and 27, respectively;

(iii) the heavy chain variable region comprises HCDR1, HCDR2 and HCDR3 as shown in amino acid sequence SEQ ID NOs: 28, 29 and 30, respectively, and the light chain variable region comprises LCDR1, LCDR2 and LCDR3 as shown in amino acid sequence SEQ ID NOs: 31, 32 and 33, respectively;

(iv) the heavy chain variable region comprises HCDR1, HCDR2 and HCDR3 as shown in amino acid sequence SEQ ID NOs: 34, 35 and 36, respectively, and the light chain variable region comprises LCDR1, LCDR2 and LCDR3 as shown in amino acid sequence SEQ ID NOs: 37, 38 and 39, respectively;

(v) the heavy chain variable region comprises HCDR1, HCDR2 and HCDR3 as shown in amino acid sequence SEQ ID NOs: 40, 41 and 42, respectively, and the light chain variable region comprises LCDR1, LCDR2 and LCDR3 as shown in amino acid sequence SEQ ID NOs: 43, 44 and 45, respectively; or (vi) the heavy chain variable region comprises HCDR1, HCDR2 and HCDR3 as shown in amino acid sequence SEQ ID NOs: 34, 82 and 36, respectively, and the light chain variable region comprises LCDR1, LCDR2 and LCDR3 as shown in amino acid sequence SEQ ID NOs: 37, 38 and 39, respectively.

In alternative embodiments, the pH of the buffer in the pharmaceutical composition is about 5.0 to about 6.5, preferably about 5.5 to about 6.5, preferably about 6.0 to about 6.5, preferably about 5.0 to about 6.0, preferably about 5.5 to about 6.0, preferably about 5.0 to about 5.5, preferably about 5.0 to about 5.8, preferably about 5.2 to about 5.8; non-limiting examples of the pH of the buffer comprise about 5.0, about 5.1, about 5.2, about 5.3, about 5.4, about 5.5, about 5.6, about 5.7, about 5.8, about 5.9, about 6.0, about 6.5, and most preferably about 5.5.

In alternative embodiments, the concentration of the buffer in the pharmaceutical composition is about 10 mM to about 40 mM, about 10 mM to about 30 mM, preferably about 15 mM to about 30 mM, preferably about 20 mM to about 30 mM, preferably about 25 mM to about 30 mM, preferably about 10 mM to about 25 mM, preferably about 15 mM to about 25 mM, preferably about 20 mM to about 25 mM, preferably about 10 mM to about 15 mM; non-limiting examples of the concentration of the buffer involve about 10 mM, about 12 mM, about 14 mM, about 16 mM, about 18 mM, about 20 mM, about 22 mM, about 24 mM, about 26 mM, about 28 mM, about 30 mM, about 32 mM, about 34 mM, and most preferably about 30 mM.

In alternative embodiments, the concentration of the anti-IL-5 antibody or the antigen-binding fragment thereof in the pharmaceutical composition is about 1 mg/ml to about 120 mg/ml, preferably about 1 mg/ml to about 100 mg/ml, preferably about 10 mg/ml to about 120 mg/ml, preferably about 20 mg/ml to about 120 mg/ml, preferably about 30 mg/ml to about 120 mg/ml, preferably about 40 mg/ml to about 120 mg/ml, preferably about 50 mg/ml to about 120 mg/ml, preferably about 60 mg/ml to about 120 mg/ml, preferably about 70 mg/ml to about 120 mg/ml, preferably about 80 mg/ml to about 120 mg/ml, preferably about 90 mg/ml to about 120 mg/ml, preferably about 100 mg/ml to about 120 mg/ml, preferably about 110 mg/ml to about 120 mg/ml, preferably about 20 mg/ml to about 100 mg/ml, preferably about 30 mg/ml to about 100 mg/ml, preferably about 40 mg/ml to about 100 mg/ml, preferably about 50 mg/ml to about 100 mg/ml, preferably about 60 mg/ml to about 100 mg/ml, preferably about 70 mg/ml to about 100 mg/ml, preferably about 80 mg/ml to about 100 mg/ml, preferably about 90 mg/ml to about 100 mg/ml; as non-limiting examples, the concentration of the anti-IL-5 antibody or the antigen-binding fragment thereof is about 80 mg/ml, about 85 mg/ml, about 90 mg/ml, about 91 mg/ml, about 92 mg/ml, about 93 mg/ml, about 94 mg/ml, about 95 mg/ml, about 96 mg/ml, about 97 mg/ml, about 98 mg/ml, about 99 mg/ml, about 100 mg/ml, about 101 mg/ml, about 102 mg/ml, about 103 mg/ml, about 104 mg/ml, about 105 mg/ml, about 106 mg/ml, about 107 mg/ml, about 108 mg/ml, about 109 mg/ml, about 110 mg/ml, about 115 mg/ml, about 120 mg/ml, and most preferably about 100 mg/ml.

In alternative embodiments, the surfactant comprised in the pharmaceutical composition can be selected from the group consisting of polysorbate 20, polysorbate 80, polyhydroxyalkylene, Triton, sodium dodecyl sulfonate, sodium lauryl sulfonate, sodium octyl glycoside, lauryl-sulphobetaine, myristyl-sulphobetaine, linoleyl-sulphobetaine, stearyl-sulphobetaine, lauryl-sarcosine, myristyl-sarcosine, linoleyl-sarcosine, stearyl-sarcosine, linoleyl-betaine, myristyl-betaine, cetyl-betaine, lauramidopropyl-betaine, cocamidopropyl-betaine, linoleamidopropyl-betaine, myristamidopropyl-betaine, palmitamidopropyl-betaine, isostearamidopropyl-betaine, myristamidopropyl-dimethylamine, palmamidopropyl-dimethylamine, isostearamidopropyl-dimethylamine, sodium methylcocoyl, sodium methyl-oleoyl taurate, polyethylene glycol, polypropylene glycol, copolymers of ethylene and propylene glycol, etc. The preferred surfactant is polysorbate 80 or polysorbate 20, and more preferably polysorbate 80.

In alternative embodiments, the concentration of polysorbate 80 in the pharmaceutical composition is about 0.05 mg/ml to about 0.6 mg/ml, preferably about 0.1 mg/ml to about 0.6 mg/ml, preferably about 0.2 mg/ml to about 0.6 mg/ml, preferably about 0.3 mg/ml to about 0.6 mg/ml, preferably about 0.4 mg/ml to about 0.6 mg/ml, preferably about 0.5 mg/ml to about 0.6 mg/ml, preferably about 0.2 mg/ml to about 0.5 mg/ml, preferably about 0.3 mg/ml to about 0.5 mg/ml, preferably about 0.4 mg/ml to about 0.5 mg/ml, preferably about 0.3 mg/ml to about 0.4 mg/ml, as non-limiting examples, the concentration of the surfactant in the pharmaceutical composition is about 0.2 mg/ml, about 0.3 mg/ml, about 0.4 mg/ml, about 0.45 mg/ml, about 0.5 mg/ml, about 0.55 mg/ml, about 0.6 mg/ml, and most preferably about 0.4 mg/ml.

Further, in alternative embodiments, the pharmaceutical composition further comprises excipient(s), wherein the excipient is selected from stabilizers.

In alternative embodiments, wherein the stabilizer is selected from saccharide or amino acid; wherein the saccharide can be selected from the group consisting of sucrose, trehalose, mannitol and sorbitol, preferably sucrose. The amino acid is selected from the group consisting of glycine, methionine and proline.

In alternative embodiments, the concentration of the saccharide is about 50 mg/ml to about 80 mg/ml, preferably about 60 mg/ml to about 80 mg/ml, preferably about 70 mg/ml to about 80 mg/ml, preferably about 75 mg/ml to about 80 mg/ml, preferably about 70 mg/ml to about 75 mg/ml; as non-limiting examples, the concentration of the stabilizer in the pharmaceutical composition involves about 70 mg/ml, about 71 mg/ml, about 72 mg/ml, about 73 mg/ml, about 74 mg/ml, about 75 mg/ml, about 76 mg/ml, about 77 mg/ml, about 78 mg/ml, about 79 mg/ml, about 80 mg/ml, and more preferably about 72 mg/ml.

In alternative embodiments, the concentration of the amino acid is about 8 mg/ml.

In alternative embodiments, the pharmaceutical composition comprises: (a) about 1 mg/ml to about 120 mg/ml the anti-IL-5 antibody or the antigen-binding fragment thereof; (b) about 10 mM to about 30 mM acetic acid-sodium acetate buffer, pH is about 5.0 to 6.5; and (c) about 0.1 mg/ml to about 0.6 mg/ml polysorbate 80.

In alternative embodiments, the pharmaceutical composition comprises: (a) about 80 mg/ml to about 100 mg/ml the anti-IL-5 antibody or the antigen-binding fragment thereof; (b) about 10 mM to about 30 mM acetic acid-sodium acetate buffer, pH is about 5.0 to about 6.0; and (c) about 0.1 mg/ml to about 0.4 mg/ml polysorbate 80.

In alternative embodiments, the pharmaceutical composition comprises: (d) about 80 mg/ml to about 120 mg/ml the IL-5 antibody or the antigen-binding fragment thereof; (e) about 10 mM to about 30 mM acetic acid-sodium acetate buffer, pH is about 5.0 to about 5.8; (f) about 0.2 mg/ml to about 0.6 mg/ml polysorbate 80; and (g) about 70 mg/ml to about 75 mg/ml sucrose; preferably, the pharmaceutical composition preferably comprises: (h) about 100 mg/ml the IL-5 antibody or the antigen-binding fragment thereof, (i)

about 30 mM acetic acid-sodium acetate buffer, pH is about 5.5, (j) about 0.4 mg/ml polysorbate 80 and (k) about 72 mg/ml of sucrose.

In some preferred embodiments, the anti-IL-5 antibody or the antigen-binding fragment thereof in the pharmaceutical composition of the present disclosure is a murine antibody, a chimeric antibody or a humanized antibody.

In alternative embodiments, the humanized anti-IL-5 antibody in the pharmaceutical composition comprises a heavy chain variable region as shown in SEQ ID NO: 49, 57, 63, 69 or 75 or variant thereof; the variant comprises 1 to 10 amino acid back-mutations in the heavy chain variable region sequence as shown in SEQ ID NO: 49, 57, 63, 69 or 75, respectively.

In alternative embodiments, the variant is a variant as shown in any one selected from the group consisting of:

(i) a variant, comprising one or more amino acid back-mutations selected from the group consisting of S49T, V93T and K98S in the heavy chain variable region as shown in SEQ ID NO: 49;

(ii) a variant, comprising one or more amino acid back-mutations selected from the group consisting of S49T, V93T and K98T in the heavy chain variable region as shown in SEQ ID NO: 57;

(iii) a variant, comprising one or more amino acid back-mutations selected from the group consisting of R38K, M48I, R67K, V68A, M70L, R72V, T74K and L83F in the heavy chain variable region as shown in SEQ ID NO: 63;

(iv) a variant, comprising one or more amino acid back-mutations selected from the group consisting of F29I, R38K, V48I, R72A, and T97F in the heavy chain variable region as shown in SEQ ID NO: 69, and/or N55V mutation in CDR; or (v) a variant, comprising one or more amino acid back-mutations selected from the group consisting of R38K, M48I, R67K, V68A, R72A, T74K, M81L, L83F and D89E in the heavy chain variable region as shown in SEQ ID NO: 75.

In alternative embodiments, the humanized anti-IL-5 antibody in the pharmaceutical composition comprises:

a heavy chain variable region as shown in SEQ ID NO: 50 or 51; or a heavy chain variable region as shown in SEQ ID NO: 58 or 59; or a heavy chain variable region as shown in any one selected from the group consisting of: SEQ ID NO: 64, 65 and 66; or a heavy chain variable region as shown in SEQ ID NO: 70 or 71; or a heavy chain variable region as shown in any one selected from the group consisting of: SEQ ID NO: 76, 77, 78 and 79.

In alternative embodiments, the humanized anti-IL-5 antibody in the pharmaceutical composition comprises a light chain variable region as shown in SEQ ID NO: 46, 54, 60, 67 or 72, or variants thereof; the variant comprises 1 to 10 amino acid back-mutations in the light chain variable region as shown in SEQ ID NO: 46, 54, 60, 67 or 72.

In alternative embodiments, wherein the variant is a variant as shown in any one selected from the group consisting of:

(i) a variant, comprising one or more amino acid back-mutations selected from the group consisting of A43S, L47V, G66R, T69S, F71Y and Y87F in the light chain variable region as shown in SEQ ID NO: 46;

(ii) a variant, comprising one or more amino acid back-mutations selected from the group consisting of A43S, L47M, F71Y and Y87F in the light chain variable region as shown in SEQ ID NO: 54;

(iii) a variant, comprising amino acid back-mutation(s) selected from the group consisting of E1D, I2T, 157V, V84T and Y86F in the light chain variable region as shown in SEQ ID NO: 60, or the combination thereof;

(iv) a variant, comprising one or more amino acid back-mutations selected from the group consisting of: M4L, A42S, L45P and L46W in the light chain variable region as shown in SEQ ID NO: 67; and (v) a variant, comprising one or more amino acid back-mutations selected from the group consisting of A43S, I48V and F71Y in the light chain variable region as shown in SEQ ID NO: 72.

In alternative embodiments, the humanized anti-IL-5 antibody in the pharmaceutical composition comprises:

a light chain variable region as shown in SEQ ID NO: 47 or 48; or a light chain variable region as shown in SEQ ID NO: 55 or 56; or a light chain variable region as shown in SEQ ID NO: 61 or 62; or a light chain variable region as shown in SEQ ID NO: 68; or a light chain variable region as shown in SEQ ID NO: 73 or 74.

In alternative embodiments, the humanized anti-IL-5 antibody in the pharmaceutical composition comprises:

(i) a heavy chain variable region as shown in any one of SEQ ID NO: 49, 50 and 51 or having 95% sequence identity with any one of SEQ ID NO: 49, 50 and 51; and a light chain variable region as shown in any one of SEQ ID NO: 46, 47 and 48 or having 95% sequence identity with any one of SEQ ID NO: 46, 47 and 48;

(ii) a heavy chain variable region as shown in any one of SEQ ID NO: 57, 58 and 59 or having 95% sequence identity with any one of SEQ ID NO: 57, 58 and 59; and a light chain variable region as shown in any one of SEQ ID NO: 54, 55 and 56 or having 95% sequence identity with any one of SEQ ID NO: 54, 55 and 56;

(iii) a heavy chain variable region as shown in any one of SEQ ID NO: 63, 64, 65 and 66 or having 95% sequence identity with any one of SEQ ID NO: 63, 64, 65 and 66; and a light chain variable region as shown in any one of SEQ ID NO: 60, 61 and 62 or having 95% sequence identity with any one of SEQ ID NO: 60, 61 and 62;

(iv) a heavy chain variable region as shown in any one of SEQ ID NO: 69, 70 and 71 or having 95% sequence identity with any one of SEQ ID NO: 69, 70 and 71; and a light chain variable region as shown in any one of SEQ ID NO: 67 and 68 or having 95% sequence identity with any one of SEQ ID NO: 67 and 68; or (v) a heavy chain variable region as shown in any one of SEQ ID NO: 75, 76, 77, 78 and 79 or having 95% sequence identity with any one of SEQ ID NO: 75, 76, 77, 78 and 79; and a light chain variable region as shown in any one of SEQ ID NO: 72, 73 and 74 or having 95% sequence identity with any one of SEQ ID NO: 72, 73 and 74; preferably, the humanized anti-IL-5 antibody comprises:

(a) the heavy chain variable region as shown in SEQ ID NO: 51 and the light chain variable region as shown in SEQ ID NO: 47;

(b) the heavy chain variable region as shown in SEQ ID NO: 65 and the light chain variable region as shown in SEQ ID NO: 62;

(c) the heavy chain variable region as shown in SEQ ID NO: 58 and the light chain variable region as shown in SEQ ID NO: 56;

(d) the heavy chain variable region as shown in SEQ ID NO: 71 and the light chain variable region as shown in SEQ ID NO: 68; or (e) the heavy chain variable region as shown in SEQ ID NO: 79 and the light chain variable region as shown in SEQ ID NO: 73.

The amino acid sequence having at least 95% sequence identity as described above, preferably has at least 95%, 96%, 97%, 98% or 99% sequence identity, and more preferably has 97%, 98% or 99% or above, and most preferably has at least 99% sequence identity or above, the amino acid sequence having at least 95% sequence identity as described above comprises one or more amino acid deletions, insertions or substitutions obtained by mutation.

In alternative embodiments, the anti-IL-5 antibody in the pharmaceutical composition comprises a human antibody constant region, preferably a human antibody heavy chain constant region as shown in SEQ ID NO: 52 and a human antibody light chain constant region as shown in SEQ ID NO: 53.

In alternative embodiments, the anti-IL-5 antibody in the pharmaceutical composition comprises:

(i) a heavy chain as shown in SEQ ID NO: 83 and a light chain as shown in SEQ ID NO: 84;

(ii) a heavy chain as shown in SEQ ID NO: 85 and a light chain as shown in SEQ ID NO: 86;

(iii) a heavy chain as shown in SEQ ID NO: 87 and a light chain as shown in SEQ ID NO: 88;

(iv) a heavy chain as shown in SEQ ID NO: 89 and a light chain as shown in SEQ ID NO: 90; or (v) a heavy chain as shown in SEQ ID NO: 91 and a light chain as shown in SEQ ID NO: 92.

In alternative embodiments, the anti-IL-5 antibody in the pharmaceutical composition is a monoclonal antibody or antigen-binding fragment thereof that competes for binding to IL-5 with the anti-IL-5 antibody or the antigen-binding fragment thereof as described above.

In a preferred embodiment, the antigen-binding fragment in the pharmaceutical composition of the present disclosure is selected from the group consisting of Fab, Fab', F(ab')2, single-chain antibody (scFv), dimerized V region (diabody) and disulfide bond stabilized V region (dsFv).

The present disclosure further provides a method for preparing the pharmaceutical composition as described above, wherein it comprises a step of replacing a stock solution of the anti-IL-5 antibody with a buffer. In alternative embodiments, preferably the buffer is acetic acid-sodium acetate buffer. The pH of the buffer is about 5.0 to about 6.5, preferably about 5.5 to about 6.5, preferably about 6.0 to about 6.5, preferably about 5.0 to about 6.0, preferably about 5.5 to about 6.0, preferably about 5.0 to about 5.5, preferably about 5.2 to about 5.8, non-limiting examples of the buffer pH value involve about 5.0, about 5.1, about 5.2, about 5.3, about 5.4, about 5.5, about 5.6, about 5.7, about 5.8, about 5.9, about 6.0, about 6.5, and most preferably about 5.5. In alternative embodiments, the concentration of the buffer in the pharmaceutical composition is about 10 mM to about 30 mM, preferably about 15 mM to about 30 mM, preferably about 20 mM to about 30 mM, preferably about 25 mM to about 30 mM, preferably about 5 mM to about 25 mM, preferably about 10 mM to about 25 mM, preferably about 15 mM to about 25 mM, preferably about 20 mM to about 25 mM, preferably about 5 mM to about 20 mM, preferably about 10 mM to about 15 mM; non-limiting examples of the concentration of the buffer involve about 10 mM, about 12 mM, about 14 mM, about 16 mM, about 18 mM, about 20 mM, about 22 mM, about 24 mM, about 26 mM, about 28 mM, about 30 mM, and most preferably about 30 mM.

In some embodiments, the pharmaceutical composition comprises: 100 mg/ml anti-IL-5 antibody h1705-008, 10 mM acetic acid-sodium acetate, pH 5.5 and 0.2 mg/mL polysorbate 80.

In some embodiments, the pharmaceutical composition comprises: 100 mg/ml anti-IL-5 antibody h1705-008, 10 mM acetic acid-sodium acetate, pH 5.5 and 0.05 mg/mL polysorbate 80.

In some embodiments, the pharmaceutical composition comprises: 100 mg/ml anti-IL-5 antibody h1705-008, 10 mM succinic acid-sodium succinate, pH 5.0 and 0.2 mg/mL polysorbate 80.

In some embodiments, the pharmaceutical composition comprises: 100 mg/ml anti-IL-5 antibody h1705-008, 10 mM succinic acid-sodium succinate, pH 5.5 and 0.2 mg/mL polysorbate 80.

In some embodiments, the pharmaceutical composition comprises: 100 mg/ml anti-IL-5 antibody h1705-008, 10 mM succinic acid-sodium succinate, pH 6.0 and 0.2 mg/mL polysorbate 80.

In some embodiments, the pharmaceutical composition comprises: 100 mg/ml anti-IL-5 antibody h1705-008, 10 mM succinic acid-sodium succinate, pH 5.0 and 0.05 mg/mL polysorbate 80.

In some embodiments, the pharmaceutical composition comprises: 100 mg/ml anti-IL-5 antibody h1705-008, 10 mM succinic acid-sodium succinate, pH 5.5 and 0.05 mg/mL polysorbate 80.

In some embodiments, the pharmaceutical composition comprises: 100 mg/ml anti-IL-5 antibody h1705-008, 10 mM succinic acid-sodium succinate, pH 6.0 and 0.05 mg/mL polysorbate 80.

In some embodiments, the pharmaceutical composition comprises: 100 mg/ml anti-IL-5 antibody h1705-008, 10 mM citric acid-sodium citrate, pH 6.5 and 0.2 mg/mL polysorbate 80.

In some embodiments, the pharmaceutical composition comprises: 100 mg/ml anti-IL-5 antibody h1705-008, 10 mM citric acid-sodium citrate, pH 5.5 and 0.2 mg/mL polysorbate 80.

In some embodiments, the pharmaceutical composition comprises: 100 mg/ml anti-IL-5 antibody h1705-008, 10 mM citric acid-sodium citrate, pH 6.0 and 0.2 mg/mL polysorbate 80.

In some embodiments, the pharmaceutical composition comprises: 100 mg/ml anti-IL-5 antibody h1705-008, 10 mM citric acid-sodium citrate, pH 6.5 and 0.05 mg/mL polysorbate 80.

In some embodiments, the pharmaceutical composition comprises: 100 mg/ml anti-IL-5 antibody h1705-008, 10 mM citric acid-sodium citrate, pH 5.5 and 0.05 mg/mL polysorbate 80.

In some embodiments, the pharmaceutical composition comprises: 100 mg/ml anti-IL-5 antibody h1705-008, 10 mM citric acid-sodium citrate, pH 6.0 and 0.05 mg/mL polysorbate 80.

In some embodiments, the pharmaceutical composition comprises: 100 mg/ml anti-IL-5 antibody h1705-008, 10 mM citric acid-sodium citrate, pH 6.5 and 0.2 mg/mL polysorbate 80.

In some embodiments, the pharmaceutical composition comprises: 100 mg/ml anti-IL-5 antibody h1705-008, 10 mM citric acid-sodium citrate, pH 5.5 and 0.2 mg/mL polysorbate 80.

In some embodiments, the pharmaceutical composition comprises: 100 mg/ml anti-IL-5 antibody h1705-008, 10 mM histidine-hydrochloric acid, pH 6.0 and 0.2 mg/mL polysorbate 80.

In some embodiments, the pharmaceutical composition comprises: 100 mg/ml anti-IL-5 antibody h1705-008, 10 mM histidine-hydrochloric acid, pH 6.5 and 0.05 mg/mL polysorbate 80.

In some embodiments, the pharmaceutical composition comprises: 100 mg/ml anti-IL-5 antibody h1705-008, 10 mM histidine-hydrochloric acid, pH 5.5 and 0.05 mg/mL polysorbate 80.

In some embodiments, the pharmaceutical composition comprises: 100 mg/ml anti-IL-5 antibody h1705-008, 10 mM histidine-hydrochloric acid, pH 6.0 and 0.05 mg/mL polysorbate 80.

In some embodiments, the pharmaceutical composition comprises: 100 mg/ml anti-IL-5 antibody h1705-008, 10 mM succinic acid-sodium succinate, pH 5.0 and 0.1 mg/mL polysorbate 20.

In some embodiments, the pharmaceutical composition comprises: 100 mg/ml anti-IL-5 antibody h1705-008, 10 mM succinic acid-sodium succinate, pH 5.0 and 0.1 mg/mL polysorbate 80.

In some embodiments, the pharmaceutical composition comprises: 100 mg/ml anti-IL-5 antibody h1705-008, 10 mM succinic acid-sodium succinate pH 5.0, 50 mg/mL sucrose and 0.1 mg/mL polysorbate 80.

In some embodiments, the pharmaceutical composition comprises: 100 mg/ml anti-IL-5 antibody h1705-008, 10 mM succinic acid-sodium succinate pH 5.0, 50 mg/mL trehalose and 0.1 mg/mL polysorbate 80.

In some embodiments, the pharmaceutical composition comprises: 100 mg/ml anti-IL-5 antibody h1705-008, 10 mM succinic acid-sodium succinate pH 5.0, 50 mg/mL mannitol and 0.1 mg/mL polysorbate 80.

In some embodiments, the pharmaceutical composition comprises: 100 mg/ml anti-IL-5 antibody h1705-008, 10 mM succinic acid-sodium succinate pH 5.0, 50 mg/mL sorbitol and 0.1 mg/mL polysorbate 80.

In some embodiments, the pharmaceutical composition comprises: 100 mg/ml anti-IL-5 antibody h1705-008, 10 mM succinic acid-sodium succinate pH 5.0, 8 mg/mL glycine and 0.1 mg/mL polysorbate 80.

In some embodiments, the pharmaceutical composition comprises: 100 mg/ml anti-IL-5 antibody h1705-008, 10 mM succinic acid-sodium succinate pH 5.0, 8 mg/mL methionine and 0.1 mg/mL polysorbate 80.

In some embodiments, the pharmaceutical composition comprises: 100 mg/ml anti-IL-5 antibody h1705-008, 10 mM succinic acid-sodium succinate pH 5.0, 8 mg/mL proline and 0.1 mg/mL polysorbate 80.

In some embodiments, the pharmaceutical composition comprises: 100 mg/ml anti-IL-5 antibody h1705-008, 10 mM succinic acid-sodium succinate pH 5.5, 70 mg/mL sucrose and 0.4 mg/mL polysorbate 80.

In some embodiments, the pharmaceutical composition comprises: 80 mg/ml anti-IL-5 antibody h1705-008, 10 mM acetic acid-sodium acetate pH 5.8 and 0.2 mg/mL polysorbate 80.

In some embodiments, the pharmaceutical composition comprises: 100 mg/ml anti-IL-5 antibody h1705-008, 10 mM acetic acid-sodium acetate pH 5.4 and 0.6 mg/mL polysorbate 80.

In some embodiments, the pharmaceutical composition comprises: 80 mg/ml anti-IL-5 antibody h1705-008, 10 mM acetic acid-sodium acetate pH 5.4 and 0.4 mg/mL polysorbate 80.

In some embodiments, the pharmaceutical composition comprises: 80 mg/ml anti-IL-5 antibody h1705-008, 10 mM acetic acid-sodium acetate pH 5.0 and 0.2 mg/mL polysorbate 80.

In some embodiments, the pharmaceutical composition comprises: 100 mg/ml anti-IL-5 antibody h1705-008, 10 mM acetic acid-sodium acetate pH 5.4 and 0.2 mg/mL polysorbate 80.

In some embodiments, the pharmaceutical composition comprises: 80 mg/ml anti-IL-5 antibody h1705-008, 10 mM acetic acid-sodium acetate pH5.8 and 0.6 mg/mL polysorbate 80.

In some embodiments, the pharmaceutical composition comprises: 120 mg/ml anti-IL-5 antibody h1705-008, 10 mM acetic acid-sodium acetate pH 5.0 and 0.2 mg/mL polysorbate 80.

In some embodiments, the pharmaceutical composition comprises: 80 mg/ml anti-IL-5 antibody h1705-008, 10 mM acetic acid-sodium acetate pH 5.0 and 0.6 mg/mL polysorbate 80.

In some embodiments, the pharmaceutical composition comprises: 120 mg/ml anti-IL-5 antibody h1705-008, 10 mM acetic acid-sodium acetate pH 5.8 and 0.6 mg/mL polysorbate 80.

In some embodiments, the pharmaceutical composition comprises: 120 mg/ml anti-IL-5 antibody h1705-008, 10 mM acetic acid-sodium acetate pH 5.4 and 0.4 mg/mL polysorbate 80.

In some embodiments, the pharmaceutical composition comprises: 100 mg/ml anti-IL-5 antibody h1705-008, 10 mM acetic acid-sodium acetate pH 5.4 and 0.4 mg/mL polysorbate 80.

In some embodiments, the pharmaceutical composition comprises: 120 mg/ml anti-IL-5 antibody h1705-008, 10 mM acetic acid-sodium acetate pH 5.0 and 0.6 mg/mL polysorbate 80.

In some embodiments, the pharmaceutical composition comprises: 120 mg/ml anti-IL-5 antibody h1705-008, 10 mM acetic acid-sodium acetate pH 5.8 and 0.2 mg/mL polysorbate 80.

In some embodiments, the pharmaceutical composition comprises: 100 mg/ml anti-IL-5 antibody h1705-008, 10 mM acetic acid-sodium acetate pH 5.0 and 0.4 mg/mL polysorbate 80.

In some embodiments, the pharmaceutical composition comprises: 100 mg/ml anti-IL-5 antibody h1705-008, 10 mM acetic acid-sodium acetate pH 5.8 and 0.4 mg/mL polysorbate 80.

In some embodiments, the pharmaceutical composition comprises: 100 mg/ml anti-IL-5 antibody h1705-008, 10 mM acetic acid-sodium acetate pH 5.5, 70 mg/ml sucrose and 0.4 mg/mL polysorbate 80.

In some embodiments, the pharmaceutical composition comprises: 100 mg/ml anti-IL-5 antibody h1705-008, 20 mM acetic acid-sodium acetate pH 5.5, 70 mg/ml sucrose and 0.4 mg/mL polysorbate 80.

In some embodiments, the pharmaceutical composition comprises: 100 mg/ml anti-IL-5 antibody h1705-008, 30 mM acetic acid-sodium acetate pH 5.5, 70 mg/ml sucrose and 0.4 mg/mL polysorbate 80.

In some embodiments, the pharmaceutical composition comprises: 100 mg/ml anti-IL-5 antibody h1705-008, 30 mM acetic acid-sodium acetate pH 5.5, 73 mg/ml sucrose and 0.4 mg/mL polysorbate 80.

In some embodiments, the pharmaceutical composition comprises: 100 mg/ml anti-IL-5 antibody h1705-008, 30 mM acetic acid-sodium acetate pH 5.5, 75 mg/ml sucrose and 0.4 mg/mL polysorbate 80.

In some embodiments, the pharmaceutical composition of the present disclosure is stable at 2-8° C. for at least 3 months, at least 6 months, at least 12 months, at least 18 months, or at least 24 months. The pharmaceutical composition can be stable at 25° C. for at least 3 months, at least 6 months.

The present disclosure further provides a method for preparing a lyophilized formulation comprising an anti-IL-5 antibody, which comprises a step of lyophilizing the pharmaceutical composition as described above.

In an alternative embodiment, the lyophilization in the method for preparing the lyophilized formulation comprising an anti-IL-5 antibody comprises the steps of pre-freezing, primary drying and secondary drying, successively. The lyophilization is carried out by freezing the formulation and subsequently sublimating the water at a temperature suitable for primary drying. Under such condition, the temperature of the product is lower than the eutectic point or decomposition temperature of the formulation. Under a suitable pressure, typically in the range of about 50 to 250 mTorr, the storage temperature for primary drying is usually about −30 to 25° C. (assuming that the product remains frozen during the primary drying). The formulation, the size and type of sample container (for example, glass vial) and the volume of liquid determine the time duration required for drying, and the time duration can range from several hours to several days (for example, 40 to 60 hours). The secondary drying can be carried out at about 0 to 40° C., which mainly depends on the type and size of the container and the type of protein used. The time duration for secondary drying is determined by the desired residual humidity level of the product, and usually requires at least about 5 hours. Generally, the water content in lyophilized formulation prepared under low-pressure is less than about 5%, preferably less than about 3%. The pressure can be the same as the pressure applied in the primary drying step; preferably the pressure used in the secondary drying is lower than that used in the primary drying. The conditions for lyophilization can vary with the formulation and vial size.

The present disclosure further provides a lyophilized formulation comprising an IL-5 antibody prepared by the method for preparing a lyophilized formulation comprising an anti-IL-5 antibody as described above.

In some embodiments, the lyophilized formulation is stable at 2-8° C. for at least 3 months, at least 6 months, at least 12 months, at least 18 months or at least 24 months. In some embodiments, the lyophilized formulation is stable at 40° C. for at least 7 days, at least 14 days or at least 28 days.

The present disclosure further provides a method for preparing a reconstituted solution of the lyophilized formulation comprising an anti-IL-5 antibody, wherein it comprises a step of reconstituting the lyophilized formulation as described above, and the solution used for the reconstitution comprises, but not limited to, water for injection, normal saline or glucose solution.

The present disclosure further provides a reconstituted solution of the lyophilized formulation comprising an IL-5 antibody prepared by the method for preparing a reconstituted solution of the lyophilized formulation comprising an anti-IL-5 antibody as described above.

The present disclosure further provides an article or kit which comprises container(s) comprising any of the stable pharmaceutical compositions herein. In some embodiments, the container is an injection vial made of neutral borosilicate glass.

The present disclosure further provides an article, which comprises container(s) comprising the pharmaceutical composition or the lyophilized formulation or the reconstituted solution of lyophilized formulation as described above.

The present disclosure further provides a method for treating IL-5 mediated disease(s), comprising administering a therapeutically effective amount of the pharmaceutical composition or the lyophilized formulation or the reconstituted solution or the article of manufacture as described above, to a subject in need thereof, wherein the IL-5 mediated disease is preferably selected from the group consisting of asthma, chronic pneumonia, allergic rhinitis, allergic bronchopulmonary aspergillosis disease, eosinophilia, Churg-Strauss syndrome, atopic dermatitis, onchocerciasis dermatitis, intermittent angioedema, eosinophilic myalgia syndrome, eosinophilic gastroenteritis, worm infection, Hodgkin's disease, nasal polyps, Loeffler's syndrome, urticaria, hypereosinophilic bronchitis, nodular arteritis, sinusitis, eosinophilic esophagitis, allergic eosinophilic esophagitis, allergic conjunctivitis, onchocerciasis dermatitis, endometriosis and steroid-dependent eosinophilic bronchitis.

The present disclosure further provides the use of the pharmaceutical composition or the lyophilized formulation or the reconstituted solution of the lyophilized formulation or the article of manufacture as described above in the preparation of a medicament for treating IL-5 mediated disease(s); wherein the IL-5 mediated disease is preferably selected from the group consisting of asthma, chronic pneumonia, allergic rhinitis, allergic bronchopulmonary aspergillosis disease, eosinophilia, Churg-Strauss syndrome, atopic dermatitis, onchocerciasis dermatitis, intermittent angioedema, eosinophilic myalgia syndrome, eosinophilic gastroenteritis, worm infection, Hodgkin's disease, nasal polyps, Loeffler's syndrome, urticaria, hypereosinophilic bronchitis, nodular arteritis, sinusitis, eosinophilic esophagitis, allergic eosinophilic esophagitis, allergic conjunctivitis, onchocerciasis dermatitis, endometriosis and steroid-dependent eosinophilic bronchitis.

The present disclosure further provides the pharmaceutical composition or the lyophilized formulation or the reconstituted solution of the lyophilized formulation or the article of manufacture as described above, for use as a therapeutic medicament, wherein the medicament is for treating IL-5 mediated disease(s); wherein the IL-5 mediated disease is preferably selected from the group consisiting of asthma, chronic pneumonia, allergic rhinitis, allergic bronchopulmonary aspergillosis disease, eosinophilia, Churg-Strauss syndrome, atopic dermatitis, onchocerciasis dermatitis, intermittent angioedema, eosinophilic myalgia syndrome, eosinophilic gastroenteritis, worm infection, Hodgkin's disease, nasal polyps, Loeffler's syndrome, urticaria, hypereosinophilic bronchitis, nodular arteritis, sinusitis, eosinophilic esophagitis, allergic eosinophilic esophagitis, allergic conjunctivitis, onchocerciasis dermatitis, endometriosis and steroid-dependent eosinophilic bronchitis.

As is well known to those skilled in the art, one, some or all of the features of each embodiment in the present disclosure can be further combined to form other embodiments of the present disclosure. The embodiments of the present disclosure as described above and additional embodiments obtained by combination are further illustrated by the detailed description below.

DETAILED DESCRIPTION OF THE EMBODIMENTS

Terms

Figure 1:
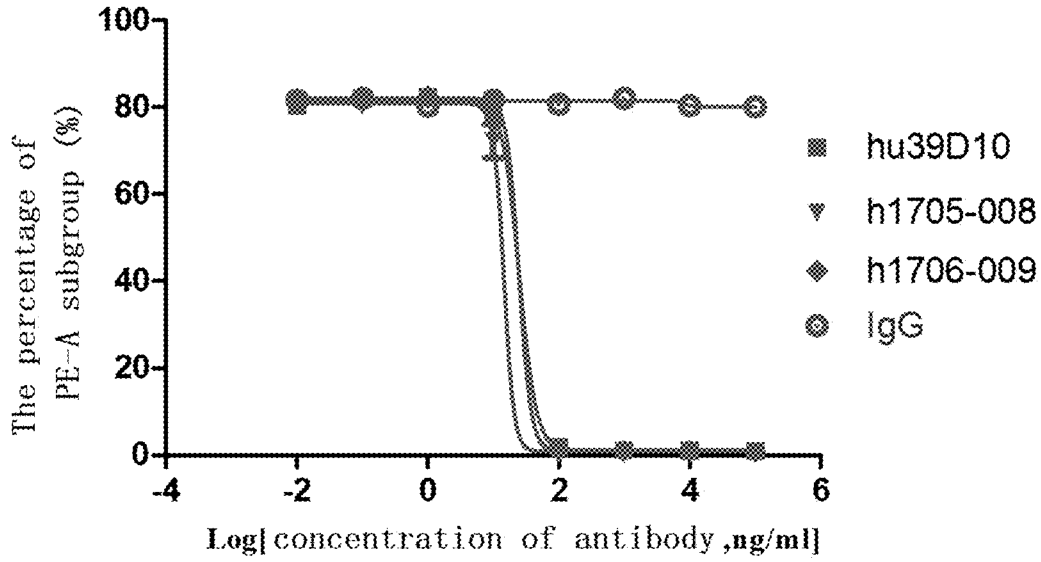
FIG. 1 represents the results of FACS experiments in which anti-IL-5 antibodies block the binding of IL-5 to IL-5 receptor.

In order to understand the present disclosure more easily, certain technical and scientific terms are specifically defined below. All other technical and scientific terms used herein have the meaning commonly understood by one of ordinary skill in the art to which the present disclosure pertains, unless otherwise explicitly defined herein.

"Buffer" refers to a buffer that is resistant to changes in pH by the action of its acid-base conjugate components. Examples of the buffer which controls the pH within an appropriate range include acetate, succinate, gluconate, histidine salt, oxalate, lactate, phosphate, citrate, tartrate, fumarate, glycyl-glycine and other organic acid buffers.

"Histidine salt buffer" is a buffer comprising histidine ions. Examples of the histidine salt buffer include histidine-hydrochloride, histidine-acetate, histidine-phosphate, histidine-sulfate buffer, and the like; preferably, histidine-acetate buffer or histidine-hydrochloride buffer; histidine-acetate buffer is prepared by histidine and acetic acid, and histidine salt buffer is prepared by histidine and HCl.

"Citrate buffer" is a buffer comprising citrate ions. Examples of the citrate buffer include citric acid-sodium citrate, citric acid-potassium citrate, citric acid-calcium citrate, citric acid-magnesium citrate, and the like. A preferred citrate buffer is citric acid-sodium citrate.

"Succinate buffer" is a buffer comprising succinate ions. Examples of the succinate buffer include succinic acid-sodium succinate, succinic acid-potassium succinate, succinic acid-calcium succinate, and the like. A preferred succinate buffer is succinic acid-sodium succinate.

"Phosphate buffer" is a buffer comprising phosphate ions. Examples of the phosphate buffer include disodium hydrogen phosphate-sodium dihydrogen phosphate, disodium hydrogen phosphate-potassium dihydrogen phosphate, disodium hydrogen phosphate-citric acid, and the like. A preferred phosphate buffer is disodium hydrogen phosphate-sodium dihydrogen phosphate.

"Acetate buffer" is a buffer comprising acetate ions. Examples of the acetate buffer include acetic acid-sodium acetate, histidine acetate, acetic acid-potassium acetate, acetic acid-calcium acetate, acetic acid-magnesium acetate, and the like. A preferred acetate buffer is acetic acid-sodium acetate.

"Pharmaceutical composition" means a mixture comprising one or more of the compounds (or physiological/pharmaceutically acceptable salt or prodrug thereof) described herein and other chemical components (such as physiological/pharmaceutically acceptable carriers and excipients). The purpose of a pharmaceutical composition is to maintain stability of antibody active ingredients, and to facilitate the administration to organism, so as to facilitate the absorption and the biological activity of the active ingredient.

As used herein, "pharmaceutical composition" and "formulation" are used interchangeably.

The "saccharide" in the present disclosure includes conventional $(CH_2O)_n$ and the derivatives thereof, including monosaccharides, disaccharides, trisaccharides, polysaccharides, sugar alcohols, reducing saccharides, non-reducing saccharides, etc. The saccharide can be selected from the group consisting of: glucose, sucrose, trehalose, lactose, fructose, maltose, dextran, glycerol, erythritol, glycerol, arabitol, xylitol, sorbitol, mannitol, melibiose, melezitose, melitriose, mannotriose, stachyose, maltose, lactulose, maltulose, sorbitol, maltitol, lactitol, iso-maltulose, etc. The preferred saccharide is non-reducing disaccharide, more preferred sucrose.

According to the present disclosure, the solvent comprised in the solution form of the pharmaceutical composition is water, unless otherwise specified.

"Lyophilized formulation" means a formulation or a pharmaceutical composition obtained by vacuum lyophilization of the liquid or solution form of the pharmaceutical composition or the formulation.

The lyophilization in the present disclosure comprises pre-freezing, primary drying and secondary drying. The purpose of pre-freezing is to freeze the products to obtain crystalline solids. Pre-freezing temperature and pre-freezing speed are two important process parameters. In the present disclosure, the pre-freezing temperature is set to −45° C., with the pre-freezing speed at 1° C./min. The primary drying, also called main drying, is the main stage for lyophilization of samples. The purpose is to remove ice from the product while maintaining the shape of the product, so as to limit the damage to a product to minimum level. When the primary drying temperature and vacuum degree are not selected properly, the product would collapse. Higher temperature and higher vacuum degree accelerate the lyophilization efficiency, but also increase the risk of product collapse. The temperature of primary drying in present invention can be a conventional temperature in the field, such as −30° C. to 0° C. The secondary drying is also called vacuum drying, is a main step which removes the bound water from a product by pumping an ultimate vacuum (0.01 mbar) and raising the temperature (20 to 40° C.). Since most biological products are sensitive to temperature, the selected secondary drying temperature shall be at the lower point of the temperature range, which is 25° C. The time duration for lyophilization is related to the freezer, the dose of the formulation to be lyophilized, and the container of the formulation to be lyophilized. Those skilled in the art well know how to adjust such time duration.

As used herein, the term "about" and "approximately" means that a value is within an acceptable error range of the specific value measured by an ordinary skilled in the art. The value partly depends on how the value is measured or determined (i.e. the limit of the measurement system). For example, in every practice in the art, "about" means a standard deviation within 1 or more than 1. As an alternative, "about" or "substantially comprising" means a range of at most ±20%, for example, a pH of about 5.5 means pH 5.5±1.1. In addition, especially for biological systems or processes, the term means at most one order of magnitude or at most 5-folds of a value. Unless otherwise specified, when the specific value is indicated in the present application and claims, the meaning of "about" or "substantially comprising" should be within an acceptable error range of the specific value.

The pharmaceutical composition of the present disclosure is capable of achieving a stable effect: i.e., the antibody comprised in the pharmaceutical composition substantially retains the physical stability and/or chemical stability and/or biological activity following the storage. Preferably, the pharmaceutical composition substantially retains the physical stability and chemical stability as well as biological activity following the storage. The storage period is generally determined based on the predetermined shelf-life of the pharmaceutical composition. There are currently a number of analytical techniques for measuring the stability of a protein, which can be used to measure the stability after being stored for a selected period of time at a selected temperature.

A stable pharmaceutical formulation of antibody is a formulation for which no significant physical and/or chemical and/or biological change is observed under the following conditions: being stored at a cool temperature (2-8° C.) for at least 3 months, preferably 6 months, more preferably 1 year, and even more preferably up to 2 years. In addition, stable liquid formulations include those exhibit desirable characteristics after being stored at temperature of 25° C. for 1 month, 3 months or 6 months. Typically, criteria for stable formulation are as follows: typically no more than about 10%, preferably no more than about 5% of the antibody monomers being degraded, as measured by SEC-HPLC; by visual inspection, the pharmaceutical formulation of antibody is light yellow, almost colorless clear liquid, or colorless, or clear to slightly pale; no more than ±10% variation occurs in the concentration, pH and osmolality of the formulation; generally no more than about 10%, preferably no more than about 5% of reduction is observed; generally no more than about 10%, preferably no more than about 5% of aggregation is formed.

An antibody would be deemed to "retain its physical stability" in the pharmaceutical formulation, when the antibody does not show a significantly increased aggregation, precipitation and/or denaturation, by visual inspection of color and/or clarity, or being measured via UV light scattering, size exclusion chromatography (SEC) and dynamic light scattering (DLS). Changes in protein conformation can be assessed by fluorescence spectroscopy, which determines the tertiary structure of a protein, and by FTIR spectroscopy, which determines the secondary structure of a protein.

An antibody would be deemed to "retain its chemical stability" in the pharmaceutical formulation, when the antibody does not show a significant chemical modification. Chemical stability can be assessed by detecting and quantifying chemically altered forms of a protein. Degradation processes that frequently alter the chemical structure of a protein include hydrolysis or truncation (assessed by methods such as size exclusion chromatography and SDS-PAGE), oxidation (assessed by methods such as peptide spectroscopy in combination with mass spectrometry or MALDI/TOF/MS), deamidation (assessed by methods such as ion exchange chromatography, capillary isoelectric focusing, peptide spectroscopy, isoaspartic acid measurement) and isomerization (assessed by methods such as measuring the content of isoaspartic acid, peptide spectroscopy).

An antibody would be deemed to "retain its biological activity" in the pharmaceutical formulation, when the biological activity of the antibody at a given time is still within the predetermined range of biological activity exhibited at the time when the pharmaceutical formulation was initially prepared. The biological activity of the antibody can be determined, for example, by antigen-binding assay.

The three-letter code and the one-letter code for amino acids used in the present disclosure are described in J. biol. chem. 243, p3558 (1968).

The "antibody" used in the present disclosure refers to immunoglobulin; a complete antibody is a tetra-peptide chain structure composed of two identical heavy chains and two identical light chains connected by inter-chain disulfide bond(s).

In the present disclosure, the antibody light chain of the present disclosure further comprises a light chain constant region, and the light chain constant region includes human or murine, 2 chain or the variant(s) thereof.

In the present disclosure, the antibody heavy chain of the present disclosure further comprises a heavy chain constant region, and the heavy chain constant region includes human or murine IgG1, IgG2, IgG3, IgG4 or the variant(s) thereof.

The about 110 amino acid adjacent to the N-terminus of the antibody heavy and light chains are highly variable, known as variable regions (Fv regions); the rest of amino acid sequences close to the C-terminus are relatively stable, known as constant regions. The variable region includes three hypervariable regions (HVRs) and four relatively conservative framework regions (FRs). The three hypervariable regions which determine the specificity of the antibody are also known as complementarity determining regions (CDRs). Each of the light chain variable region (LCVR, VL) and heavy chain variable region (HCVR, VH) consists of 3 CDR regions and 4 FR regions, with the sequential order from the amino terminus to carboxyl terminus of: FR1, CDR1, FR2, CDR2, FR3, CDR3, and FR4. The three CDR regions of the light chain refer to LCDR1, LCDR2, and LCDR3, and the three CDR regions of the heavy chain refer to HCDR1, HCDR2, and HCDR3. The number and position of the CDR amino acid residues of the LCVR region and the HCVR region in the antibody or the antigen-binding fragment thereof described in the present disclosure comply with the known Kabat numbering criteria (LCDR 1 to 3, HCDR 1 to 3).

The antibodies of the present disclosure include murine antibodies, chimeric antibodies, humanized antibodies, and preferably humanized antibodies.

In the present disclosure, the "antigen-binding fragment of an antibody" or "functional fragment" refers to Fab fragments, Fab' fragments, F(ab') 2 fragments that have antigen-binding activity, and Fv fragments, scFv fragments that bind to antibody. Fv fragment comprises a heavy chain variable region and a light chain variable region of the antibody, but does not have a constant region, and Fv fragment is the smallest antibody fragment that has all antigen binding sites. Generally, the Fv antibody also comprises a polypeptide linker between VH and VL domains, and is capable of forming a structure required for antigen-binding. Different linkers can also be used to connect two antibody variable regions to form a polypeptide chain, named single chain antibody or single chain Fv (SFv).

The term "antigen-binding site" of the present disclosure refers to a continuous or discontinuous three-dimensional spatial site on an antigen recognized by the antibody or antigen-binding fragment thereof of the present disclosure.

The term "murine antibody" in the present disclosure refers to a monoclonal antibody against human IL-5 prepared according to the knowledge and skills in the art. During the preparation, the test subject is injected with IL-5 antigen, and then hybridoma expressing antibody having desired sequence or functional feature is isolated.

The term "chimeric antibody" is an antibody formed by fusing the variable region of a murine antibody with the constant region of a human antibody, which reduces the immune response induced by the murine antibody. To establish a chimeric antibody, it is necessary to firstly establish a hybridoma secreting murine specific monoclonal antibodies; then the variable region genes are cloned from the mouse hybridoma cells; and then the constant region genes of the human antibodies are cloned as needed; and the murine variable region genes are combined with the human constant region genes to form a chimeric gene which is inserted into a human vector, and finally the chimeric antibody molecule is expressed in a eukaryotic industrial system or a prokaryotic industrial system. In a preferred embodiment of the present disclosure, the light chain of IL-5 chimeric antibody further comprises the light chain constant region of human K, 2 chain or the variant(s) thereof. The heavy chain of the IL-5 chimeric antibody further comprises the heavy chain constant region of human IgG1, IgG2, IgG3, IgG4 or the variant(s) thereof. The constant region of human antibody can be selected from the group consisting of: the heavy chain constant region of human IgG1, IgG2, IgG3 or IgG4 or the variant(s), preferably comprises human IgG2 or IgG4 heavy chain constant region, or IgG4 without ADCC toxicity (antibody-dependent cell-mediated cytotoxicity) after amino acid mutation.

The term "humanized antibody", also known as CDR-grafted antibody, refers to an antibody generated by grafting the murine CDR sequences onto human antibody variable region framework, i.e., an antibody produced in different types of human germline antibody framework sequences. The humanized antibody avoids strong heterogeneous responses induced by chimeric antibody which carries a large number of murine protein components. Such framework sequences can be obtained from public DNA database covering germline antibody gene sequences or published references. For example, germline DNA sequences of human heavy and light chain variable region genes can be found in "VBase" human germline sequence database (available on www.mrccpe.com.ac.uk/vbase), as well as in Kabat, E A, et al. 1991 Sequences of Proteins of Immunological Interest, 5th Ed. To avoid a decrease in activity caused by the decreased immunogenicity, the framework sequences in human antibody variable region may be subjected to minimal reverse-mutation or back-mutation so as to maintain the activity. The humanized antibody of the present disclosure also refers to a humanized antibody on which CDRs affinity maturation is performed by phage display.

In the present disclosure, the "ADCC" (i.e. antibody-dependent cell-mediated cytotoxicity) means that antibody-coated target cells are directly killed by cells expressing Fc receptors, through recognizing the Fc segment of antibody. The ADCC effector function of the antibody can be reduced or eliminated by modifying the Fc segment of IgG. The modification refers to mutations performed on the heavy chain constant region of an antibody, such as selected from the group consisting of: N297A, L234A, L235A on IgG1; IgG2/4 chimera, F234A/L235A mutation on IgG4.

The "mutation" in a mutant sequence in the present disclosure includes but is not limited to "back-mutation(s)", "conservative modification" or "conservative replacement or substitution". The "conservative modification" or "conservative replacement or substitution" used in the present disclosure refers to other amino acids with similar characteristics (such as charge, side chain size, hydrophobicity/hydrophilicity, backbone conformation and rigidity, etc.) are used to replace the amino acids in a protein, so that replacement can be frequently performed without changing the biological activity of a protein. Those skilled persons in the art know that, generally, single amino acid substitution in a non-essential region of a polypeptide does not substantially change the biological activity (see, for example, Watson et al., (1987) Molecular Biology of the Gene, The Benjamin/Cummings Pub. Co., Page 224, (the 4th edition)). In addition, the substitution of amino acids with similar structure or function is unlikely to disrupt the biological activity.

The "mutated sequence" in the present disclosure refers to that the nucleotide sequence and/or amino acid sequence of the present disclosure are appropriately modified by mutation(s) (such as substitution, insertion or deletion) to obtain a nucleotide sequence and/or amino acid sequence which has different sequence identity percentage with the nucleotide sequence and/or amino acid sequence of the present disclosure. In the present disclosure, the sequence identity can be at least 85%, 90% or 95%, preferably at least 95%. Non-limiting examples refer to 85%, 86%, 87%, 88%, 89%, 90%, 91%, 92%, 93%, 94%, 95%, 96%, 97%, 98%, 99%, or 100%. Sequence alignment and determination of identity percentage between two sequences can be performed by the default settings of BLASTN/BLASTP algorithm available on the website of National Center For Biotechnology Institute.

The term "binding to IL-5" refers to an interaction with IL-5, preferably with human IL-5.

The terms "anti-IL-5 antibody" and "IL-5 antibody" are used interchangeably, and both refer to antibody that binds to IL-5.

In the present disclosure, the fusion protein is a protein product obtained by co-expressing two genes through DNA recombination. The recombinant IL-5 extracellular region-Fc fusion protein is a fusion protein obtained by co-expressing IL-5 extracellular region and human antibody Fc fragment, through DNA recombination. The IL-5 extracellular region refers to the portion of IL-5 protein expressed outside the cell membrane, and the sequence thereof is as shown in SEQ ID NO: 1.

The methods for producing and purifying antibodies and antigen-binding fragments are well known and available in the prior art, such as Antibodies: A Laboratory Manual, Cold Spring Harbor press, Chapters 5-8 and 15. For example, mice can be immunized with a human IL-5 or fragment thereof, and the resulting antibody can be renatured and purified, and amino acid sequencing can be performed by using conventional methods. Antigen-binding fragments can also be prepared by using conventional methods. The antibody or antigen-binding fragment according to the present disclosure is genetically engineered to graft one or more human FR region(s) onto the non-human CDR regions. The human FR germline sequences can be obtained from ImMunoGeneTics (IMGT) website, or can be obtained from The Immunoglobulin Journal, 2001ISBN012441351.

The engineered antibody or antigen-binding fragment thereof can be prepared and purified by conventional methods. For example, the cDNA sequences encoding the heavy chain and light chain can be cloned and recombined into a GS expression vector. The expression vectors of recombinant immunoglobulin can be stably transfected into CHO cells. As a recommended prior art, mammalian expression systems can lead to glycosylation of antibodies, especially at highly conservative N-terminal positions of the Fc region. Stable clones are obtained by expressing antibodies that specifically bind to human IL-5. Positive clones are expanded in serum-free culture medium of bioreactors to produce antibodies. The culture medium into which the antibodies are secreted can be purified by conventional techniques. For example, Protein A or Protein G Sepharose FF column comprising adjusted buffer can be used for purification. Non-specifically bound components are washed out. Then the bound antibodies are eluted by pH gradient, and the antibody fragments are detected by SDS-PAGE and collected. The antibodies can be filtered and concentrated by conventional methods. Soluble mixtures and multimers can also be removed by conventional methods, for example molecular sieves and ion exchange. The resulting product shall be frozen immediately, such as at −70° C., or lyophilized.

"Optional" or "optionally" means that the event or environment that follows the term can but does not have to occur, and the description involves occasions where the event or environment would occur or not occur. For example, "optionally comprises 1 to 3 heavy chain CDR region(s) of an antibody" means that the heavy chain CDR region(s) of an antibody having specific sequence(s) can, but not necessarily, be present.

"Administering" and "treating", when applied to animals, humans, experimental subjects, cells, tissues, organs or biological fluids, refer to a contact of exogenous medicament, therapeutic agent, diagnostic agent or composition with the animals, humans, subjects, cells, tissues, organs or biological fluids. "Administering" and "treating" can refer to for example treatment, pharmacokinetics, diagnosis, research and experimental methods. The treatment of cells includes a contact of reagent with cells, and a contact of reagent with fluids, wherein the fluids are in contact with the cells. "Administering" and "treating" for example also mean treatment of cells by reagents, diagnostic agent, binding compositions or by another cell in vitro and ex vivo. "Treating" when applied to human, veterinary or research subjects, refers to therapeutic treatment, prevention or prophylactic measures, research and diagnostic applications.

"Treatment" means applying an internal or external therapeutic agent, for example a composition comprising any one of the binding compounds of the present disclosure, to a patient who has one or more disease symptoms on which the therapeutic agent is known to have therapeutic effect. Generally, the therapeutic agent is given at an amount effective to alleviate one or more disease symptoms in the treated patient or population to induce the regression of such symptoms or inhibit the development of such symptoms to any clinically detectable extent. The amount of therapeutic agent that is effective to alleviate any specific disease symptom (also referred to as a "therapeutically effective amount") can vary according to a variety of factors, for example the patient disease state, age and body weight, and the ability of the agent to produce the desired therapeutic effect in the patient. Whether the disease symptoms have been alleviated can be evaluated through any clinical testing methods commonly used by doctors or other health care professionals to evaluate the severity or progression of the symptoms. Although an embodiment of the present disclosure (for example treatment method or article of manufacture) may not be effective in alleviating each target disease symptom, it should alleviate the target disease symptom in a statistically significant number of patients, as determined according to any statistical test methods known in the art, such as Student t-test, chi-square test, Mann and Whitney's U test, Kruskal-Wallis test (H test), Jonckheere-Terpstra test and Wilcoxon test.

There is no restriction to diseases related to IL-5, as long as it is a disease related to IL-5. For example, the therapeutic response induced by the molecule of the present disclosure can by produced by binding to human IL-5 and subsequently blocking or inhibiting the stimulation effects of eosinophils. Therefore, when applied to preparations and formulations suitable for therapeutic application, the pharmaceutical composition of the present disclosure is very useful for such subjects who suffer from allergies and/or atopic reactions, or suffer from reactions related to eosinophils, such as but not limited to asthma, exacerbation of asthma, malignant onset of asthma, chronic pneumonia, allergic rhinitis, perennial allergic rhinitis, allergic bronchopulmonary aspergillosis disease, eosinophilia, Churg-Strauss syndrome, atopic dermatitis, onchocerciasis dermatitis, intermittent angioedema, eosinophilic myalgia syndrome, eosinophilic gastroenteritis, worm infection, Hodgkin's disease, nasal polyps, Loeffler's syndrome, urticaria, hypereosinophilic bronchitis, nodular arteritis, sinusitis, eosinophilic esophagitis, allergic eosinophilic esophagitis, allergic conjunctivitis, onchocerciasis dermatitis, endometriosis, or steroid-dependent eosinophilic bronchitis, etc. In a preferred embodiment, the treatment can inhibit or alleviate the infiltration of eosinophils into lung tissue. The frequency of administration for the pharmaceutical composition can be from three times per day to once every 6 months. The route of administration can be intravenous, subcutaneous, intramuscular, parenteral or topical route.

The formulations of the present disclosure can be used to treat IL-5 mediated diseases. For example, the formulations can be used to, but not limited to, inhibit or alleviate IL-5 mediated inflammatory response and the maturation, activation, degranulation or tissue infiltration of eosinophils in vivo and in vitro; inhibit the excessive stress of smooth muscle caused by IL-5; reduce the level of IL-5 in lung, airway or blood. Preferably, the formulation of the present disclosure can be used to treat IL-5 mediated diseases, preferably, the IL-5 mediated disease is selected from the group consisting of: asthma, chronic pneumonia, allergic rhinitis, allergic bronchopulmonary aspergillosis disease, eosinophilia, Churg-Strauss syndrome, atopic dermatitis, onchocerciasis dermatitis, intermittent angioedema, eosinophilic myalgia syndrome, eosinophilic gastroenteritis, worm infection, Hodgkin's disease, nasal polyps, Loeffler's syndrome, urticaria, hypereosinophilic bronchitis, nodular arteritis, sinusitis, eosinophilic esophagitis, allergic eosinophilic esophagitis, allergic conjunctivitis, onchocerciasis dermatitis, endometriosis and steroid-dependent eosinophilic bronchitis.

"Effective amount" includes an amount sufficient to improve or prevent the symptoms or conditions of medical disease. An effective amount also refers to an amount sufficient to allow or facilitate diagnosis. The effective amount for a particular patient or veterinary subject may vary depending on the following factors: for example, the condition to be treated, the patient's general condition, the route of administration and dosage, and the severity of side effects. The effective amount can be a maximum dose or dosing schedule that avoids significant side effects or toxic effects.

"Exchange" refers to the exchange of the solvent system that is used to dissolve the antibody protein. For example, a high salt or hypertonic solvent system comprising an antibody protein is replaced with a buffer system of a stable formulation, by physical manipulation, so that the antibody protein would be present in a stable formulation. The physical manipulation includes but not limited to ultrafiltration, dialysis or reconstitution after centrifugation.

EXAMPLES AND TEST EXAMPLES

The present disclosure is further described in conjunction with the examples below, but these examples do not limit the scope of the present disclosure. The experimental methods that are not provided with specific conditions in the example of the present disclosure are usually in accordance with conventional conditions, such as reference to the publications of Antibodies: A Laboratory Manual, Molecular Cloning by Cold Spring Harbor Laboratory; or in accordance with the conditions recommended by the manufacturers of materials or products. Reagents that are not provided with specific sources are conventional reagents purchased on the market.

Example 1. Preparation of IL-5 Antigen and Protein Used in the Detection 1.1 Design and Expression of IL-5 Antigen The sequences encording human IL-5 with His-tag, rhesus IL-5 with His-tag, mouse IL-5 with His-tag, rat IL-5 with His-tag, human IL-5Rα receptor extracellular region fusion protein comprising human IgG1-Fc fragment were cloned into phr vectors, and expression plasmids were constructed and then transfected into HEK293. On day 6 after transfection, samples were collected, and the cell supernatant was collected by centrifugation at 4500 rpm for 10 min. The supernatants comprising the recombinant IL-5 and IL-5a receptor proteins were purified by using nickel column, the recombinant human IL-5-Fc fusion protein was purified by using Protein A affinity chromatography column. The purified protein can be used in subsequent experiments. The sequences for the specific protein antigens are as follows:

The amino acid sequence for human IL-5 with his-tag (rhIL-5-his)

SEQ ID NO: 1

MRMLLHLSLLALGAAYVYAIPTEIPTSALVKETLALLSTHRTLLIANETL

RIPVPVHKNHQLCTEEIFQGIGTLESQTVQGGTVERLFKNLSLIKKYIDG

QKKKCGEERRRVNQFLDYLQEFLGVMNTEWIIES*HHHHHH*

Note: The portion in italics represents His6-tag;

-continued

The amino acid sequence for cyno IL-5 with his-tag

SEQ ID NO: 2

MRMLLHLSLLALGAAYVYAIPTEIPASALVKETLALLSTHRTLLIANETL

RIPVPVHKNHQLCTEEIFQGIGTLESQTVQGGTVERLFKNLSLIKKYIGG

QKKKCGEERRRVNQFLDYLQEFLGVMNTEWIIES*HHHHHH*

Note: The portion in italics represents His6-tag.

The amino acid sequence for mouse IL-5 with his-tag

SEQ ID NO: 3

MEIPMSTVVKETLTQLSAHRALLTSNETMRLPVPTHKNHQLCIGEIFQGL

DILKNQTVRGGTVEMLFQNLSLIKKYIDRQKEKCGEERRRTRQFLDYLQE

FLGVMSTEWAMEG*HHHHHH*

Note: The portion in italics represents His6-tag.

The amino acid sequence for rat IL-5 with his-tag

SEQ ID NO: 4

MEIPMSTVVKETLIQLSTHRALLTSNETMRLPVPTHKNHQLCIGEIFQGL

DILKNQTVRGGTVEILFQNLSLIKKYIDGQKEKCGEERRKTRHFLDYLQE

FLGVMSTEWAMEV*HHHHHH*

Note: The portion in italics represents His6-tag.

The amino acid sequence for human IL-5α receptor fused to human Fc fragment

SEQ ID NO: 5

DLLPDEKISLLPPVNFTIKVTGLAQVLLQWKPNPDQEQRNVNLEYQVKIN

APKEDDYETRITESKCVTILHKGFSASVRTILQNDHSLLASSWASAELHA

PPGSPGTSIVNLTCTTNTTEDNYSRLRSYQVSLHCTWLVGTDAPEDTQYF

LYYRYGSWTEECQEYSKDTLGRNIACWFPRTFILSKGRDWLAVLVNGSSK

HSAIRPFDQLFALHAIDQINPPLNVTAEIEGTRLSIQWEKPVSAFPIHCF

DYEVKIHNTRNGYLQIEKLMTNAFISIIDDLSKYDVQVRAAVSSMCREAG

LWSEWSQPIYVGNDEHKPLREWIEGRMD*EPKSCDKTHTCPPCPAPELLGG*

*PSVFLFPPKPKDTLMISRTPEVTCVVVDVSHEDPEVKFNWYVDGVEVHNA*

*KTKPREEQYNSTYRVVSVLTVLHQDWLNGKEYKCKVSNKALPAPIEKTIS*

*KAKGQPREPQVYTLPPSRDELTKNQVSLTCLVKGFYPSDIAVEWESNGQP*

*ENNYKTTPPVLDSDGSFFLYSKLTVDKSRWQQGNVFSCSVMHEALHNHYT*

*QKSLSLSPGK*

Note: The portion in italics represents human IgG1-Fc-tag.

Example 2. Construction and Identification of Recombinant IL-5α Receptor and IL-5α/β Receptor Cell Lines To screen for functional antibodies, the present disclosure constructed CHO-S/IL-5α cell lines expressing IL-5α, and CHO-S/IL-5α/IL-5β cell lines expressing both IL-5α and IL-5β.

Specifically, the human IL-5α full-length gene (Q01344) was cloned into a mammalian cell expression vector pTargeT, the linearized plasmid was electro-transfected into CHO-S cells, and screened in the presence of G418 for 2 weeks, and then limited dilutions were performed twice. The IL-5α gene was detected on cell surface by FACS, and the CHO-S/IL-5α cell line with high IL-5α expression level was selected. On this basis, the linearized pcDNA3.1-IL-5β was electro-transfected, and screened in the presence of G418 and zeocin for 2 weeks, and then limited dilutions were performed twice. The IL-5α and IL-5β genes were detected on the cell surface by FACS, and CHO-S/IL-5α/IL-5β cell line with high expression level of IL-5α and IL-5ß was selected.

Example 3. Preparation of Anti-Human IL-5 Murine Monoclonal Antibody

Two doses of the recombinant protein rhIL-5-his, Freund's adjuvant CFA (Sigma, Lot #SLBQ1109V), and IFA (Sigma, Lot #SLBJ2845V) (100 g/50 g/50 g (high) and 25 g/12.5 g/12.5 g (low)) were used to immunize two groups of Balb/c mice (5 mice/group) and four groups of SJL mice (5 mice/group), respectively. The specific immune response to IL-5 was determined by detecting serum titer by ELISA, by ligand-receptor blocking assay and by inhibition assay of TF-1 proliferation. The mice with good specific immune response were selected and sacrificed; the spleen cells were collected and fused with myeloma cells.

The primary screening was carried out by ELISA binding assay against human IL-5. Once the hybridoma cells were transferred to a 24-well plate, the supernatants were screened again, by using ELISA binding assay against human, cynomolgus monkey and mouse IL-5, ELISA-based receptor blocking assay against IL-5, and inhibition assay of TF-1 proliferation. After the positive clones were subjected to two rounds of sub-cloning, the hybridoma clones were obtained and were used for antibody production; and the obtained antibodies were purified by affinity chromatography.

The purified antibodies were subjected to: SEC-HPLC, detection of endotoxin content, Biacore affinity assay for various species IL-5, FACS-based receptor blocking assay against IL-5, inhibition assay of TF-1 proliferation, adhesion test of eosinophils, and efficacy evaluation in mouse model of asthma and neutralization model of guinea pig in vivo; the monoclonal hybridoma cell lines mAb1705, mAb1706, mAb1780, mAb1773 and mAb1779 showing favorable activity in vivo and in vitro were selected.

The process for cloning sequences from positive hybridoma was as follows: hybridoma cells at logarithmic growth phase were collected, RNA was extracted with Trizol (Invitrogen, Cat No. 15596-018) according to the kit instructions, PrimeScript™ Reverse Transcriptase Kit was used for reverse transcription (Takara, Cat No. 2680A). The cDNA obtained by reverse transcription was amplified by PCR using mouse Ig-Primer Set (Novagen, TB326 Rev. B0503) and then sequenced. The amino acid sequences corresponding to the heavy chain and the light chain variable region DNA sequences for mAb1705, mAb1706, mAb1780, mAb1773 and mAb1779 were obtained (the amino acid residues of VH/VL CDRs are determined and annotated by Kabat numbering criteria).

The sequence for mAb1705 murine heavy chain variable region

SEQ ID NO: 6

EVQLVESGGGLVQPGRSLKLSCTASGFTFSHYYMAWVRQAPKKGLEWVTS

ISYEGDITYYGDSVKGRFTISRDNAKSTLYLQMNSLRSEDTATYYCASQT

LRESFDYWGQGVMVTVSS

The sequence for mAb1705 murine light chain variable region

SEQ ID NO: 7

DIQMTQSPSSMSVSLGDRVTITCRASQDIANYLSWYQQKIARSPKLVIYG

TSNLEVGVPSRFSGSRSGSDYSLTINTLESEDTGIYFCLQDKEFPRTFGG

-continued

GTRLELK

The sequence for mAb1706 murine heavy chain variable region

SEQ ID NO: 8

EVQLVESGGGLVQPGRSLKLSCAASGFTFSHYYMAWVRQAPKKGLEWVTS

INYEGNSAYYGDSVKGRFTISRDNAKSTLYLQMDSLRSEDTATYYCATET

LRESLDYWGQGVMVTVSS

The sequence for mAb1706 murine light chain variable region

SEQ ID NO: 9

DIQMTQSPSSMSVSLGDRVTITCRASQDIGNYLSWYQQKLGKSPKLMIHS

ASNLEVGVPSRFSGSRSGSDYSLTINTLESEDPGIYFCLQHKQFPRTFGG

GTKLELK

The sequence for mAb1780 murine heavy chain variable region

SEQ ID NO: 10

QVKLLQSGAALVKPGDSVKMSCKASDYTFTEYLIHWVKQSQGRSLEWIGY

INPYSGGTVYNEKFKSKATLTVDKFSSTAYMEFRRLTFEDSAIYYCARDG

GYSDPLDYWGQGVMVTVSS

The sequence for mAb1780 murine light chain variable region

SEQ ID NO: 11

DTVLTQSPALAVSPGERVSISCRASEGLTSYMHWYQQKPGQQPKWYKASN

LASGVPARFSGSGSGTDFTLTIDPVEADDAATYFCQQNWNDPWTFGGGTK

LELK

The sequence for mAb1773 murine heavy chain variable region

SEQ ID NO: 12

EVQLQQSLAELVRPGASVTLSCTASGFNIKNTYIHWVKQRPEQGLEWIGR

IDPANGDTKHGPKFQGKATITADTSSNTAYLQFSSLTSEDTAIYYCFRYG

IYPDHWGQGTPLTVSS

The sequence for mAb1773 murine light chain variable region

SEQ ID NO: 13

QIVLTQSPALMSASPGEKVTMTCSASSSVNYIYWYQQKPRSSPKPWIYLT

ATLASGVPARFSGSGSGTSFSLTISRMEAEDAATYYCQQWNSYPYTFGGG

TKLEIE

The sequence for mAb1779 murine heavy chain variable region

SEQ ID NO: 14

QVKLLQSGAALVKPGDSVKMSCKASGYTFTDYIIHWVKQSHGKSLEWIGY

FNPNSGGSNYNENFKRKATLTADKSSSTAYLEFSRVTSEDSAIYYCGRRI

AWDHWYFDFWGPGTMVTVSS

The sequence for mAb1779 murine light chain variable region

SEQ ID NO: 15

DIQMTQSPASLSASLGETVSIECLASEGISNDVAWYQQKSGRSPQLLVYA

ASRLQDGVPSRFSGSGSGTRYFFKISGMQPEDEADYFCQQGYKTPLTFGS

GTKLEIK.

SEQ ID NO: 15.

The CDR sequences of light and heavy chain for each antibody are shown in Table 1.

TABLE 1

The sequences for CDR regions in heavy chain and light chain of each antibody

| Antibody | heavy chain | | light chain | |
|---|---|---|---|---|
| mAb1705 | HCDR1 | HYYMA SEQ ID NO: 16 | LCDR1 | RASQDIANYLS SEQ ID NO: 19 |
| | HCDR2 | SISYEGDITYYGD SVKG SEQ ID NO: 17 | LCDR2 | GTSNLEV SEQ ID NO: 20 |
| | HCDR3 | QTLRESFDY SEQ ID NO: 18 | LCDR3 | LQDKEFPRT SEQ ID NO: 21 |
| mAb1706 | HCDR1 | HYYMA SEQ ID NO: 22 | LCDR1 | RASQDIGNYLS SEQ ID NO: 25 |
| | HCDR2 | SINYEGNSAYYGD SVKG SEQ ID NO: 23 | LCDR2 | SASNLEV SEQ ID NO: 26 |
| | HCDR3 | ETLRESLDY SEQ ID NO: 24 | LCDR3 | LQHKQFPRT SEQ ID NO: 27 |
| mAb1780 | HCDR1 | EYLIH SEQ ID NO: 28 | LCDR1 | RASEGLTSYMH SEQ ID NO: 31 |
| | HCDR2 | YINPYSGGTVYNE KFKS SEQ ID NO: 29 | LCDR2 | KASNLAS SEQ ID NO: 32 |
| | HCDR3 | DGGYSDPLDY SEQ ID NO: 30 | LCDR3 | QQNWNDPWT SEQ ID NO: 33 |
| mAb1773 | HCDR1 | NTYIR SEQ ID NO: 34 | LCDR1 | SASSSVNYIY SEQ ID NO: 37 |
| | HCDR2 | RIDPANGDTKHGP KFQG SEQ ID NO: 35 | LCDR2 | LTATLAS SEQ ID NO: 38 |
| | HCDR3 | YGIYPDH SEQ ID NO: 36 | LCDR3 | QQWNSYPYT SEQ ID NO: 39 |
| mAb1779 | HCDR1 | DYIIH SEQ ID NO: 40 | LCDR1 | LASEGISNDVA SEQ ID NO: 43 |
| | HCDR2 | YFNPNSGGSNYNE NFKR SEQ ID NO: 41 | LCDR2 | AASRLQD SEQ ID NO: 44 |
| | HCDR3 | RIAWDHWYFDF SEQ ID NO: 42 | LCDR3 | QQGYKTPLT SEQ ID NO: 45 |

The detection result of activity by Biacore can be found in Table 2.

TABLE 2

In vitro activity of IL-5 murine antibody

| Antibody | HuIL-5 affinity (KD (M)) |
|---|---|
| mAb1705 | 7.27E−11 |
| mAb1706 | 3.83E−11 |
| mAb1780 | 8.99E−11 |
| mAb1773 | 1.29E−10 |
| mAb1779 | 4.58E−10 |

The results show that the murine antibodies of the present disclosure have high affinity for the antigen.

Example 4. Purification of IL-5 Related Recombinant Proteins, and Purification of Hybridoma Antibodies and Recombinant Antibodies 4.1 Purification Steps of IL-5-Flag-his Recombinant Protein:

The samples were centrifuged at high speed to remove impurities and concentrated to an appropriate volume. The NI-NTA affinity column (QIAGEN, Cat No. 30721) was equilibrated with PBS, and washed with 2-5 folds of column volume. After removing impurities, the cell expression supernatant sample was loaded onto the column. The column was washed with PBS, until the A280 reading was decreased to baseline. The column was washed with PBS to remove the contaminating proteins, the sample was collected. The target protein was eluted successively with washing buffer (20 mM imidazole) and elution buffer (300 mM imidazole), and the elution peaks were collected.

The collected eluate was further purified by ion exchange (Hiload 16/600 superdex 200 column). The column was equilibrated with about 2-column volumes of PBS to ensure pH at 7.4. The elution buffer comprising the identified target protein was concentrated and loaded, the sample was collected and verified by SDS-PAGE and LC-MS identification, and aliquoted for use.

4.2 Purification of Hybridoma Expressed Antibody and Fc Fusion Protein

The cell expression supernatant sample was centrifuged at high speed to remove impurities. The hybridoma expression supernatant was purified with Protein G column, and the Fc fusion protein expression supernatant was purified with Protein A column. The column was washed with PBS until the A280 reading was decreased to baseline. The target protein was eluted with 100 mM acetic acid pH 3.0, and neutralized with 1M Tris-HCl, pH 8.0. After the eluted sample was properly concentrated, the sample was further purified by PBS-equilibrated gel chromatography Superdex200 (GE), and the peak without aggregates was collected and then aliquoted for use.

Example 5. Humanization Design of Anti-Human IL-5 Monoclonal Antibody

The humanization of the murine anti-human IL-5 monoclonal antibody was carried out as disclosed in many references in the art. In brief, the constant regions of the murine antibody were replaced with human constant regions, and the CDRs of the murine antibody were grafted onto FR human template having the highest homology, and back-mutation was performed on the amino acids in the FR region.

By aligning against the IMGT human antibody heavy and light chain variable region germline gene database, the heavy chain and the light chain variable region germlines that have high identity with each of amino acid sequences of mAb-1705, mAb-1706, mAb1780, mAb1773 and mAb1779 antibodies were selected as templates, the CDRs of the murine antibody were grafted onto the corresponding human template to form a variable region in the order of FR1-CDR1-FR2-CDR2-FR3-CDR3-FR4. The amino acid residues were determined and annotated by Kabat numbering criteria.

The selection of human FR regions and amino acid back-mutation

On the basis of typical structure of the obtained murine antibody VH/VL CDR, the light chain variable region (VL) and the heavy chain variable region (VH) homologous sequences were retrieved from human germline database, and ranked according to FR homology (from high to low); the germline with the highest FR homology was selected as main template. The CDR regions of the murine antibody were grafted onto the human template, and then the FR residues were subjected to mutation, and the amino acid residues were optimized to obtained the final humanized molecules.

5.1 the Selection of Humanized Framework for Hybridoma Clone mAb1705

For h1705, IGHV3-23*04 was selected as the template for VH, and IGKV1-12*01 was selected as the template for VL. The CDRs of mAb1705 were grafted onto the human template; the embedded residues and residues which directly interacted with CDR region (found through software) were subjected to back-mutation. Various light chain and heavy chain variable regions of the humanized antibodies were obtained, as shown in Table 3.

TABLE 3

| Template selection and back-mutation design for h1705 | | | |
|---|---|---|---|
| h1705_VL | | h1705_VH | |
| h1705_VL.1 | Grafted | h1705_VH.1 | Grafted |
| h1705_VL.1A | A43S, G66R | h1705_VH.1A | K98S |
| h1705_VL.1B | A43S, L47V, G66R, T69S, F71Y, Y87F | h1705_VH.1B | S49T, V93T, K98S |

Note:
"Grafted" represents that the murine antibody CDRs were grafted onto the human germline FR region sequence. For example, according to the natural numbering of amino acid sequence, A43S represents that A at position 43 of "grafted" was mutated back to S.

TABLE 4

| Combination of h1705 humanized antibody heavy and light chain variable regions | | | |
|---|---|---|---|
| | h1705_VH.1 | h1705_VH.1A | h1705_VH.1B |
| h1705_VL.1 | h1705-003 | h1705-004 | h1705-005 |
| h1705_VL.1A | h1705-006 | h1705-007 | h1705-008 |
| h1705_VL.1B | h1705-009 | h1705-010 | h1705-011 |

Note: This table shows the sequences obtained by various combinations of mutations. As indicated by h1705-007, the humanized murine antibody h1705-007 comprises two mutants, i.e., light chain h1705_VL.1A and heavy chain h1705_VH.1A, and so forth.

The specific sequences of the variable regions of the humanized antibody h1705 are as follows:

```
>h1705_VL.1
                                        (SEQ ID NO: 46)
DIQMTQSPSSVSASVGDRVTITCRASQDIANYLSWYQQKPGKAPKLLIYG

TSNLEVGVPSRFSGSGSGTDFTLTISSLQPEDFATYYCLQDKEFPRTFGG

GTKVEIK

>h1705_VL.1A
                                        (SEQ ID NO: 47)
DIQMTQSPSSVSASVGDRVTITCRASQDIANYLSWYQQKPGKSPKLLIYG

TSNLEVGVPSRFSGSRSGTDFTLTISSLQPEDFATYYCLQDKEFPRTFGG

GTKVEIK

>h1705_VL.1B
                                        (SEQ ID NO: 48)
DIQMTQSPSSVSASVGDRVTITCRASQDIANYLSWYQQKPGKSPKLVIYG

TSNLEVGVPSRFSGSRSGSDYTLTISSLQPEDFATYFCLQDKEFPRTFGG

GTKVEIK

>h1705_VH.1
                                        (SEQ ID NO: 49)
EVQLVESGGGLVQPGGSLRLSCAASGFTFSHYYMAWVRQAPGKGLEWVSS

ISYEGDITYYGDSVKGRFTISRDNSKNTLYLQMNSLRAEDTAVYYCAKQT

LRESFDYWGQGTLVTVSS
```

-continued

```
>h1705_VH.1A
                                        (SEQ ID NO: 50)
EVQLVESGGGLVQPGGSLRLSCAASGFTFSHYYMAWVRQAPGKGLEWVSS

ISYEGDITYYGDSVKGRFTISRDNSKNTLYLQMNSLRAEDTAVYYCASQT

LRESFDYWGQGTLVTVSS

>h1705_VH.1B
                                        (SEQ ID NO: 51)
EVQLVESGGGLVQPGGSLRLSCAASGFTFSHYYMAWVRQAPGKGLEWVTS

ISYEGDITYYGDSVKGRFTISRDNSKNTLYLQMNSLRAEDTATYYCASQT

LRESFDYWGQGTLVTVSS.
```

Each of the light chain variable regions as described above was combined with the light chain constant region to form a light chain sequence, and each of the heavy chain variable regions was combined with the heavy chain constant region to form a heavy chain sequence. The exemplary humanized antibody constant region sequences are shown below:

```
>heavy chain IgG1 constant region:
                                          SEQ ID NO: 52
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLYITREPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
Note: the underlined portion represents M252Y,
S254T, T256E mutations.

light chain kappa constant region:
                                          SEQ ID NO: 53
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.
```

5.2 the Selection of Humanized Framework for Hybridoma Clone mAb1706

For h1706, IGHV3-23*04 was selected as the template for VH, and IGKV1-12*01 was selected as the template for VL. The CDRs of murine antibody mAb1706 were grafted onto the selected humanized template; the FR amino acids were subjected to back-mutation. The light chain and heavy chain variable regions of the humanized antibodies were obtained, as shown in Table 5.

TABLE 5

| Template selection and back-mutation design for h1706 | | | |
|---|---|---|---|
| h1706_VL | | h1706_VH | |
| h1706_VL.1 | Grafted | h1706_VH.1 | Grafted |
| h1706_VL.1A | A43S | h1706_VH.1A | K98T |
| h1706_VL.1B | A43S, L47M, F71Y, Y87F | h1706_VH.1B | S49T, V93T, K98T |

Note:
"Grafted" represents that the murine antibody CDRs were grafted onto the human germline FR region. For example, according to the natural numbering of amino acid sequence, A43S represents that A at position 43 of "grafted" was mutated back to S.

Note: "Grafted" represents that the murine antibody CDRs were grafted onto the human germline FR region. For example, according to the natural numbering of amino acid sequence, A43S represents that A at position 43 of "grafted" was mutated back to S.

The designed humanized molecules were combined to form different antibodies shown in the following table, as shown in Table 6.

TABLE 6

| Combination of h1706 humanized antibody heavy and light chain variable regions | | | |
|---|---|---|---|
| | h1706_VH.1 | h1706_VH.1A | h1706_VH.1B |
| h1706_VL.1 | h1706-002 | h1706-003 | h1706-004 |
| h1706_VL.1A | h1706-005 | h1706-006 | h1706-007 |
| h1706_VL.1B | h1706-008 | h1706-009 | h1706-010 |

The specific sequences of the variable regions of the h1706 humanized antibody are as follows:

```
>h1706_VL.1
                                           (SEQ ID NO: 54)
DIQMTQSPSSVSASVGDRVTITCRASQDIGNYLSWYQQKPGKAPKLLIYS

ASNLEVGVPSRFSGSGSGTDFTLTISSLQPEDFATYYCLQHKQFPRTFGG

GTKVEIK

>h1706_VL.1A
                                           (SEQ ID NO: 55)
DIQMTQSPSSVSASVGDRVTITCRASQDIGNYLSWYQQKPGKSPKLLIYS

ASNLEVGVPSRFSGSGSGTDFTLTISSLQPEDFATYYCLQHKQFPRTFGG

GTKVEIK

>h1706_VL.1B
                                           (SEQ ID NO: 56)
DIQMTQSPSSVSASVGDRVTITCRASQDIGNYLSWYQQKPGKSPKLMIYS

ASNLEVGVPSRFSGSGSGTDYTLTISSLQPEDFATYFCLQHKQFPRTFGG

GTKVEIK

>h1706_VH.1
                                           (SEQ ID NO: 57)
EVQLVESGGGLVQPGGSLRLSCAASGFTFSHYYMAWVRQAPGKGLEWVSS

INYEGNSAYYGDSVKGRFTISRDNSKNTLYLQMNSLRAEDTAVYYCAKET

LRESLDYWGQGTMVTVSS
```

-continued

```
>h1706_VH.1A
                                           (SEQ ID NO: 58)
EVQLVESGGGLVQPGGSLRLSCAASGFTFSHYYMAWVRQAPGKGLEWVSS

INYEGNSAYYGDSVKGRFTISRDNSKNTLYLQMNSLRAEDTAVYYCATET

LRESLDYWGQGTMVTVSS

>h1706_VH.1B
                                           (SEQ ID NO: 59)
EVQLVESGGGLVQPGGSLRLSCAASGFTFSHYYMAWVRQAPGKGLEWVTS

INYEGNSAYYGDSVKGRFTISRDNSKNTLYLQMNSLRAEDTATYYCATET

LRESLDYWGQGTMVTVSS.
```

Each of the light chain variable regions as described above was combined with the light chain constant region to form a light chain sequence. Each of the heavy chain variable regions was combined with the heavy chain constant region to form a heavy chain sequence.

5.3 the Selection of Humanized Framework for Hybridoma Clone mAb1780

For h1780, IGHV1-2*02 was selected as the template for VH, and IGKV3-11*01 was selected as the template for VL. The CDRs of murine antibody mAb1780 were grafted onto the selected humanized template; the FR amino acids were subjected to back-mutation. The light chain and heavy chain variable regions of the humanized antibodies were obtained, as shown in Table 7.

TABLE 7

| Template selection and back-mutation design for h1780 | | | |
|---|---|---|---|
| h1780_VL | | h1780_VH | |
| h1780_VL.1 | Grafted | h1780_VH.1 | Grafted |
| h1780_VL.1A | E1D, I2T | h1780_VH.1A | M70L, R72V, T74K |
| h1780_VL.1B | E1D, I2T, I57V, V84T, Y86F | h1780_VH.1B | M48I, V68A, M70L, R72V, T74K, L83F |
| | | h1780_VH.1C | R38K, M48I, R67K, V68A, M70L, R72V, T74K, L83F |

Note: "Grafted" represents that the murine antibody CDRs were grafted onto the human germline FR region. For example, according to the natural numbering of amino acid sequence, E1D represents that E at position 1 of "grafted" was mutated back to D.

The designed humanized molecules were combined to form different molecules shown in the following table, as shown in Table 8.

TABLE 8

| Combination of h1780 humanized antibody heavy and light chain variable regions | | | | |
|---|---|---|---|---|
| | h1780_VH.1 | h1780_VH.1A | h1780_VH.1B | h1780_VH.1C |
| h1780_VL.1 | h1780-007 | h1780-008 | h1780-009 | h1780-010 |
| h1780_VL.1A | h1780-011 | h1780-012 | h1780-013 | h1780-014 |
| h1780_VL.1B | h1780-015 | h1780-016 | h1780-017 | h1780-018 |

The specific sequences of the variable regions of the h1780 humanized antibody are as follows:

```
>h1780_VL.1
                                          (SEQ ID NO: 60)
EIVLTQSPATLSLSPGERATLSCRASEGLTSYMHWYQQKPGQAPRLLIYK

ASNLASGIPARFSGSGSGTDFTLTISSLEPEDFAVYYCQQNWNDPWTFGG

GTKVEIK

>h1780_VL.1A
                                          (SEQ ID NO: 61)
DTVLTQSPATLSLSPGERATLSCRASEGLTSYMHWYQQKPGQAPRLLIYK

ASNLASGIPARFSGSGSGTDFTLTISSLEPEDFAVYYCQQNWNDPWTFGG

GTKVEIK

>h1780_VL.1B
                                          (SEQ ID NO: 62)
DTVLTQSPATLSLSPGERATLSCRASEGLTSYMHWYQQKPGQAPRLLIYK

ASNLASGVPARFSGSGSGTDFTLTISSLEPEDFATYFCQQNWNDPWTFGG

GTKVEIK

>h1780_VH.1
                                          (SEQ ID NO: 63)
EVQLVQSGAEVKKPGASVKVSCKASGYTFTEYLIHWVRQAPGQGLEWMGY

INPYSGGTVYNEKFKSRVTMTRDTSISTAYMELSRLRSDDTAVYYCARDG

GYSDPLDYWGQGTMVTVSS

>h1780_VH.1A
                                          (SEQ ID NO: 64)
EVQLVQSGAEVKKPGASVKVSCKASGYTFTEYLIHWVRQAPGQGLEWMGY

INPYSGGTVYNEKFKSRVTLTVDKSISTAYMELSRLRSDDTAVYYCARDG

GYSDPLDYWGQGTMVTVSS

>h1780_VH.1B
                                          (SEQ ID NO: 65)
EVQLVQSGAEVKKPGASVKVSCKASGYTFTEYLIHWVRQAPGQGLEWIGY

INPYSGGTVYNEKFKSRATLTVDKSISTAYMEFSRLRSDDTAVYYCARDG

GYSDPLDYWGQGTMVTVSS

>h1780_VH.1C
                                          (SEQ ID NO: 66)
EVQLVQSGAEVKKPGASVKVSCKASGYTFTEYLIHWVKQAPGQGLEWIGY

INPYSGGTVYNEKFKSKATLTVDKSISTAYMEFSRLRSDDTAVYYCARDG

GYSDPLDYWGQGTMVTVSS.
```

Each of the light chain variable regions as described above was combined with the light chain constant region to form a light chain sequence. Each of the heavy chain variable regions was combined with the heavy chain constant region to form a heavy chain sequence.

5.4 the Selection of Humanized Framework for Hybridoma Clone mAb1773

For h1773, IGHV3-73*01 was selected as the template for VH, and IGKV1-39*01 was selected as the template for VL. The CDRs of murine antibody mAb1773 were grafted onto the selected humanized template; the amino acids were subjected to back-mutation. The light chain and heavy chain variable regions of the humanized antibodies were obtained, as shown in Table 9. In addition, N in h1773 HCDR2 (RIDPANGDTK HGPKFQG) was mutated into V (i.e. N55V) to form heavy chain variable region HCDR2 variant (the sequence of mutated HCDR2 is as shown in SEQ ID NO: 82: RIDPAVGDTKHGPKFQG).

TABLE 9

Template selection and back-mutation design for h1773

| h1773_VL | | h1773_VH | |
|---|---|---|---|
| h1773_VL.1 | Grafted | h1773_VH.1 | Grafted |
| h1773_VL.1A | M4L, A42S, L45P, L46W | h1773_VH.1A | F291, R72A, T97F + N55V |
| | | h1773_VH.1B | F29I, R38K, V48I, R72A, T97F + N55V |

Note:
"Grafted" represents that the murine antibody CDRs were grafted onto the human germline FR region. For example, according to the natural numbering of amino acid sequence, M4L represents that M at position 4 of "grafted" was mutated back to L.

The designed humanized molecules were combined to form different molecules shown in the following table, as shown in Table 10.

TABLE 10

Combination of h1773 humanized antibody heavy and light chain variable regions

| | h1773_VH.1 | h1773_VH.1A | h1773_VH. 1B |
|---|---|---|---|
| h1773_VL.1 | h1773-002 | h1773-003 | h1773-004 |
| h1773_VL.1A | h1773-005 | h1773-006 | h1773-007 |

The specific sequences of the variable regions of the h1773 humanized antibody are as follows:

```
>h1773_VL.1
                                          (SEQ ID NO: 67)
DIQMTQSPSSLSASVGDRVTITCSASSSVNYIYWYQQKPGKAPKWYLTAT

LASGVPSRFSGSGSGTDFTLTISSLQPEDFATYYCQQWNSYPYTFGGGTK

VEIK

>h1773_VL.1A
                                          (SEQ ID NO: 68)
DIQLTQSPSSLSASVGDRVTITCSASSSVNYIYWYQQKPGKSPKPWIYLT

ATLASGVPSRFSGSGSGTDFTLTISSLQPEDFATYYCQQWNSYPYTFGGG

TKVEIK

>h1773_VH.1
                                          (SEQ ID NO: 69)
EVQLVESGGGLVQPGGSLKLSCAASGFTFSNTYIHWVRQASGKGLEWVGR

IDPAVGDTKHGPKFQGRFTISRDDSKNTAYLQMNSLKTEDTAVYYCTRYG

IYPDHWGQGTLVTVSS

>h1773_VH.1A
                                          (SEQ ID NO: 70)
EVQLVESGGGLVQPGGSLKLSCAASGFTISNTYIHWVRQASGKGLEWVGR

IDPAVGDTKHGPKFQGRFTISADDSKNTAYLQMNSLKTEDTAVYYCFRYG

IYPDHWGQGTLVTVSS

>h1773_VH.1B
                                          (SEQ ID NO: 71)
EVQLVESGGGLVQPGGSLKLSCAASGFTISNTYIHWVKQASGKGLEWIGR

IDPAVGDTKHGPKFQGRFTISADDSKNTAYLQMNSLKTEDTAVYYCFRYG

IYPDHWGQGTLVTVSS.
```

Each of the light chain variable regions as described above was combined with the light chain constant region sequence as shown in SEQ ID NO: 53 to form the final complete light chain sequence. Each of the heavy chain variable regions was combined with the heavy chain constant region as shown in SEQ ID NO: 52 to form the final complete heavy chain sequence.

5.5 the Selection of Humanized Framework for Hybridoma Clone mAb1779

For h1779, IGHV1-2*02 was selected as the template for VH, and IGKV1-33*01 was selected as the template for VL. The CDRs of murine antibody h1779 were grafted onto the selected humanized template; the amino acids were subjected to back-mutation. The light chain and heavy chain variable regions of the humanized antibodies were obtained, as shown in Table 11.

TABLE 11

Template selection and back-mutation design for h1779

| h1779_VL | | h1779_VH | |
|---|---|---|---|
| h1779_VL.1 | Grafted | h1779_VH.1 | Grafted + D89E |
| h1779_VL.1A | A43S | h1779_VH.1A | R72A,T74K + D89E |
| h1779_VL.1B | A43S, I48V, F71Y | h1779_VH.1B | M48I, V68A, R72A, T74K + D89E |
| | | h1779_VH.1C | M48I, V68A, R72A, T74K, M81L, L83F + D89E |
| | | h1779_VH.1D | R38K, M48I, R67K, V68A, R72A, T74K, M81L, L83F + D89E |

Note:
"Grafted" represents that the murine antibody CDRs were grafted onto the human germline FR region. For example, according to the natural numbering of amino acid sequence, A43S represents that A at position 43 of "grafted" was mutated back to S.

The designed humanized molecules were combined to form different molecules shown in the following table, as shown in Table 12.

TABLE 12

Combination of h1779 humanized antibody heavy and light chain variable regions

| | h1779_VH.1 | h1779_VH.1A | h1779_VH.1B | h1779_VH.1C | h1779_VH.1D |
|---|---|---|---|---|---|
| h1779_VL.1 | h1779-005 | h1779-006 | h1779-007 | h1779-008 | h1779-009 |
| h1779_VL.1A | h1779-010 | h1779-011 | h1779-012 | h1779-013 | h1779-014 |
| h1779_VL.1B | h1779-015 | h1779-016 | h1779-017 | h1779-018 | h1779-019 |

The specific sequences of the variable regions of the h1779 humanized antibody are as follows:

```
>h1779_VL.1
                                        (SEQ ID NO: 72)
DIQMTQSPSSLSASVGDRVTITCLASEGISNDVAWYQQKPGKAPKLLIYA

ASRLQDGVPSRFSGSGSGTDFTFTISSLQPEDIATYYCQQGYKTPLTFGQ

GTKLEIK

>h1779_VL.1A
                                        (SEQ ID NO: 73)
DIQMTQSPSSLSASVGDRVTITCLASEGISNDVAWYQQKPGKSPKLLIYA

ASRLQDGVPSRFSGSGSGTDFTFTISSLQPEDIATYYCQQGYKTPLTFGQ

GTKLEIK

>h1779_VL.1B
                                        (SEQ ID NO: 74)
DIQMTQSPSSLSASVGDRVTITCLASEGISNDVAWYQQKPGKSPKLLVYA

ASRLQDGVPSRFSGSGSGTDYTFTISSLQPEDIATYYCQQGYKTPLTFGQ

GTKLEIK
```

-continued

```
>h1779_VH.1
                                        (SEQ ID NO: 75)
EVQLVQSGAEVKKPGASVKVSCKASGYTFTDYIIHWVRQAPGQGLEWMGY

FNPNSGGSNYNENFKRRVTMTRDTSISTAYMELSRLRSEDTAVYYCARRI

AWDHWYFDFWGQGTMVTVSS

>h1779_VH.1A
                                        (SEQ ID NO: 76)
EVQLVQSGAEVKKPGASVKVSCKASGYTFTDYIIHWVRQAPGQGLEWMGY

FNPNSGGSNYNENFKRRVTMTADKSISTAYMELSRLRSEDTAVYYCARRI

AWDHWYFDFWGQGTMVTVSS

>h1779_VH.1B
                                        (SEQ ID NO: 77)
EVQLVQSGAEVKKPGASVKVSCKASGYTFTDYIIHWVRQAPGQGLEWIGY

FNPNSGGSNYNENFKRRATMTADKSISTAYMELSRLRSEDTAVYYCARRI

AWDHWYFDFWGQGTMVTVSS

>h1779_VH.1C
                                        (SEQ ID NO: 78)
EVQLVQSGAEVKKPGASVKVSCKASGYTFTDYIIHWVRQAPGQGLEWIGY

FNPNSGGSNYNENFKRRATMTADKSISTAYLEFSRLRSEDTAVYYCARRI

AWDHWYFDFWGQGTMVTVSS
```

-continued

```
>h1779_VH.1D
                                        (SEQ ID NO: 79)
EVQLVQSGAEVKKPGASVKVSCKASGYTFTDYIIHWVKQAPGQGLEWIGY

FNPNSGGSNYNENFKRKATMTADKSISTAYLEFSRLRSEDTAVYYCARRI

AWDHWYFDFWGQGTMVTVSS.
```

Each of the light chain variable regions as described above was combined with the light chain constant region sequence as shown in SEQ ID NO: 53 to form a light chain sequence. Each of the heavy chain variable regions was combined with the heavy chain constant region as shown in SEQ ID NO: 52 to form a heavy chain sequence.

The full-length sequences of the exemplary humanized antibodies are as follows:

```
h1705-008 heavy chain:
                                        SEQ ID NO: 83
EVQLVESGGGLVQPGGSLRLSCAASGFTFSHYYMAWVRQAPGKGLEWVTS

ISYEGDITYYGDSVKGRFTISRDNSKNTLYLQMNSLRAEDTATYYCASQT

LRESFDYWGQGTLVTVSSASTKGPSVFPLAPSSKSTSGGTAALGCLVKDY
```

-continued

FPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKD
TLYITREPEVTCVVVDVSHEDPEVKFNWYVDGVEVHNAKTKPREEQYNST
YRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK h1705-008 light chain:

SEQ ID NO: 84
DIQMTQSPSSVSASVGDRVTITCRASQDIANYLSWYQQKPGKSPKLLIYG
TSNLEVGVPSRFSGSRSGTDFTLTISSLQPEDFATYYCLQDKEFPRTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC h1706-009 heavy chain:

SEQ ID NO: 85
EVQLVESGGGLVQPGGSLRLSCAASGFTFSHYYMAWVRQAPGKGLEWVSS
INYEGNSAYYGDSVKGRFTISRDNSKNTLYLQMNSLRAEDTAVYYCATET
LRESLDYWGQGTMVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKD
TLYITREPEVTCVVVDVSHEDPEVKFNWYVDGVEVHNAKTKPREEQYNST
YRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK h1706-009 light chain:

SEQ ID NO: 86
DIQMTQSPSSVSASVGDRVTITCRASQDIGNYLSWYQQKPGKSPKLMIYS
ASNLEVGVPSRFSGSGSGTDYTLTISSLQPEDFATYFCLQHKQFPRTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC h1780-017 heavy chain:

SEQ ID NO: 87
EVQLVQSGAEVKKPGASVKVSCKASGYTFTEYLIHWVRQAPGQGLEWIGY
INPYSGGTVYNEKFKSRATLTVDKSISTAYMEFSRLRSDDTAVYYCARDG
GYSDPLDYWGQGTMVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLYITREPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

-continued h1780-017 light chain:

SEQ ID NO: 88
DTVLTQSPATLSLSPGERATLSCRASEGLTSYMHWYQQKPGQAPRLLIYK
ASNLASGVPARFSGSGSGTDFTLTISSLEPEDFATYFCQQNWNDPWTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC h1773-007 heavy chain:

SEQ ID NO: 89
EVQLVESGGGLVQPGGSLKLSCAASGFTISNTYIHWVKQASGKGLEWIGR
IDPAVGDTKHGPKFQGRFTISADDSKNTAYLQMNSLKTEDTAVYYCFRYG
IYPDHWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
YITREPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK h1773-007 light chain:

SEQ ID NO: 90
DIQLTQSPSSLSASVGDRVTITCSASSSVNYIYWYQQKPGKSPKPWIYLT
ATLASGVPSRFSGSGSGTDFTLTISSLQPEDFATYYCQQWNSYPYTFGGG
TKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC h1779-014 heavy chain:

SEQ ID NO: 91
EVQLVQSGAEVKKPGASVKVSCKASGYTFTDYIIHWVKQAPGQGLEWIGY
FNPNSGGSNYNENFKRKATMTADKSISTAYLEFSRLRSEDTAVYYCARRI
AWDHWYFDFWGQGTMVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLYITREPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK h1779-014 light chain:

SEQ ID NO: 92
DIQMTQSPSSLSASVGDRVTITCLASEGISNDVAWYQQKPGKSPKLLVYA
ASRLQDGVPSRFSGSGSGTDYTFTISSLQPEDIATYYCQQGYKTPLTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC;

The antibody Hu39D10 against IL5 in WO2012083370A1 was used as a positive control in the present disclosure, and the heavy chain and light chain sequences thereof are shown in SEQ ID NO: 80 and SEQ ID NO: 81, respectively.

```
The sequence for Hu39D10 heavy chain
                                        SEQ ID NO: 80
EVQLVESGGGLVQPGGSLRLSCAVSGLSLTSNSVNWIRQAPGKGLEWVGL

IWSNGDTDYNSAIKSRFTISRDTSKSTVYLQMNSLRAEDTAVYYCAREYY

GYFDYWGQGTLVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

The sequence for Hu39D10 light chain
                                        SEQ ID NO: 81
DIQMTQSPSSLSASVGDRVTITCLASEGISSYLAWYQQKPGKAPKLLIYG

ANSLQTGVPSRFSGSGSATDYTLTISSLQPEDFATYYCQQSYKFPNTFGQ

GTKVEVKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

Example 6. Preparation of Recombinant Chimeric Antibody and Humanized Antibody 1. Molecular Cloning of Recombinant Chimeric Antibody After the positive antibody molecules were obtained by screening hybridomas, the gene sequences encoding variable region were obtained by sequencing. The forward and reverse primers were designed on the basis of the obtained sequences, and the sequenced gene was used as a template to construct each antibody VH/VK gene fragment by PCR, and then inserted into the expression vector pHr (having signal peptide and hIgG1/hkappa constant region gene (CH1-Fc/CL) fragment) by homologous recombination to construct a recombinant chimeric antibody full-length expression plasmid VH-CH1-Fc-pHr/VL-CL-pHr, so as to obtain five chimeric antibodies Ch1705, Ch1706, Ch1780, Ch1773 and Ch1779.

2. Molecular Cloning of Humanized Antibodies

Humanized antibody sequence was subjected to codon optimization, then the coding gene sequence with human codon-preference was obtained; primers were designed to construct each antibody VH/VK gene fragment by PCR, which was then inserted into the expression vector pHr (having signal peptide and hIgG1/hkappa constant region gene (CH1-Fc/CL) fragment) by homologous recombination to construct a humanized antibody full-length expression plasmid VH-CH1-Fc-pHr/VL-CL-pHr.

3. Expression and Purification of Recombinant Chimeric Antibody and Humanized Antibody The plasmid expressing the antibody light or heavy chain was separately transfected into HEK293E cells. 6 days later, the expression supernatant was collected, centrifuged at high speed to remove impurities, and purified with protein A column. The column was washed with PBS until the A280 reading was decreased to baseline. The target protein was eluted with acidic elution buffer, pH3.0-pH3.5 and neutralized with 1M Tris-HCl, pH 8.0-9.0. The eluted sample was appropriately concentrated, and was further purified by gel chromatography Superdex200 (GE) pre-equilibrated with PBS to remove aggregates, monomer peaks were collected, and aliquoted for use.

The following test methods were used to verify the performance and beneficial effects of the antibodies of the present disclosure.

Biological Evaluation of Activity In Vitro

Test Example 1. The Binding of Murine IL-5 Antibody to IL-5 of Different Species by Biacore Assay The affinity of the murine IL-5 antibody to be tested with human IL-5 was measured by Biacore T200 (GE) instrument.

The protein A biosensor chip was used to affinity capture of the molecules to be tested, and then the antigen (recombinant human and cyno IL-5 prepared in Example 1) flowed through the surface of the chip, and the reaction signal was detected in real time with the Biacore T200 instrument to obtain the binding and dissociation curves. After the dissociation of each experimental cycle was completed, the biosensor chip was washed and regenerated with glycine-hydrochloric acid regeneration solution (pH 1.5). BIAevaluation version 4.1 GE software was used to fit the data against (1:1) Langmuir model, and the affinity value was obtained and shown in Table 13.

TABLE 13

Results of affinity of murine IL-5 antibodes with IL-5 of different species by BIAcore assay

| | KD (M) | | | | |
|---|---|---|---|---|---|
| Antigen | mAb1705 | mAb1706 | mAb1780 | mAb1773 | mAb1779 |
| human IL-5 | 7.27E−11 | 3.83E−11 | 8.99E−11 | 1.29E−10 | 4.58E−10 |
| cyno IL-5 | 2.05E−10 | 2.77E−10 | 3.12E−10 | 4.76E−10 | 9.98E−9 |

This example proves that the antibodies mAb1705, mAb1706, mAb1780, mAb1773 and mAb1779 of the present disclosure have high affinity to IL-5 of different species (human, monkey).

Test Example 2. The Affinity of Humanized IL-5 Antibody to IL-5 of Different Species by Biacore Assay The affinity of the humanzied IL-5 antibody to be tested with human IL-5 was measured by Biacore T200 (GE) instrument.

The protein A biosensor chip was used to affinity capture of the molecules to be tested, and then the antigen (prepared in Example 1) flowed through the surface of the chip, and the reaction signal was detected in real time with the Biacore T200 instrument to obtain the binding and dissociation curves. After the dissociation of each experimental cycle was completed, the biosensor chip was washed and regenerated with glycine-hydrochloric acid regeneration solution (pH 1.5). BIAevaluation version 4.1 GE software was used to fit the data against (1:1) Langmuir model, and the affinity value was obtained and shown in Table 14.

TABLE 14

| Results of affinity of humanized IL-5 antibodes to human IL-5 by BIAcore assay | |
|---|---|
| Antibody | KD (M) |
| h1705-003 | 3.35E−09 |
| h1705-006 | 4.11E−09 |
| h1705-009 | 4.55E−09 |
| h1705-004 | 2.14E−11 |
| h1705-007 | 2.21E−11 |
| h1705-010 | 2.05E−11 |
| h1705-005 | 2.16E−11 |
| h1705-008 | 3.42E−11 |
| h1705-011 | 2.30E−11 |
| h1706-003 | 1.89E−11 |
| h1706-006 | 1.73E−11 |
| h1706-009 | 5.45E−11 |
| h1780-017 | 7.78E−11 |
| h1773-007 | 2.07E−10 |
| h1779-014 | 4.12E−10 |

The results show that all the humanized IL-5 antibodies have high affinity to human IL-5.

Test Example 3. ELISA-Based Assay of Murine IL-5 Antibody to Block the Binding of IL-5 to IL-5α Receptor To identify the ability of IL-5 antibody to block IL-5 from binding to the extracellular region of recombinantly expressed IL-5α receptor protein, IL-5 (5 μg/ml in PBS) was coated on an ELISA plate and incubated at 37° C. for 1 hour; the liquid was removed, 200 μl/well of 5% skimmed milk blocking solution diluted with PBS was added, and incubated for 2.5 hours in a 37° C. incubator for blocking. After blocking, the blocking solution was removed and the plate was washed with PBST buffer (pH 7.4 PBS comprising 0.05% Tween-20) for 5 times; 25 μl of 10 μg/ml IL-5Rα (in 1% BSA) labeled by a biotin labeling kit (Tojin Chemical, LK03) was added, and then 25 μl of gradient-diluted antibody was added (the antibody competed with IL-5Rα for the binding with IL-5) and incubated at 37° C. for 1 hour. After the incubation, the reaction solution in the microtiter plate was removed, the plate was washed for 5 times with PBST, added with 50 μl/well of Streptavidin-Peroxidase Polymer (Sigma, S2438-250UG) diluted with sample dilution solution at 1:600 and incubated for 1 hour at 37° C. The plate was washed for 5 times with PBST, 50 μl/well of TMB chromogenic substrate (KPL, 52-00-03) was added and incubated at room temperature for 3-10 min; 50 μl/well of 1M $H_2SO_4$ was added to stop the reaction; NOVOStar microplate reader was used to read the absorbance value at 450 nm; the IC50 value of IL-5 antibody to block the binding of IL-5 to IL-5Rα was calculated. The results are shown in Table 15. The antibodies of the present disclosure can effectively inhibit the binding of IL-5 to its receptor.

TABLE 15

| ELISA results of murine IL-5 antibody to block the binding of IL-5 to IL-5α receptor | | |
|---|---|---|
| | mAb1705 | mAb1706 |
| IC50 (μg/ml) | 0.42 | 0.40 |

Test Example 4. FACS-Based Asay of IL-5 Antibody to Block the Binding of IL-5 to IL-5 Receptor In order to identify the screened IL-5 antibody which can block the IL-5 receptor on cell surface, CHOS recombinant cell line that highly expresses two receptors of IL-5Rα/β was constructed. This experiment demonstrated that the IL-5 antibodies can block the binding of IL-5 to the recombinant IL-5α/β receptor on the surface of the CHOS cell line, respectively.

Particular method was as follows: CD-CHO comprising 100 ng/ml G418 and 25 ng/ml zeozin was used to culture CHO-S-IL-5Rα and β. During cell culture, the concentration should not exceed $3\times10^6$ cells/ml. IL-5Rα/β-CHOS cells in good condition were centrifuged (at 1000 rpm, 5 min), and washed once with 10% FBS in PBS, and the cells were counted, the cell concentration was adjusted to $4\times10^6$ cells/ml, and 25 μl was taken out and added into a round-bottom 96-well plate. The antibody to be tested was diluted with PBS solution comprising 10% FBS. The initial concentration was 200 μg/ml, and diluted at 1:10 for 8 gradient dilutions. 25 μl of 100 ng/ml IL-5 labeled by a biotin labeling kit (Tojin Chemical, LK03) was added, and fully mixed with 50 μl of diluted antibody at each concentration, and added into 96-well plate that has been added with cells, and incubated at 4° C. for 1 hour. After the incubation, the sample was centrifuged at 4° C. (400 g, 5 min), and the supernatant was removed, the plated was washed with 200 μl of pre-cooled PBS by centrifugation, repeated for twice; PE-Avidin secondary antibody diluted at 1:1333 was added and incubated in the dark at 4° C. for 40 min, centrifuged at 4° C. (400 g, 5 min); the supernatant was removed, 200 μl of pre-cooled PBS was added to pipette the cells; the plate was washed by centrifugation at 4° C. for three times; 100 μl of PBS was added, the plate was read on machine; the IC50 value of IL-5 antibody to block the binding of IL-5 to IL-5Rα/β was calculated according to the fluorescence signal value. The results are shown in Table 16 and FIG. 1.

TABLE 16

| Test results of IL-5 antibody to block the binding of IL-5 to IL-5Rα/β | | | | | | |
|---|---|---|---|---|---|---|
| Antibody | IgG | hu39D10 | h1705-008 | h1706-009 | h1780-017 | h1779-014 |
| IC50 (ng/ml) | 8777 | 25.07 | 14.51 | 24.74 | 16 | 49.64 |

The results show that the antibodies h1705-008, h1706-009, h1780-017, and h1779-014 show a strong ability to block the binding of IL-5 to IL-5 receptor on cell surface.

Test Example 5. IL-5 Antibody Inhibits IL-5 Induced Proliferation of TF1 Cells IL-5 can induce the proliferation of TF-1 cells, and the IL-5 antibody can prevent IL-5 from stimulating the proliferation of TF-1 cells.

In particular: TF-1 cells (ATCC, CRL-2003) were cultured in RPMI1640 comprising 10% FBS and 2 ng/mL rhGM-CSF (LinkBio, Catalog No. 96-AF-300-03-20), placed in 37° C., 5% $CO_2$ incubator, the cell density would not exceed $1\times10^6$ cells/ml. To detect the antibodies, cells at logarithmic growth phase were washed with PBS for three times and centrifuged at 800 rpm for 5 min; the cell density was adjusted to 6000 cells/well/90 μl with RPMI1640 (FBS:

2%, recombinant human IL-5: 10 ng/ml); 10 μl of the gadient-diluted antibody to be tested was added to a 96-well plate for culture, after 3 days of culture, 30 μl of cell titer was added and mixed for detection, IC50 was calculated according to the readings. The test results are shown in Table 17 below.

TABLE 17

| Test results of IL-5 humanized antibody to inhibit the IL-5 induced TF1 cell proliferation | |
|---|---|
| Antibody | IC50 (nM) |
| Hu39D10 | 0.30 |
| h1705-004 | 0.30 |
| h1705-005 | 0.30 |
| h1705-007 | 0.25 |
| h1705-008 | 0.20 |
| h1705-010 | 0.30 |
| h1705-011 | 0.28 |
| h1706-003 | 0.31 |
| h1706-004 | 0.30 |
| h1706-006 | 0.34 |
| h1706-007 | 0.28 |
| h1706-009 | 0.25 |
| h1773-007 | 0.38 |
| h1780-017 | 0.16 |
| h1779-014 | 0.20 |

Test Example 6. Test of IL5 Antibody to Inhibit the IL5-Induced Eosinophil Adhesion IL5 can induce the differentiation, maturation, migration and activation of eosinophils, causing inflammation of the respiratory and leading to asthma. This experiment is based on the principle that IL-5 cytokines can promote the adhesion and activation of eosinophils. The eosinophils were collected and purified from human peripheral blood to test the blocking effect of IL-5 specific antibodies on IL-5 pathway, and to detect the blocking effect of IL-5 antibodies on IL5-mediated eosinophil adhesion in vitro.

In particular: human peripheral blood was 5-fold diluted with PBS comprising 2 mM EDTA, and Percoll™ (density gradient of 1.088) was used to isolate monocytes and granulocytes. The red blood cell layer comprising granulocytes was carefully aspirated, and red blood cell lysis solution was used to remove red blood cells; the remaining cells were counted, the separation magnetic beads (Miltenyi Biotec, Catalog No. 130-045-701) with CD16 antibody were added in proportion, and incubated for 30 min and flowed through the magnetic bead column, the subpopulations (mainly eosinophils) directly flowing through the column were collected by negative selection. The isolated eosinophils were counted and added to a 96-well cell culture plate pre-coated with IgG antibody, with about $1\times10^4$ cells per well; human IL-5 (20 ng/ml) and IL-5 antibody molecules at different concentrations (starting from 10 μg/ml, 3-fold dilution, 10 concentration points) were added; the cell culture plate was placed in 37° C., 5% $CO_2$ incubator and incubated for 1 hour, then the culture plate was taken out and 0.3% CTAB was added to lyse the cells, and finally the peroxidase reaction substrate TMB was added for color development, and the OD450 absorption value was read with a microplate reader. The reading value for the well added with IL-5 alone was the maximum absorption value; the well without IL-5 and antibody agent was served as background control; the inhibition value of antibody agent at each concentration relative to the maximum adsorption value was calculated=(maximum adsorption value−[antibody agent])/(maximum adsorption value−background control value)×100%, and the IC50 was calculated. The results are shown in Table 18:

TABLE 18

| IL-5 antibody blocks IL-5 induced eosinophil adhesion | | | | |
|---|---|---|---|---|
| | Hu39D10 | h1705-008 | h1706-009 | h1780-017 |
| IC50 (ng/ml) | 11.79 | 4.85 | 4.3 | 21.19 |

The results show that the humanized antibodies of the present disclosure show a strong ability to inhibit IL5-mediated eosinophil adhesion.

Test Example 7. Evaluation of Specificity of Humanized IL-5 Antibody with Th2 Cytokine IL-5 was one of Th2 cytokines. In order to verify that IL-5 antibody only specifically targets IL-5 and does not cross-react with other cytokines, Fortebio was used to detect 12 types of Th2 and related cytokines, comprising IL2 (R&D, 202-IL-010/CF), IL4 (R&D, 204-IL-050/CF), IL-5 (R&D, 205-IL-025/CF), IFNgamma, IL6 (R&D, 7270-IL-025/CF), IL9 (R&D, 209-IL-010/CF), IL10 (R&D, 217-IL-025/CF), IL13 (R&D, 213-ILB-025/CF), IL25 (R&D, 8134-IL-025/CF), IL31 (R&D, 2824-IL-010/CF), and IL3 (203-IL-050/CF) and GMCSF (R&D, 215-GM-010/CF) that share a receptors with IL-5.

Figure 2:
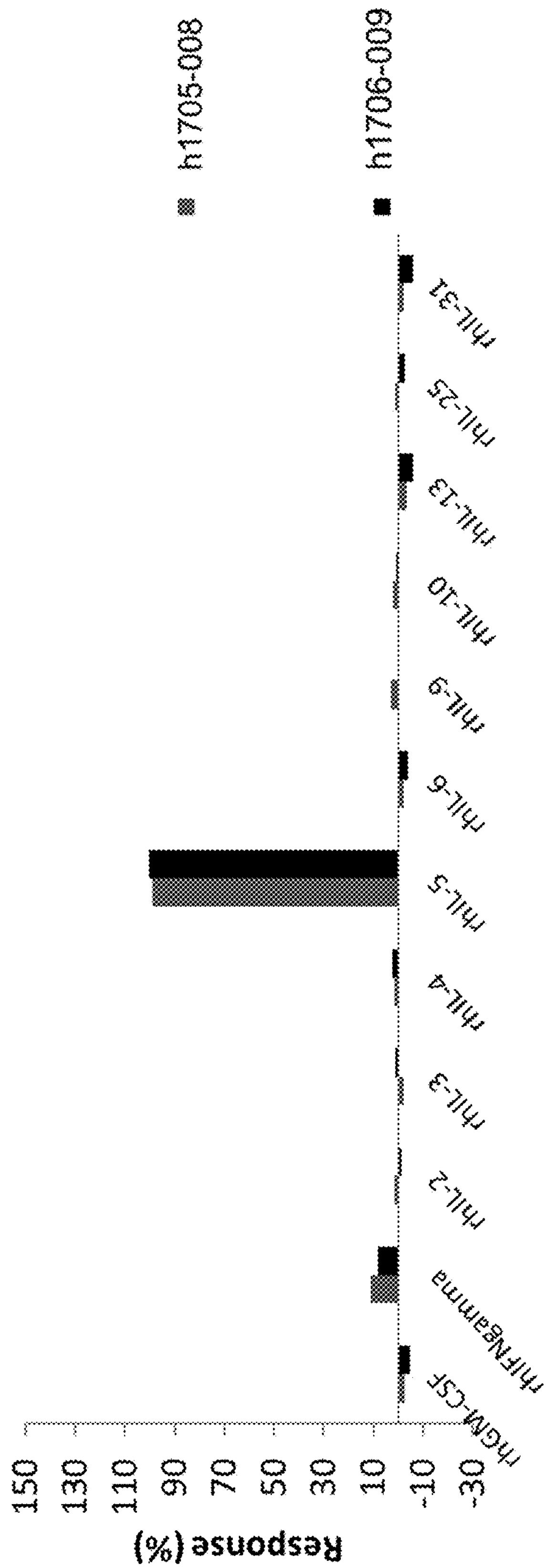
FIG. 2 represents the detection result of binding specificity of the anti-IL-5 antibody for Th2 cytokine.

In particular: Protein A Biosensor (PALL Fortebio, 18-5010) was used to capture the antibody, the capture signal was recorded, and then 40 nM each cytokine was injected, the new binding signal was recorded. Finally, the binding signal with IL-5 was defined as 100%. The binding signals of other cytokines with antibodies were observed, and the results are shown in FIG. 2.

The results show that, among 12 related cytokines, humanized IL-5 antibodies h1705-008 and h1706-009 only specifically bind to IL-5, and have no cross-reactivity with other Th2 cytokines.

Biological Evaluation of In Vivo Activity

Test Example 8. Evaluation of the Efficacy of IL-5 Antibody in OVA-Induced Mouse Asthma Model This test was based on airway inflammatory response and airway remodeling to evaluate the efficacy of IL-5 antibody in BALB/c mouse asthma model induced by ovalbumin (OVA) aerosol.

The mice were randomly divided into 7 groups according to body weight, each group with 10 mice: normal control group (G1); model group (G2); the treatment groups of two antibodies to be tested h1705-008 (G3 and G4) and h1706-009 (G5 and G6) at two doses (10mpk and 2mpk) of each antibody to be tested; and positive antibody Hu39D10 control group (G7, 10mpk). On days 1 and 14, all mice were sensitized by intraperitoneal injection of allergenic solution. On days 28, 29, and 30, the six groups of mice (except the first group) were challenged by aerosol OVA challenge solution for 30 minutes. Two hours before the challenge, the second group (G2) was intraperitoneally injected with phosphate buffer, mice in the third group to the seventh group (G3-G7) were intraperitoneally injected with different doses of different antibodies (once a day, for three consecutive days). The antibodies to be tested were freshly prepared before each injection, and the administration was finished within half an hour since the preparation of antibody. Mice in the first group (as normal control group) were challenged with PBS aerosol for 30 minutes, and 2 hours before the challenge phosphate buffer was injected intraperitoneally once a day for three consecutive days.

On day 31, the WBP system was used to test the airway hyperresponsiveness of the animals. All animals were administered by aerosol to intake methacholine at 2-fold incremental concentrations (1.5625, 3.125, 6.25, 12.5, 25 and 50 mg/mL), the values of respiratory enhanced pause at corresponding concentrations were measured.

On day 31, 1 hour after the detection of airway responsiveness by WBP system, a tracheal tube with a diameter of 1.2 mm was inserted into trachea and fixed, and lung lavage was performed twice, each with 0.8 ml phosphate buffer comprising 1% BSA and 0.6 mM EDTA. The recovery volume of lavage fluid was recorded.

The BALF was centrifuged at 300 g at 4 degrees Celsius for 5 minutes. The supernatant was maintained for cytokine analysis. After centrifugation, the cells were resuspended in 1.5 ml of PBS (comprising 1% BSA and 0.6 mM EDTA) for cell counting. Hemocytometer and trypan blue staining experiment were used to count the total number of cells in BALF. The cells were smeared on silde, and stained with Wright staining solution for one minute, and then stained with Giemsa for 7 minutes to distinguish eosinophils, neutrophils, macrophages and lymphocytes. Counting was performed under a light microscope.

After lavage, the lung tissue was collected and stained with 10% neutral formaldehyde solution, and then fixed in 10% neutral formaldehyde solution. The fixed tissue was embedded in paraffin, trimmed, stained by H&E and scored. The test results are shown in FIG. 3, FIG. 4A and FIG. 4B.

Figure 3:
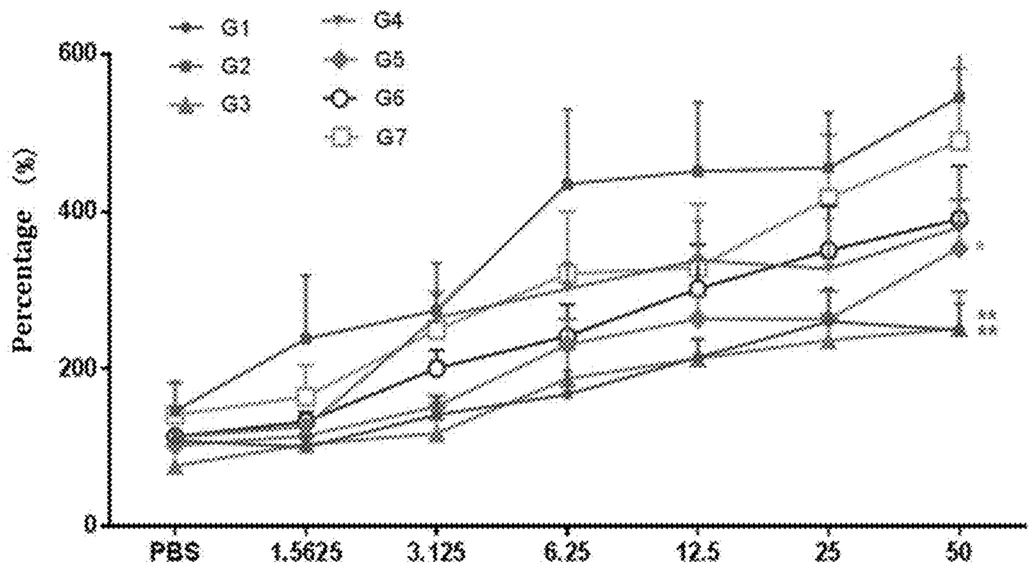
FIG. 3 represents that the anti-IL-5 antibody enhances the leavel of intermittent respiratory (Penh). G1: normal control group (PBS); G2: model group (IgG); G3: h1705-008 antibody 10mpk group; G4: h1705-008 antibody 2mpk group; G5: h1706-009 antibody 10mpk group; G6: h1706-009 antibody 2mpk group; G7: Hu39D10 10mpk group; wherein, *$p<0.05$, **<0.01 (compared with G2 group, by ANOVA/Bonferroni)
Figure 4A:
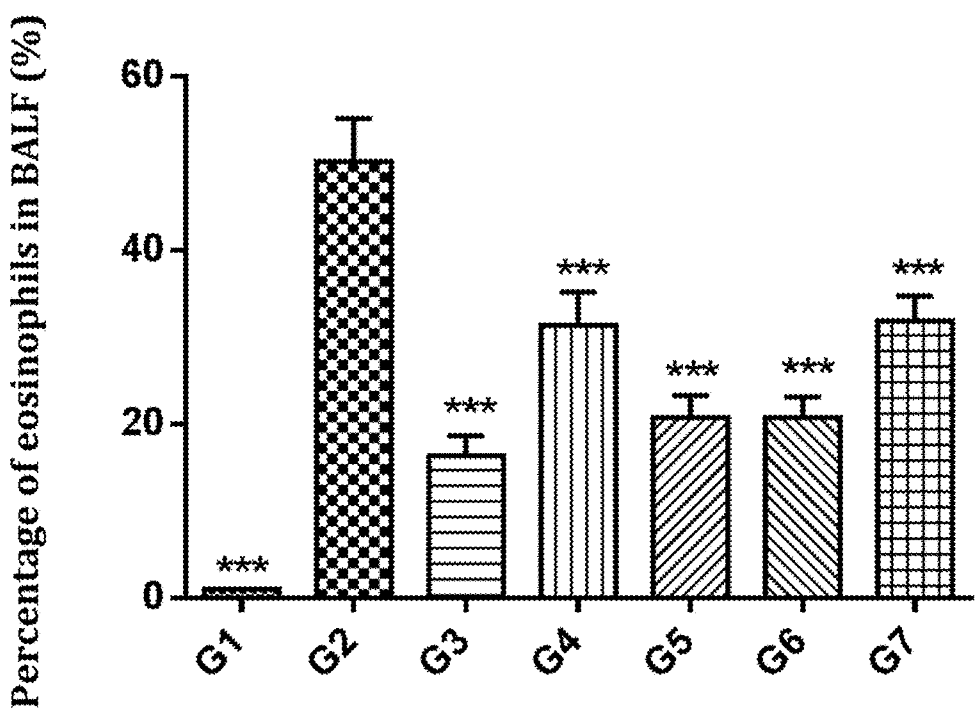
FIG. 4A represents the level of BALF eosinophils in lungs of asthmatic mice.
Figure 4B:
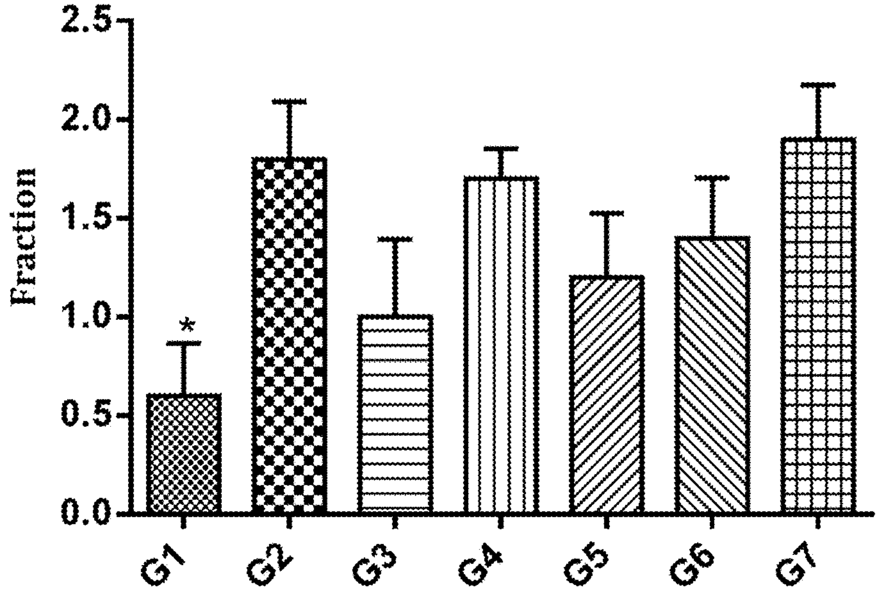
FIG. 4B represents the tracheal mucosal thickness score of asthmatic mice. G1: normal control group; G2: model group; G3: h1705-008 antibody 10mpk group; G4: h1705-008 antibody 2mpk group; G5: h1706-009 antibody 10mpk group; G6: h1706-009 antibody 2mpk group; G7: Hu39D10 10mpk group.
Figure 4C:
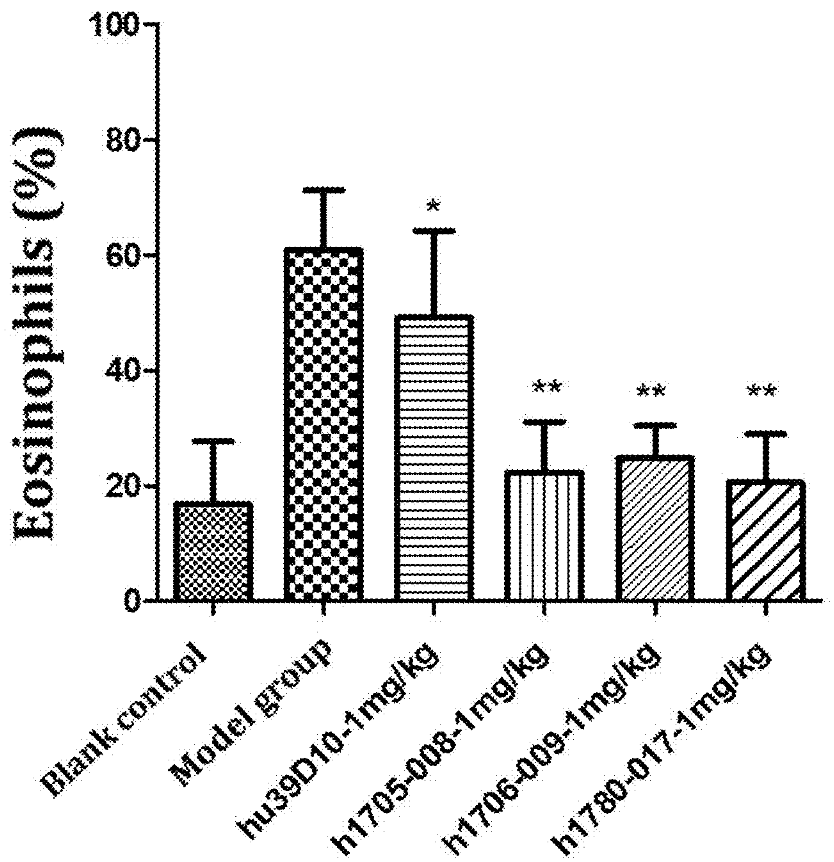
FIG. 4C represents the percentage of BALF eosinophils in lungs of asthmatic mice.

The results show that the antibody molecules h1705-008 and h1706-009 of the present disclosure can significantly improve lung function in a dose-dependent mode, while high dose (10mpk) of the positive compound cannot improve lung function (see FIG. 3). Meanwhile, the two antibodies significantly reduce the level of eosinophils and the thickness of the mucous membrane at the same dose (10mpk), and show a stronger ability to reduce eosinophils than that of the positive antibody (see FIGS. 4A and 4B). In the same type of mouse asthma model, repeatitive experiments also verified that 1 mg/ml h1705-008, h1706-009 and h1780-017 significantly reduce the level of eosinophils in BalF than that of the positive antibody (see FIG. 4C).

Test Example 9. Evaluation of the In Vivo Efficacy of IL-5 Antibody in Guinea Pig Acute Asthma Model Induced by Exogenous Human IL-5

Figure 5A:
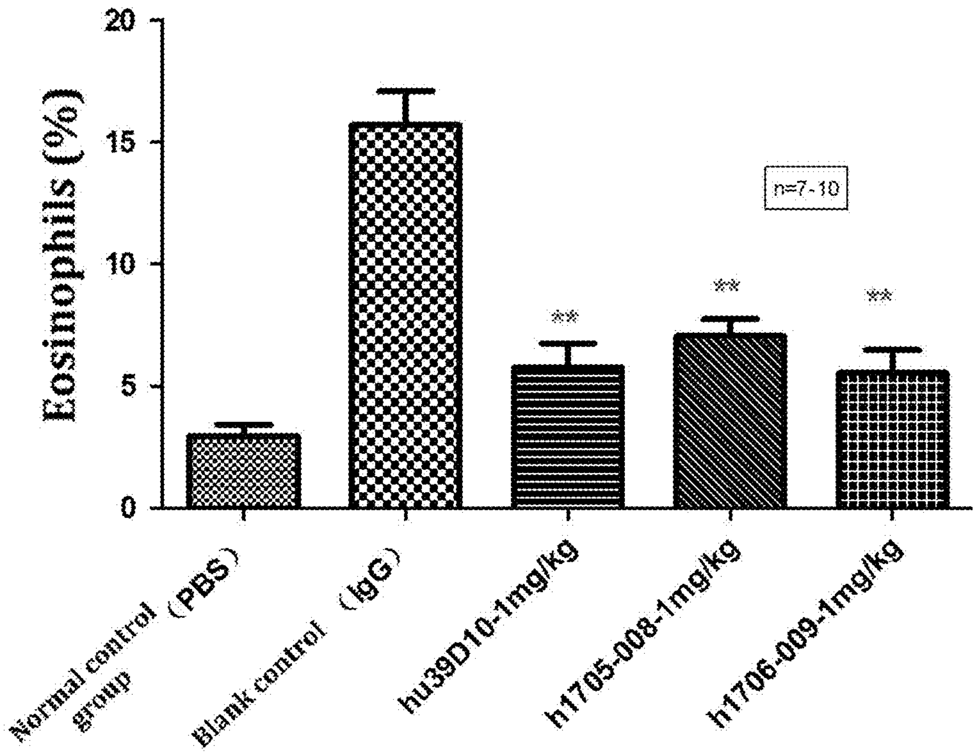
FIG. 5A and FIG. 5B represent the ability of the IL5 monoclonal antibody to reduce the level of eosinophils in BALF.
Figure 5B:
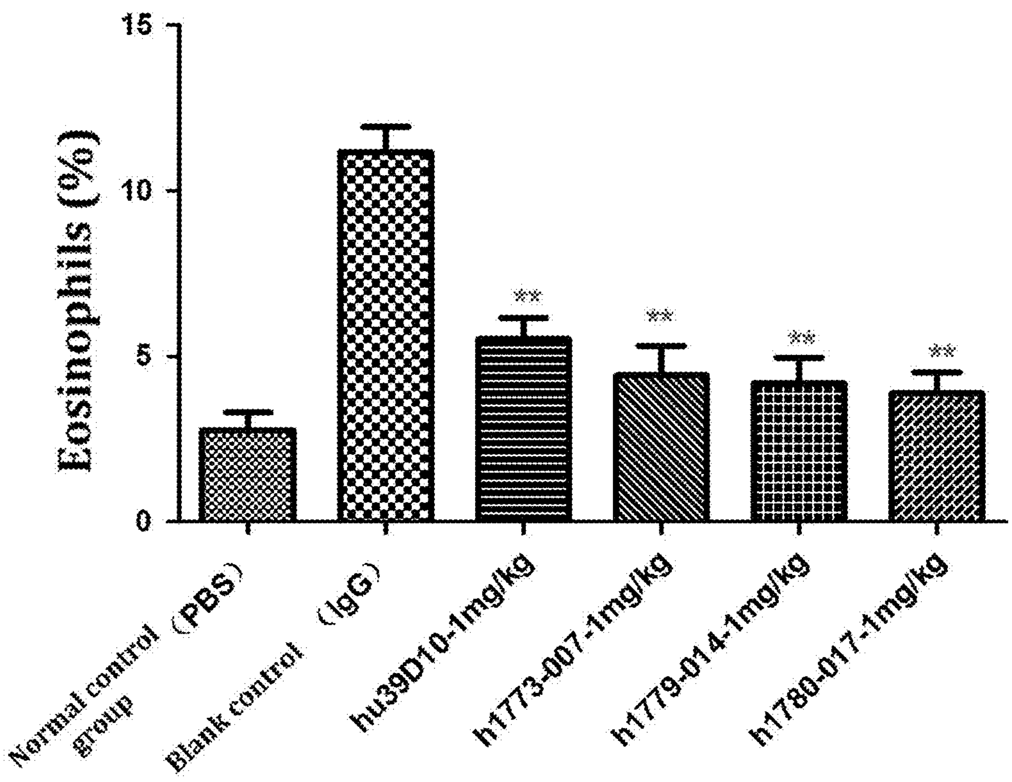

In this experiment, male guinea pigs were selected to establish acute asthma model induced by human IL-5, to evaluate the inhibitory effect of five IL-5 humanized mAbs of the present disclosure on the increase of eosinophils in bronchial lavage fluid (BALF) of guinea pig lung induced by human IL-5; and hu39D10 was used as a positive antibody. The guinea pigs were divided into 9 groups, each with 8-10 animals: normal control group, model group, hu39D10 (1 mg/kg) group, h1705-008 (1 mg/kg) group, h1706-009 (1 mg/kg) group, h1780-017 (1 mg/kg) group, h1773-007 (1 mg/kg) group and h1779-014 (1 mg/kg) group. The guinea pigs in model group and administration groups were tracheally injected with 100 μl of human IL5 (comprising 5 μg of IL5 antigen) on day1 for irritation, respectively; and the normal control group was tracheally injected with PBS. The administration group was intraperitoneally injected with 1 mg/kg IL5 monoclonal antibody as described above, 2 hours before irritation, with the administration volume of 5 ml/kg; the model group was administered with the corresponding IgG antibody; and the normal control group was intraperitoneally administered with PBS solvent. The guinea pigs were anesthetized 24 hours after the tracheal injection, to extract the lung bronchial lavage fluid. The cell concentration was adjusted to $5^\wedge 10^6$/ml, 15 μl was dropped on the slide and dried for fixing; HE staining was performed, and the numbers of total cells and of eosinophils were counted under 400-fold microscope, and the percentage of eosinophils was calculated. The results are shown in FIG. 5A and FIG. 5B, indicating that 5 humanized antibodies of the present disclosure significantly reduce the level of eosinophils in BALF.

Selection and Stability Evaluation of the Ingredients in the Formulation

Exemplary preparation process for the pharmaceutical composition (formulation) of antibody:

- Step 1: a certain amount of purified anti-IL-5 antibody solution was taken, and an antibody-free buffer (such as 30 mM, pH5.5 acetic acid-sodium acetate buffer) was used to replace solvent-exchange (preferably by ultrafiltration); at least 6-fold of volume was exchanged by ultrafiltration membrane, and the protein was concentrated to about 120 mg/mL. A certain volume of sucrose stock solution was added and mixed to get a final concentration of 72 mg/mL of sucrose. A certain volume of polysorbate 80 stock solution was added and mixed to get a final concentration of 0.4 mg/mL of polysorbate 80. 10 mM pH 5.5 acetic acid-sodium acetate buffer was added to reach a certain volume, resuting in the protein concentration of 100 mg/mL (other formulations to be tested or stable formulations were prepared according to similar steps).

The product was filtered, and then was tested by central-control sampling for pathogenic agents-free. The stock solution was passed through a 0.22 μm PVDF filter, and the filtrate was collected.

- Step 2: the volume was adjusted to 1.2 ml, the filtrate was loaded in 2 ml vial applied with stopper, and central-control samplings were taken at the beginning, in the middle, and at the end of loading to detect the difference of loading volume.
- Step 3: the capping machine was started to apply aluminum caps, and to perform capping.
- Step 4: visual inspection was performed to confirm that products have no defects, such as inaccurate loading. The vial labels were printed and attached; the carton labels were printed; the cartons were folded; packing; and box labels were attached.

Test Example 10. Screening of Buffer System

The h1705-008 formulations with a protein concentration of 100 mg/mL were prepared in a series of buffers at pH of 5.0 to 6.5, wherein the shaking sample comprised 0.2 mg/ml polysorbate 80 (PS80), and other samples comprised 0.05 mg/mL PS80. The buffer systems were as follows: 10 mM acetic acid-sodium acetate (AA) pH5.0, 5.5; 10 mM succinic acid-sodium succinate (SA) pH5.0, 5.5, 6.0; 10 mM citric acid-sodium citrate (CA) pH5.5, 6.0, 6.5; 10 mM histidine-hydrochloride (His) pH5.5, 6.0, 6.5; 10 mM phosphate (PB) pH6.0, 6.5. Each formulation was filtrated, loaded, applied with stopper and capped. The samples were subjected to a forced degradation experiment; and appearance, SEC, iCIEF were served as evaluation indicators.

The results are shown in Table 19. Appearance data indicates that the samples experienced shaking (300 rpm, 25° C.) and samples at 40° C. show different degrees of particle formation. Overall, the appearance is better when the pH is lower, and the buffer systems acetic acid-sodium acetate and succinic acid-sodium succinate are better; SEC data shows that AA pH 5.5 group is slightly better at 40° C.; iCIEF data shows that AA pH 5.5, His pH 5.5, CA pH 6.5 groups are slightly better at 40° C.; under comprehensive consideration of physical and chemistry stability, AA pH 5.5 is preferable.

TABLE 19

Screening results for pH and buffer system

| Batch No. | Condition | Appearance | SEC (%) | iCIEF neutral peak (%) |
|---|---|---|---|---|
| 01 | T0 | clear | 98.3 | 75.3 |
| AA5.0 | Shaking D4 | clear | 96.2 | N/A |
| | 40° C.-D13 | fine particles | 94.8 | 62.3 |
| 02 | T0 | clear | 98.0 | 75.4 |
| AA5.5 | Shaking D4 | clear | 96.0 | N/A |
| | 40° C.-D13 | flocculent small particles | 95.4 | 64.2 |
| 03 | T0 | clear | 98.2 | 74.9 |
| SA5.0 | Shaking D4 | clear | 96.5 | N/A |
| | 40° C.-D13 | fine particles+ | 94.8 | 59.3 |
| 04 | T0 | clear | 98.2 | 74.7 |
| SA5.5 | Shaking D4 | large amount of small particles | 96.2 | N/A |
| | 40° C.-D13 | small particles | 94.8 | 62.1 |
| 05 | T0 | clear | 97.9 | 75.8 |
| SA6.0 | Shaking D4 | clear, slightly opalescence | 95.7 | N/A |
| | 40° C.-D13 | small particles | 95.0 | 63.7 |
| 06 | T0 | clear | 98.2 | 75.7 |
| His5.5 | Shaking D4 | clear, few particles | 96.2 | N/A |
| | 40° C.-D13 | small particles | 94.9 | 64.8 |
| 07 | T0 | clear | 98.3 | 74.6 |
| His6.0 | Shaking D4 | large amount of particles | 96.2 | N/A |
| | 40° C.-D13 | medium particles | 94.6 | 65.8 |
| 08 | T0 | clear | 98.1 | 74.6 |
| His6.5 | Shaking D4 | severe opalescence | 95.8 | N/A |
| | 40° C.-D13 | medium particles | 94.3 | 62.3 |
| 09 | T0 | clear | 98.2 | 74.8 |
| CA5.5 | Shaking D4 | clear, slightly opalescence | N/A | N/A |
| | 40° C.-D13 | fine particles | 94.7 | 60.9 |
| 10 | T0 | clear | 98.0 | 75.3 |
| CA6.0 | Shaking D4 | obvious opalescence, large amount of particles | N/A | N/A |
| | 40° C.-D13 | medium particles | 94.6 | 61.5 |
| 11 | T0 | clear | 97.9 | 74.6 |
| CA6.5 | Shaking D4 | severe opalescence, large amount of particles | N/A | N/A |
| | 40° C.-D13 | small particles | 95.0 | 64.4 |
| 12 | T0 | clear | 98.0 | 74.4 |
| PB 6.0 | Shaking D4 | with particles | N/A | N/A |
| | 40° C.-D13 | fine particles | 94.3 | 63.0 |
| 13 | T0 | clear | 97.9 | 74.7 |
| PB 6.5 | Shaking D4 | severe opalescence, large amount of particles | N/A | N/A |
| | 40° C.-D13 | large particles | 93.9 | 61.9 |

Note:
N/A represents not detected, D represents the day, and T0 represents day 0.

Test Example 11. Screening of Excipients in Formulations

The h1705-008 formulations with a protein concentration of 100 mg/mL were prepared in 10 mM SA (pH 5.0) buffer comprising different types of excipients below. In particular, the excipients were as follows:

1) 0.1 mg/mL polysorbate 20 (PS20)
2) 0.1 mg/mL polysorbate 80 (PS80)
3) 50 mg/mL sucrose+0.1 mg/mL PS80
4) 50 mg/mL trehalose+0.1 mg/mL PS80
5) 50 mg/mL mannitol+0.1 mg/mL PS80
6) 50 mg/mL sorbitol+0.1 mg/mL PS80
7) 8 mg/ml arginine (Arg)+0.1 mg/mL PS80
8) 8 mg/ml lysine (Lys)+0.1 mg/mL PS80
9) 8 mg/ml glycine (Gly)+0.1 mg/mL PS80
10) 8 mg/ml methionine (Met)+0.1 mg/mL PS80
11) 8 mg/ml proline (Pro)+0.1 mg/mL PS80
12) 8 mg/ml sodium chloride (NaCl)+0.1 mg/mL PS80.

Each formulation was filtrated, loaded, applied with stopper and capped, for use. The samples were subjected to a forced degradation experiment at 40° C., the results show that (Table 20): there is no significant difference in the test results of SEC, CE, and iCIEF among each group of samples, Arg/Lys/NaCl groups have poorer appearance, and there is no significant difference among other groups. Sucrose, trehalose, mannitol, sorbitol, glycine, proline, and methionine have favorable effect on protein stability.

TABLE 20

The screening results of excipients

| Batch No. | Condition | Appearance | SEC (%) | iCIEF neutral peak (%) | CE-SDS (%) |
|---|---|---|---|---|---|
| 1 | D0 | clear | 96.6 | 75.16 | 95.05 |
| | 40° C. D12 | clear | 94.29 | 59.24 | 93.53 |
| 2 | D0 | clear | 96.64 | 74.39 | 94.96 |
| | 40° C. D12 | clear | 94.33 | 58.99 | 93.31 |
| 3 | D0 | clear | 96.59 | 74.51 | 95.44 |
| | 40° C. D12 | clear | 94.33 | 58.33 | 93.3 |
| 4 | D0 | clear | 96.63 | 74.87 | 95.26 |
| | 40° C. D12 | clear | 94.43 | 58.14 | 93.68 |
| 5 | D0 | clear | 96.63 | 74.8 | 95.33 |
| | 40° C. D12 | clear | 94.47 | 59.79 | 93.43 |
| 6 | D0 | clear | 96.63 | 74.25 | 95.29 |
| | 40° C. D12 | clear | 94.39 | 58.04 | 93.41 |
| 7 | D0 | clear, light opalescence | 96.6 | 74.31 | 95.19 |
| | 40° C. D12 | opalescence, large amount of particles | 94.27 | 59.18 | 93.45 |
| 8 | D0 | clear, light opalescence | 96.56 | 74.7 | 95.2 |
| | 40° C. D12 | opalescence | 94.26 | 59.62 | 93.56 |
| 9 | D0 | clear | 96.54 | 73.77 | 95.47 |
| | 40° C. D12 | clear | 94.38 | 58.82 | 93.56 |
| 10 | D0 | clear | 96.56 | 75.68 | 95.5 |
| | 40° C. D12 | clear | 94.45 | 59.57 | 93.71 |
| 11 | D0 | clear | 96.43 | 75.22 | 95.02 |
| | 40° C. D12 | clear | 94.47 | 61.1 | 95.32 |
| 12 | D0 | clear, opalescence | 96.51 | 73.63 | 95.02 |
| | 40° C. D12 | opalescence, large amount of particles | 93.99 | 60.51 | 93.21 |

Note:
D represents day.

Test Example 12. Screening of Surfactants

The h1705-008 formulations comprising 10 mM SA pH5.5, 70 mg/ml sucrose, 0.4 mg/ml PS20 or PS80 were prepared, with a protein concentration of 100 mg/ml.

The samples were placed at 4° C. to investigate the stability. The results are shown in Table 21. The results show that PS80 group exhibits a clear appearance and no significant changes in SEC, CE, and iCIEF at 4° C. for 4 months, indicating a favorable stability; whereas a large amount of particles are observed in PS20 group. Therefore, PS80 is better than PS20. In addition, it can be seen that the addition of PS80 into the formulation has a better stabilizing effect on h1705-008, and the stability of the formulation is better.

TABLE 21

| stability results of h1705-008 at 4 °C | | | | | |
|---|---|---|---|---|---|
| Group | Time (M) | Appearance | SEC (%) | Non-reducing CE-SDS (%) | iCIEF neutral peak (%) |
| PS80 | 0 | clear | 97.2 | 94.4 | 71.2 |
| | 4 | clear | 97.6 | 95.0 | 71.6 |
| PS20 | 0 | clear | 97.1 | 94.3 | 72.7 |
| | 4 | large amount of particles | N/A | N/A | N/A |

Note:
M represents month;
N/A represents not detected.

Test Example 13. The Design and Screening of DOE Formulation

DOE (Design of expriment) was performed with pH of 10 mM acetate buffer (AA), protein concentration and Tween concentration as variables; a series of formulations were designed based on the following factors and levels: pH is 5.0 to 5.8, the concentration of PS80 is 0.2 to 0.6 mg/mL, concentration of the antibody h1705-008 is 80 to 120 mg/mL; The formulations are shown in Table 22. The samples were subjected to forced degradation at high temperature of 40° C. Appearance, SEC, non-reducing CE, and iCIEF were used as evaluation indicators. The results are shown in Table 23.

TABLE 22

| Screening experiment and design for DOE formulations | | | |
|---|---|---|---|
| Batch No. | pH | PS80 (mg/mL) | The amount of protein (mg/mL) |
| 1 | 5.8 | 0.2 | 80 |
| 2 | 5.4 | 0.6 | 100 |
| 3 | 5.4 | 0.4 | 80 |
| 4 | 5.0 | 0.2 | 80 |
| 5 | 5.4 | 0.2 | 100 |
| 6 | 5.8 | 0.6 | 80 |
| 7 | 5.0 | 0.2 | 120 |
| 8 | 5.0 | 0.6 | 80 |
| 9 | 5.8 | 0.6 | 120 |
| 10 | 5.4 | 0.4 | 120 |
| 11 | 5.4 | 0.4 | 100 |
| 12 | 5.0 | 0.6 | 120 |
| 13 | 5.8 | 0.2 | 120 |
| 14 | 5.0 | 0.4 | 100 |
| 15 | 5.8 | 0.4 | 100 |
| 16 | 5.4 | 0.4 | 100 |

TABLE 23

| Screening experiment results of DOE formulations | | | | | |
|---|---|---|---|---|---|
| Batch No. | Condition | Appearance | SEC (%) | iCIEF neutral peak (%) | Non-reducing CE-SDS (%) |
| 1 | D0 | clear | 98.9 | 63.9 | 93.8 |
| | 40° C. D15 | clear | 97.8 | 49.9 | 92.5 |
| 2 | D0 | clear | 98.9 | 64.5 | 93.8 |
| | 40° C. D15 | clear | 97.5 | 49.8 | 92.9 |
| 3 | D0 | clear | 98.9 | 64.3 | 94.0 |
| | 40° C. D15 | clear | 97.6 | 49.6 | 92.2 |
| 4 | D0 | clear | 99.0 | 63.6 | 93.9 |
| | 40° C. D15 | clear | 97.7 | 50.3 | 92.4 |

TABLE 23-continued

| Screening experiment results of DOE formulations | | | | | |
|---|---|---|---|---|---|
| Batch No. | Condition | Appearance | SEC (%) | iCIEF neutral peak (%) | Non-reducing CE-SDS (%) |
| 5 | D0 | clear | 98.9 | 63.4 | 93.8 |
| | 40° C. D15 | clear | 97.6 | 49.7 | 92.2 |
| 6 | D0 | clear | 98.9 | 63.5 | 93.9 |
| | 40° C. D15 | clear | 97.7 | 51.5 | 92.4 |
| 7 | D0 | clear | 98.9 | 64.3 | 93.7 |
| | 40° C. D15 | clear | 97.6 | 49.2 | 92.4 |
| 8 | D0 | clear | 99.0 | 64.4 | 93.9 |
| | 40° C. D15 | clear | 97.7 | 49.6 | 92.3 |
| 9 | D0 | clear | 98.7 | 66.2 | 93.8 |
| | 40° C. D15 | clear | 97.3 | 50.6 | 92.4 |
| 10 | D0 | clear | 98.8 | 64.1 | 93.9 |
| | 40° C. D15 | clear | 97.4 | 50.9 | 92.3 |
| 11 | D0 | clear | 98.8 | 64.5 | 94.0 |
| | 40° C. D15 | clear | 97.5 | 50.6 | 92.4 |
| 12 | D0 | clear | 99.0 | 64.4 | 93.7 |
| | 40° C. D15 | clear | 97.6 | 49.9 | 92.3 |
| 13 | D0 | clear | 98.8 | 63.7 | 93.8 |
| | 40° C. D15 | clear | 97.4 | 50.8 | 92.6 |
| 14 | D0 | clear | 99.0 | 63.6 | 93.9 |
| | 40° C. D15 | clear | 97.7 | 50.9 | 92.1 |
| 15 | D0 | clear | 98.8 | 63.0 | 93.6 |
| | 40° C. D15 | clear | 97.6 | 51.1 | 92.4 |
| 16 | D0 | clear | 98.8 | 64.9 | 93.8 |
| | 40° C. D15 | clear | 97.5 | 50.0 | 92.3 |

Note:
D represents day.

The results show that the appearance of each formulation is clear; SEC, CE and iCIEF are decreased within an acceptable range, by <2%, <2% and about 14%, respectively; and the stability of formulation is favorable; therefore the formulation comprises a protein concentration of 80-120 mg/ml, 0.2-0.6 mg/ml PS80, pH 5.0-5.8. The optimal formulation is: 100 mg/ml protein, 0.4 mg/ml PS80, pH 5.5.

Test Example 14. Stability test

The h1705-008 formulations comprising 10 mM AA pH 5.5, 70 mg/ml sucrose, and 0.4 mg/ml PS80 were prepared, with a protein concentration of 100 mg/ml; and the samples were subjected to stability investigation at 4° C. and 25° C. The results are shown in Table 24.

The results show that under high temperature conditions, SEC, CE, and iCIEF are slightly decreased in h1705-008 formulation, but the decrease is within an acceptable range; there is no significant change in all indicators under other conditions. The formulation has favorable stability, and can ensure the stability of h1705-008 at 4° C. within 6 months.

TABLE 24

| Stability results of h1705-008 at 25° C. and 4° C. | | | | |
|---|---|---|---|---|
| Condition | Appearance | SEC (%) | iCIEF neutral peak (%) | Non-reducing CE-SDS (%) |
| T0 | clear | 98.0 | 59.8 | 94.5 |
| 25° C.-M3 | clear | 97.6 | 55.2 | 93.4 |
| 25° C.-M6 | clear | 96.7 | 51.7 | 91.7 |
| 4° C.-M3 | clear | 98.5 | 59.7 | 94.6 |
| 4° C.-M6 | clear | 98.7 | 60.0 | 94.0 |

Note:
M represents month.

Test Example 15. Screening of Ionic Strength

The h1705-008 formulations comprising protein concentration of 100 mg/mL, 70 mg/mL sucrose and 0.4 mg/mL PS80 were prepared in (sodium) acetate buffer with different ionic strengths; the pH of buffers used for exchange and the pH of the final formulations were measured. The results are shown in Table 25. The results show that the higher the ionic strength, the lower the pH drift. When the ionic strength is 30 mM, the pH drift is less than 0.1.

TABLE 25 pH results of formulations with different ionic strengths

| Ionic strength | Buffer-pH | Stock solution of the formation-pH | ΔpH |
|---|---|---|---|
| 10 mM | 5.50 | 5.71 | 0.21 |
| 20 mM | 5.50 | 5.66 | 0.16 |
| 30 mM | 5.50 | 5.59 | 0.09 |

Test Example 16. Screening of Concentration of Saccharide

The h1705-008 formulations comprising a protein concentration of 100 mg/mL, 30 mM AA pH 5.5, 0.4 mg/ml PS80 were prepared in the following buffers comprising sucrose with different concentrations. The osmotic pressure was determined. The results are shown in Table 26.

The results show that the osmotic pressure is in an optimal isotonic range of 290 to 310 mosm, when the saccharide concentration is 70-75 mg/ml; according to the osmotic pressure data of 70 mg/ml and 73 mg/ml groups, the osmotic pressure reaches the best value of about 300 mosm, when the saccharide concentration is 72 mg/ml.

TABLE 26

Comparison of osmotic pressure in h1705-008 formulations with different saccharide concentrations

| | Concentration of saccharide (mg/ml) | | |
|---|---|---|---|
| | 70 | 73 | 75 |
| Osmotic pressure (mosm) | 290 | 306 | 310 |

Test Example 17. Stability Test of the Formulations

The h1705-008 formulations comprising a protein concentration of 100 mg/mL, 30 mM AA pH 5.5, 72 mg/ml sucrose, 0.4 mg/ml PS80 were prepared to investigate the stability at 4° C. and 25° C. The results are shown in Table 27. The results show that, SEC, CE and IEC are slightly decreased in the h1705-008 formulation under high temperature conditions, but the decrease is within an acceptable range; there is no significant change in all indicators at 4° C. condition, indicating that the formulations have favorable stability.

TABLE 27

Stability of h1705-008 formulations

| Condition | Appearance | SEC (%) | IEC neutral peak (%) | Non-reducing CE-SDS (%) |
|---|---|---|---|---|
| T0 | clear | 98.4 | 63.5 | 97.6 |
| 25° C.-M3 | N/A | 96.8 | 55.0 | 96.5 |
| 4° C.-M3 | clear | 98.4 | 61.9 | 97.3 |

Note:
M represents month, T represents time, N/A represents not determined.

Test Example 18. Additional Optional Formulations

In addition, the present disclosure also provides additional formulations for the anti-IL-5 antibody pharmaceutical formulations, comprising but not limited to:

(1) 1 mg/ml anti-IL-5 antibody (h1705-008), 72 mg/ml sucrose, 0.4 mg/ml polysorbate 80, and 10 mM acetic acid-sodium acetate buffer at pH 5.5;
(2) 100 mg/ml anti-IL-5 antibody (h1705-008), 72 mg/ml sucrose, 0.4 mg/ml polysorbate 80, and 20 mM acetic acid-sodium acetate buffer at pH 5.5;
(3) 120 mg/ml anti-IL-5 antibody (h1705-008), 72 mg/ml sucrose, 0.4 mg/ml polysorbate 80, and 40 mM acetic acid-sodium acetate buffer at pH 5.5;
(4) 100 mg/ml anti-IL-5 antibody (h1705-008), 80 mg/ml sucrose, 0.6 mg/ml polysorbate 80, and 30 mM acetic acid-sodium acetate buffer at pH 5.0;
(5) 80 mg/ml anti-IL-5 antibody (h1705-008), 75 mg/ml sucrose, 0.6 mg/ml polysorbate 80, and 20 mM acetic acid-sodium acetate buffer at pH 5.4;
(6) 100 mg/ml anti-IL-5 antibody (h1705-008), 80 mg/ml sucrose, 0.4 mg/ml polysorbate 80, and 30 mM acetic acid-sodium acetate buffer at pH 5.5;
(7) 90 mg/ml anti-IL-5 antibody (h1705-008), 74 mg/ml sucrose, 0.5 mg/ml polysorbate 80, and 25 mM acetic acid-sodium acetate buffer at pH 5.6;
(8) 90 mg/ml anti-IL-5 antibody (h1705-008), 76 mg/ml sucrose, 0.3 mg/ml polysorbate 80, and 35 mM acetic acid-sodium acetate buffer at pH 5.4;
(9) 80 mg/ml anti-IL-5 antibody (h1705-008), 72 mg/ml sucrose, 0.4 mg/ml polysorbate 80, and 30 mM acetic acid-sodium acetate buffer at pH 5.6;
(10) 100 mg/ml anti-IL-5 antibody (h1705-008), 72 mg/ml sucrose, 0.4 mg/ml polysorbate 80, and 40 mM acetic acid-sodium acetate buffer at pH 5.5;
(11) 100 mg/ml anti-IL-5 antibody (h1705-008), 80 mg/ml sucrose, 0.4 mg/ml polysorbate 80, and 40 mM acetic acid-sodium acetate buffer at pH 5.5.

The experimental results show that the IL-5 antibody formulations as described above have favorable stability and can be applied to the preparation of IL-5 antibody agents.

Test Example 19. Lyophilization of Anti-IL-5 Antibody Formulations

The h1705-008 antibody formulations comprising 72 mg/ml sucrose, 0.4 mg/ml polysorbate 80 and a concentration of 100 mg/ml anti-IL-5 antibody were prepared in 30 mM acetic acid-sodium acetate buffer at pH 5.5. The antibody was loaded into 6 mL vial at 2.15 mL/vial, and was placed in a lyophilization chamber for lyophilization. The lyophilization process comprises pre-freezing, primary drying and secondary drying. When the lyophilization process was over, the vials were subjected to vacuum and applied with stoppers. The reconstituted samples were compared to the counterpart before the lyophilization. The results show that the reconstituted solutions can maintain favorable performance as that of the liquid formulations.

TABLE 28

Lyophilization steps of the formulations

| Process parameters for lyophilization | The set of temperature (° C.) | The degree of vacuum (mBar) |
|---|---|---|
| pre-freezing | 5 | N/A |
| | −45 | N/A |
| primary drying | −27 | 0.1 |
| | 25 | 0.1 |
| secondary drying | 25 | 0.01 |

Note:
N/A represents that the table was not applicable.

What is claimed:

1. A pharmaceutical composition, comprising:

(a) an anti-IL-5 antibody or an antigen-binding fragment thereof wherein, the anti-IL-5 antibody or the antigen-binding fragment thereof comprises a heavy chain variable region comprising HCDR1, HCDR2 and HCDR3 as shown in amino acid sequence SEQ ID NOs: 16, 17 and 18, respectively, and a light chain variable region comprising LCDR1, LCDR2 and LCDR3 as shown in amino acid sequence SEQ ID NOs: 19, 20 and 21, respectively;

(b) a buffer, wherein the buffer is acetic acid-sodium acetate or succinic acid-sodium succinate buffer, the pH of the buffer is 5.0 to 6.5, the concentration of the buffer is 10 mM to 40 mM;

(c) a surfactant, wherein the surfactant is polysorbate 80, the concentration of the polysorbate 80 is 0.1 mg/ml to 0.6 mg/ml;

(d) a stabilizer, wherein the stabilizer is sucrose, the concentration of the sucrose is 50 mg/ml to 80 mg/ml.

2. The pharmaceutical composition according to claim 1, wherein the pH of the buffer is 5.0 to 5.8.

3. The pharmaceutical composition according to claim 1, wherein the concentration of the buffer is 20 mM to 30 mM.

4. The pharmaceutical composition according to claim 1, wherein the concentration of the anti-IL-5 antibody or the antigen-binding fragment thereof is 1 mg/ml to 120 mg/ml.

5. The pharmaceutical composition according to claim 1, wherein the concentration of the polysorbate 80 is 0.2 mg/ml to 0.6 mg/ml.

6. The pharmaceutical composition according to claim 1, wherein the concentration of the sucrose is 70 mg/ml to 75 mg/ml.

7. The pharmaceutical composition according to claim 1, wherein the anti-IL-5 antibody comprises:

a heavy chain variable region as shown in any one of SEQ ID NOs: 49, 50 and 51 or having 95% sequence identity with any one of SEQ ID NOs: 49, 50 and 51; and a light chain variable region as shown in any one of SEQ ID NOs: 46, 47 and 48 or having 95% sequence identity with any one of SEQ ID NOs: 46, 47 and 48.

8. The pharmaceutical composition according to claim 1, wherein the anti-IL-5 antibody comprises human antibody constant region(s).

9. The pharmaceutical composition according to claim 8, wherein the anti-IL-5 antibody comprises:

a heavy chain as shown in SEQ ID NO: 83 and a light chain as shown in SEQ ID NO: 84.

10. A lyophilized formulation comprising the anti-IL-5 antibody or the antigen-binding fragment thereof, which is obtained by lyophilization of the pharmaceutical composition according to claim 1; the lyophilization comprises the steps of pre-freezing, primary drying and secondary drying, successively.

11. A reconstituted solution comprising the anti-IL-5 antibody or the antigen-binding fragment thereof, wherein the reconstituted solution is obtained by reconstitution of the lyophilized formulation according to claim 10.

12. An article comprising a container, wherein the container comprises the pharmaceutical composition according to claim 1.

13. A method for treating IL-5 mediated disease, comprising administering a therapeutically effective amount of the pharmaceutical composition according to claim 1 to a subject in need thereof; wherein the IL-5 mediated disease is selected from the group consisting of asthma, chronic pneumonia, allergic rhinitis, allergic bronchopulmonary aspergillosis disease, eosinophilia, Churg-Strauss syndrome, atopic dermatitis, onchocerciasis dermatitis, intermittent angioedema, eosinophilic myalgia syndrome, eosinophilic gastroenteritis, worm infection, Hodgkin's disease, nasal polyps, Loeffler's syndrome, urticaria, hypereosinophilic bronchitis, nodular arteritis, sinusitis, eosinophilic esophagitis, allergic eosinophilic esophagitis, allergic conjunctivitis, onchocerciasis dermatitis, endometriosis and steroid-dependent eosinophilic bronchitis.

14. The pharmaceutical composition according to claim 1, wherein the pH of the buffer is about 5.5.

15. The pharmaceutical composition according to claim 1, wherein the concentration of the buffer is about 30 mM or about 32 mM.

16. The pharmaceutical composition according to claim 1, wherein the concentration of the anti-IL-5 antibody or the antigen-binding fragment thereof is 80 mg/ml to 120 mg/ml.

17. The pharmaceutical composition according to claim 1, wherein the concentration of the anti-IL-5 antibody or the antigen-binding fragment thereof is about 100 mg/ml.

18. The pharmaceutical composition according to claim 1, wherein the concentration of the polysorbate 80 is about 0.4 mg/ml or about 0.6 mg/ml.

19. The pharmaceutical composition according to claim 1, wherein the concentration of the sucrose is about 72 mg/ml.

20. The pharmaceutical composition according to claim 8, wherein the anti-IL-5 antibody comprises: a human antibody heavy chain constant region as shown in SEQ ID NO: 52 and a human antibody light chain constant region as shown in SEQ ID NO: 53.

* * * * *

SEQUENCE LISTING

```
<160> NUMBER OF SEQ ID NOS: 92

<210> SEQ ID NO 1
<211> LENGTH: 140
<212> TYPE: PRT
<213> ORGANISM: Artificial Sequence
<220> FEATURE:
<223> OTHER INFORMATION: Synthetic Sequence_The amino acid sequence for
      human IL-5 with His-tag (rhIL-5-his)

<400> SEQUENCE: 1

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser His His His His His His
    130                 135                 140


<210> SEQ ID NO 2
<211> LENGTH: 140
<212> TYPE: PRT
<213> ORGANISM: Artificial Sequence
<220> FEATURE:
<223> OTHER INFORMATION: Synthetic Sequence_The amino acid sequence for
      cyno IL-5 with His-tag

<400> SEQUENCE: 2

Met Arg Met Leu Leu His Leu Ser Leu Leu Ala Leu Gly Ala Ala Tyr
1               5                   10                  15

Val Tyr Ala Ile Pro Thr Glu Ile Pro Ala Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
```

-continued

```
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Gly Gly Gln Lys Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser His His His His His His
    130                 135                 140


<210> SEQ ID NO 3
<211> LENGTH: 119
<212> TYPE: PRT
<213> ORGANISM: Artificial Sequence
<220> FEATURE:
<223> OTHER INFORMATION: Synthetic Sequence_The amino acid sequence for
      mouse IL-5 with His-tag

<400> SEQUENCE: 3

Met Glu Ile Pro Met Ser Thr Val Val Lys Glu Thr Leu Thr Gln Leu
1               5                   10                  15

Ser Ala His Arg Ala Leu Leu Thr Ser Asn Glu Thr Met Arg Leu Pro
            20                  25                  30

Val Pro Thr His Lys Asn His Gln Leu Cys Ile Gly Glu Ile Phe Gln
        35                  40                  45

Gly Leu Asp Ile Leu Lys Asn Gln Thr Val Arg Gly Gly Thr Val Glu
    50                  55                  60

Met Leu Phe Gln Asn Leu Ser Leu Ile Lys Lys Tyr Ile Asp Arg Gln
65                  70                  75                  80

Lys Glu Lys Cys Gly Glu Glu Arg Arg Arg Thr Arg Gln Phe Leu Asp
                85                  90                  95

Tyr Leu Gln Glu Phe Leu Gly Val Met Ser Thr Glu Trp Ala Met Glu
            100                 105                 110

Gly His His His His His His
        115


<210> SEQ ID NO 4
<211> LENGTH: 119
<212> TYPE: PRT
<213> ORGANISM: Artificial Sequence
<220> FEATURE:
<223> OTHER INFORMATION: Synthetic Sequence_The amino acid sequence for
      rat IL-5 with His-tag

<400> SEQUENCE: 4

Met Glu Ile Pro Met Ser Thr Val Val Lys Glu Thr Leu Ile Gln Leu
1               5                   10                  15

Ser Thr His Arg Ala Leu Leu Thr Ser Asn Glu Thr Met Arg Leu Pro
            20                  25                  30

Val Pro Thr His Lys Asn His Gln Leu Cys Ile Gly Glu Ile Phe Gln
        35                  40                  45

Gly Leu Asp Ile Leu Lys Asn Gln Thr Val Arg Gly Gly Thr Val Glu
    50                  55                  60

Ile Leu Phe Gln Asn Leu Ser Leu Ile Lys Lys Tyr Ile Asp Gly Gln
65                  70                  75                  80

Lys Glu Lys Cys Gly Glu Glu Arg Arg Lys Thr Arg His Phe Leu Asp
```

-continued

```
                85                  90                  95

Tyr Leu Gln Glu Phe Leu Gly Val Met Ser Thr Glu Trp Ala Met Glu
            100                 105                 110

Val His His His His His His
        115


<210> SEQ ID NO 5
<211> LENGTH: 560
<212> TYPE: PRT
<213> ORGANISM: Artificial Sequence
<220> FEATURE:
<223> OTHER INFORMATION: Synthetic Sequence_The amino acid sequence for
      human IL-5 alpha receptor fused to human Fc fragment

<400> SEQUENCE: 5

Asp Leu Leu Pro Asp Glu Lys Ile Ser Leu Leu Pro Pro Val Asn Phe
1               5                   10                  15

Thr Ile Lys Val Thr Gly Leu Ala Gln Val Leu Leu Gln Trp Lys Pro
            20                  25                  30

Asn Pro Asp Gln Glu Gln Arg Asn Val Asn Leu Glu Tyr Gln Val Lys
        35                  40                  45

Ile Asn Ala Pro Lys Glu Asp Asp Tyr Glu Thr Arg Ile Thr Glu Ser
    50                  55                  60

Lys Cys Val Thr Ile Leu His Lys Gly Phe Ser Ala Ser Val Arg Thr
65                  70                  75                  80

Ile Leu Gln Asn Asp His Ser Leu Leu Ala Ser Ser Trp Ala Ser Ala
                85                  90                  95

Glu Leu His Ala Pro Pro Gly Ser Pro Gly Thr Ser Ile Val Asn Leu
            100                 105                 110

Thr Cys Thr Thr Asn Thr Thr Glu Asp Asn Tyr Ser Arg Leu Arg Ser
        115                 120                 125

Tyr Gln Val Ser Leu His Cys Thr Trp Leu Val Gly Thr Asp Ala Pro
    130                 135                 140

Glu Asp Thr Gln Tyr Phe Leu Tyr Tyr Arg Tyr Gly Ser Trp Thr Glu
145                 150                 155                 160

Glu Cys Gln Glu Tyr Ser Lys Asp Thr Leu Gly Arg Asn Ile Ala Cys
                165                 170                 175

Trp Phe Pro Arg Thr Phe Ile Leu Ser Lys Gly Arg Asp Trp Leu Ala
            180                 185                 190

Val Leu Val Asn Gly Ser Ser Lys His Ser Ala Ile Arg Pro Phe Asp
        195                 200                 205

Gln Leu Phe Ala Leu His Ala Ile Asp Gln Ile Asn Pro Pro Leu Asn
    210                 215                 220

Val Thr Ala Glu Ile Glu Gly Thr Arg Leu Ser Ile Gln Trp Glu Lys
225                 230                 235                 240

Pro Val Ser Ala Phe Pro Ile His Cys Phe Asp Tyr Glu Val Lys Ile
                245                 250                 255

His Asn Thr Arg Asn Gly Tyr Leu Gln Ile Glu Lys Leu Met Thr Asn
            260                 265                 270

Ala Phe Ile Ser Ile Ile Asp Asp Leu Ser Lys Tyr Asp Val Gln Val
        275                 280                 285

Arg Ala Ala Val Ser Ser Met Cys Arg Glu Ala Gly Leu Trp Ser Glu
    290                 295                 300

Trp Ser Gln Pro Ile Tyr Val Gly Asn Asp Glu His Lys Pro Leu Arg
305                 310                 315                 320
```

```
Glu Trp Ile Glu Gly Arg Met Asp Glu Pro Lys Ser Cys Asp Lys Thr
                325                 330                 335

His Thr Cys Pro Pro Cys Pro Ala Pro Glu Leu Leu Gly Gly Pro Ser
            340                 345                 350

Val Phe Leu Phe Pro Pro Lys Pro Lys Asp Thr Leu Met Ile Ser Arg
        355                 360                 365

Thr Pro Glu Val Thr Cys Val Val Val Asp Val Ser His Glu Asp Pro
    370                 375                 380

Glu Val Lys Phe Asn Trp Tyr Val Asp Gly Val Glu Val His Asn Ala
385                 390                 395                 400

Lys Thr Lys Pro Arg Glu Glu Gln Tyr Asn Ser Thr Tyr Arg Val Val
                405                 410                 415

Ser Val Leu Thr Val Leu His Gln Asp Trp Leu Asn Gly Lys Glu Tyr
            420                 425                 430

Lys Cys Lys Val Ser Asn Lys Ala Leu Pro Ala Pro Ile Glu Lys Thr
        435                 440                 445

Ile Ser Lys Ala Lys Gly Gln Pro Arg Glu Pro Gln Val Tyr Thr Leu
    450                 455                 460

Pro Pro Ser Arg Asp Glu Leu Thr Lys Asn Gln Val Ser Leu Thr Cys
465                 470                 475                 480

Leu Val Lys Gly Phe Tyr Pro Ser Asp Ile Ala Val Glu Trp Glu Ser
                485                 490                 495

Asn Gly Gln Pro Glu Asn Asn Tyr Lys Thr Thr Pro Pro Val Leu Asp
            500                 505                 510

Ser Asp Gly Ser Phe Phe Leu Tyr Ser Lys Leu Thr Val Asp Lys Ser
        515                 520                 525

Arg Trp Gln Gln Gly Asn Val Phe Ser Cys Ser Val Met His Glu Ala
    530                 535                 540

Leu His Asn His Tyr Thr Gln Lys Ser Leu Ser Leu Ser Pro Gly Lys
545                 550                 555                 560


<210> SEQ ID NO 6
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: The sequence for mAb1705 murine heavy chain
      variable region

<400> SEQUENCE: 6

Glu Val Gln Leu Val Glu Ser Gly Gly Gly Leu Val Gln Pro Gly Arg
1               5                   10                  15

Ser Leu Lys Leu Ser Cys Thr Ala Ser Gly Phe Thr Phe Ser His Tyr
            20                  25                  30

Tyr Met Ala Trp Val Arg Gln Ala Pro Lys Lys Gly Leu Glu Trp Val
        35                  40                  45

Thr Ser Ile Ser Tyr Glu Gly Asp Ile Thr Tyr Tyr Gly Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Ala Ser Gln Thr Leu Arg Glu Ser Phe Asp Tyr Trp Gly Gln Gly Val
            100                 105                 110
```

```
Met Val Thr Val Ser Ser
        115


<210> SEQ ID NO 7
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: The sequence for mAb1705 murine light chain
      variable region

<400> SEQUENCE: 7

Asp Ile Gln Met Thr Gln Ser Pro Ser Ser Met Ser Val Ser Leu Gly
1               5                   10                  15

Asp Arg Val Thr Ile Thr Cys Arg Ala Ser Gln Asp Ile Ala Asn Tyr
            20                  25                  30

Leu Ser Trp Tyr Gln Gln Lys Ile Ala Arg Ser Pro Lys Leu Val Ile
        35                  40                  45

Tyr Gly Thr Ser Asn Leu Glu Val Gly Val Pro Ser Arg Phe Ser Gly
    50                  55                  60

Ser Arg Ser Gly Ser Asp Tyr Ser Leu Thr Ile Asn Thr Leu Glu Ser
65                  70                  75                  80

Glu Asp Thr Gly Ile Tyr Phe Cys Leu Gln Asp Lys Glu Phe Pro Arg
                85                  90                  95

Thr Phe Gly Gly Gly Thr Arg Leu Glu Leu Lys
            100                 105


<210> SEQ ID NO 8
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: mAb1706 murine heavy chain variable region

<400> SEQUENCE: 8

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser His Tyr
            20                  25                  30

Tyr Met Ala Trp Val Arg Gln Ala Pro Lys Lys Gly Leu Glu Trp Val
        35                  40                  45

Thr Ser Ile Asn Tyr Glu Gly Asn Ser Ala Tyr Tyr Gly Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Thr Glu Thr Leu Arg Glu Ser Leu Asp Tyr Trp Gly Gln Gly Val
            100                 105                 110

Met Val Thr Val Ser Ser
        115


<210> SEQ ID NO 9
<211> LENGTH: 107
<212> TYPE: PRT
<213> ORGANISM: Mus musculus
<220> FEATURE:
```

```
<221> NAME/KEY: MISC_FEATURE
<222> LOCATION: (1)..(107)
<223> OTHER INFORMATION: The sequence for mAb1706 murine light chain
      variable region

<400> SEQUENCE: 9

Asp Ile Gln Met Thr Gln Ser Pro Ser Ser Met Ser Val Ser Leu Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Leu Gly Lys Ser Pro Lys Leu Met Ile
        35                  40                  45

His Ser Ala Ser Asn Leu Glu Val Gly Val Pro Ser Arg Phe Ser Gly
    50                  55                  60

Ser Arg Ser Gly Ser Asp Tyr Ser Leu Thr Ile Asn Thr Leu Glu Ser
65                  70                  75                  80

Glu Asp Pro Gly Ile Tyr Phe Cys Leu Gln His Lys Gln Phe Pro Arg
                85                  90                  95

Thr Phe Gly Gly Gly Thr Lys Leu Glu Leu Lys
            100                 105


<210> SEQ ID NO 10
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: The sequence for mAb1780 murine heavy chain
      variable region

<400> SEQUENCE: 10

Gln Val Lys Leu Leu Gln Ser Gly Ala Ala Leu Val Lys Pro Gly Asp
1               5                   10                  15

Ser Val Lys Met Ser Cys Lys Ala Ser Asp Tyr Thr Phe Thr Glu Tyr
            20                  25                  30

Leu Ile His Trp Val Lys Gln Ser Gln Gly Arg Ser Leu Glu Trp Ile
        35                  40                  45

Gly Tyr Ile Asn Pro Tyr Ser Gly Gly Thr Val Tyr Asn Glu Lys Phe
    50                  55                  60

Lys Ser Lys Ala Thr Leu Thr Val Asp Lys Phe Ser Ser Thr Ala Tyr
65                  70                  75                  80

Met Glu Phe Arg Arg Leu Thr Phe Glu Asp Ser Ala Ile Tyr Tyr Cys
                85                  90                  95

Ala Arg Asp Gly Gly Tyr Ser Asp Pro Leu Asp Tyr Trp Gly Gln Gly
            100                 105                 110

Val Met Val Thr Val Ser Ser
        115


<210> SEQ ID NO 11
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: The sequence for mAb1780 murine light chain
      variable region

<400> SEQUENCE: 11

Asp Thr Val Leu Thr Gln Ser Pro Ala Leu Ala Val Ser Pro Gly Glu
```

```
1               5                   10                  15

Arg Val Ser Ile Ser Cys Arg Ala Ser Glu Gly Leu Thr Ser Tyr Met
            20                  25                  30

His Trp Tyr Gln Gln Lys Pro Gly Gln Gln Pro Lys Leu Leu Ile Tyr
        35                  40                  45

Lys Ala Ser Asn Leu Ala Ser Gly Val Pro Ala Arg Phe Ser Gly Ser
    50                  55                  60

Gly Ser Gly Thr Asp Phe Thr Leu Thr Ile Asp Pro Val Glu Ala Asp
65                  70                  75                  80

Asp Ala Ala Thr Tyr Phe Cys Gln Gln Asn Trp Asn Asp Pro Trp Thr
                85                  90                  95

Phe Gly Gly Gly Thr Lys Leu Glu Leu Lys
            100                 105


<210> SEQ ID NO 12
<211> LENGTH: 116
<212> TYPE: PRT
<213> ORGANISM: Mus musculus
<220> FEATURE:
<221> NAME/KEY: MISC_FEATURE
<222> LOCATION: (1)..(116)
<223> OTHER INFORMATION: The sequence for mAb1773 murine heavy chain
      variable region

<400> SEQUENCE: 12

Glu Val Gln Leu Gln Gln Ser Leu Ala Glu Leu Val Arg Pro Gly Ala
1               5                   10                  15

Ser Val Thr Leu Ser Cys Thr Ala Ser Gly Phe Asn Ile Lys Asn Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asp Thr Lys His Gly Pro Lys Phe
    50                  55                  60

Gln Gly Lys Ala Thr Ile Thr Ala Asp Thr Ser Ser Asn Thr Ala Tyr
65                  70                  75                  80

Leu Gln Phe Ser Ser Leu Thr Ser Glu Asp Thr Ala Ile Tyr Tyr Cys
                85                  90                  95

Phe Arg Tyr Gly Ile Tyr Pro Asp His Trp Gly Gln Gly Thr Pro Leu
            100                 105                 110

Thr Val Ser Ser
        115


<210> SEQ ID NO 13
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: The sequence for mAb1773 murine light chain
      variable region

<400> SEQUENCE: 13

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Asn Tyr Ile
            20                  25                  30

Tyr Trp Tyr Gln Gln Lys Pro Arg Ser Ser Pro Lys Pro Trp Ile Tyr
        35                  40                  45
```

-continued

```
Leu Thr Ala Thr Leu Ala Ser Gly Val Pro Ala Arg Phe Ser Gly Ser
    50                  55                  60

Gly Ser Gly Thr Ser Phe Ser Leu Thr Ile Ser Arg Met Glu Ala Glu
65                  70                  75                  80

Asp Ala Ala Thr Tyr Tyr Cys Gln Gln Trp Asn Ser Tyr Pro Tyr Thr
                85                  90                  95

Phe Gly Gly Gly Thr Lys Leu Glu Ile Glu
            100                 105


<210> SEQ ID NO 14
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: The sequence for mAb1779 murine heavy chain
      variable region

<400> SEQUENCE: 14

Gln Val Lys Leu Leu Gln Ser Gly Ala Ala Leu Val Lys Pro Gly Asp
1               5                   10                  15

Ser Val Lys Met Ser Cys Lys Ala Ser Gly Tyr Thr Phe Thr Asp Tyr
            20                  25                  30

Ile Ile His Trp Val Lys Gln Ser His Gly Lys Ser Leu Glu Trp Ile
        35                  40                  45

Gly Tyr Phe Asn Pro Asn Ser Gly Gly Ser Asn Tyr Asn Glu Asn Phe
    50                  55                  60

Lys Arg Lys Ala Thr Leu Thr Ala Asp Lys Ser Ser Ser Thr Ala Tyr
65                  70                  75                  80

Leu Glu Phe Ser Arg Val Thr Ser Glu Asp Ser Ala Ile Tyr Tyr Cys
                85                  90                  95

Gly Arg Arg Ile Ala Trp Asp His Trp Tyr Phe Asp Phe Trp Gly Pro
            100                 105                 110

Gly Thr Met Val Thr Val Ser Ser
        115                 120


<210> SEQ ID NO 15
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: The sequence for mAb1779 murine light chain
      variable region

<400> SEQUENCE: 15

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Gly Ile Ser Asn Asp
            20                  25                  30

Val Ala Trp Tyr Gln Gln Lys Ser Gly Arg Ser Pro Gln Leu Leu Val
        35                  40                  45

Tyr Ala Ala Ser Arg Leu Gln Asp Gly Val Pro Ser Arg Phe Ser Gly
    50                  55                  60

Ser Gly Ser Gly Thr Arg Tyr Phe Phe Lys Ile Ser Gly Met Gln Pro
65                  70                  75                  80

Glu Asp Glu Ala Asp Tyr Phe Cys Gln Gln Gly Tyr Lys Thr Pro Leu
                85                  90                  95
```

```
Thr Phe Gly Ser Gly Thr Lys Leu Glu Ile Lys
            100                 105


<210> SEQ ID NO 16
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: mAb1705 HCDR1

<400> SEQUENCE: 16

His Tyr Tyr Met Ala
1               5


<210> SEQ ID NO 17
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: mAb1705 HCDR2

<400> SEQUENCE: 17

Ser Ile Ser Tyr Glu Gly Asp Ile Thr Tyr Tyr Gly Asp Ser Val Lys
1               5                   10                  15

Gly


<210> SEQ ID NO 18
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: mAb1705 HCDR3

<400> SEQUENCE: 18

Gln Thr Leu Arg Glu Ser Phe Asp Tyr
1               5


<210> SEQ ID NO 19
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: mAb1705 LCDR1

<400> SEQUENCE: 19

Arg Ala Ser Gln Asp Ile Ala Asn Tyr Leu Ser
1               5                   10


<210> SEQ ID NO 20
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: mAb1705 LCDR2

<400> SEQUENCE: 20

Gly Thr Ser Asn Leu Glu Val
```

1 5

<210> SEQ ID NO 21
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: mAb1705 LCDR3

<400> SEQUENCE: 21

Leu Gln Asp Lys Glu Phe Pro Arg Thr
1 5

<210> SEQ ID NO 22
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: mAb1706 HCDR1

<400> SEQUENCE: 22

His Tyr Tyr Met Ala
1 5

<210> SEQ ID NO 23
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: mAb1706 HCDR2

<400> SEQUENCE: 23

Ser Ile Asn Tyr Glu Gly Asn Ser Ala Tyr Tyr Gly Asp Ser Val Lys
1 5 10 15

Gly

<210> SEQ ID NO 24
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: mAb1706 HCDR3

<400> SEQUENCE: 24

Glu Thr Leu Arg Glu Ser Leu Asp Tyr
1 5

<210> SEQ ID NO 25
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: mAb1706 LCDR1

<400> SEQUENCE: 25

Arg Ala Ser Gln Asp Ile Gly Asn Tyr Leu Ser
1 5 10

<210> SEQ ID NO 26
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: mAb1706 LCDR2

<400> SEQUENCE: 26

Ser Ala Ser Asn Leu Glu Val
1               5

<210> SEQ ID NO 27
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: mAb1706 LCDR3

<400> SEQUENCE: 27

Leu Gln His Lys Gln Phe Pro Arg Thr
1               5

<210> SEQ ID NO 28
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: mAb1780 HCDR1

<400> SEQUENCE: 28

Glu Tyr Leu Ile His
1               5

<210> SEQ ID NO 29
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: mAb1780 HCDR2

<400> SEQUENCE: 29

Tyr Ile Asn Pro Tyr Ser Gly Gly Thr Val Tyr Asn Glu Lys Phe Lys
1               5                   10                  15

Ser

<210> SEQ ID NO 30
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: mAb1780 HCDR3

<400> SEQUENCE: 30

Asp Gly Gly Tyr Ser Asp Pro Leu Asp Tyr
1               5                   10

<210> SEQ ID NO 31

-continued

```
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: mAb1780 LCDR1

<400> SEQUENCE: 31

Arg Ala Ser Glu Gly Leu Thr Ser Tyr Met His
1               5                   10


<210> SEQ ID NO 32
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: mAb1780 LCDR2

<400> SEQUENCE: 32

Lys Ala Ser Asn Leu Ala Ser
1               5


<210> SEQ ID NO 33
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: mAb1780 LCDR3

<400> SEQUENCE: 33

Gln Gln Asn Trp Asn Asp Pro Trp Thr
1               5


<210> SEQ ID NO 34
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: mAb1773 HCDR1

<400> SEQUENCE: 34

Asn Thr Tyr Ile His
1               5


<210> SEQ ID NO 35
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: mAb1773 HCDR2

<400> SEQUENCE: 35

Arg Ile Asp Pro Ala Asn Gly Asp Thr Lys His Gly Pro Lys Phe Gln
1               5                   10                  15

Gly


<210> SEQ ID NO 36
<211> LENGTH: 7
<212> TYPE: PRT
```

<213> ORGANISM: Mus musculus
<220> FEATURE:
<221> NAME/KEY: MISC_FEATURE
<222> LOCATION: (1)..(7)
<223> OTHER INFORMATION: mAb1773 HCDR3

<400> SEQUENCE: 36

Tyr Gly Ile Tyr Pro Asp His
1               5

<210> SEQ ID NO 37
<211> LENGTH: 10
<212> TYPE: PRT
<213> ORGANISM: Mus musculus

<400> SEQUENCE: 37

Ser Ala Ser Ser Ser Val Asn Tyr Ile Tyr
1               5                   10

<210> SEQ ID NO 38
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: mAb1773 LCDR2

<400> SEQUENCE: 38

Leu Thr Ala Thr Leu Ala Ser
1               5

<210> SEQ ID NO 39
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: mAb1773 LCDR3

<400> SEQUENCE: 39

Gln Gln Trp Asn Ser Tyr Pro Tyr Thr
1               5

<210> SEQ ID NO 40
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: mAb1779 HCDR1

<400> SEQUENCE: 40

Asp Tyr Ile Ile His
1               5

<210> SEQ ID NO 41
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: mAb1779 HCDR2

<400> SEQUENCE: 41

Tyr Phe Asn Pro Asn Ser Gly Gly Ser Asn Tyr Asn Glu Asn Phe Lys
1               5                   10                  15

Arg

<210> SEQ ID NO 42
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: mAb1779 HCDR3

<400> SEQUENCE: 42

Arg Ile Ala Trp Asp His Trp Tyr Phe Asp Phe
1               5                   10

<210> SEQ ID NO 43
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: mAb1779 LCDR1

<400> SEQUENCE: 43

Leu Ala Ser Glu Gly Ile Ser Asn Asp Val Ala
1               5                   10

<210> SEQ ID NO 44
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: mAb1779 LCDR2

<400> SEQUENCE: 44

Ala Ala Ser Arg Leu Gln Asp
1               5

<210> SEQ ID NO 45
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: mAb1779 LCDR3

<400> SEQUENCE: 45

Gln Gln Gly Tyr Lys Thr Pro Leu Thr
1               5

<210> SEQ ID NO 46
<211> LENGTH: 107
<212> TYPE: PRT
<213> ORGANISM: Artificial Sequence
<220> FEATURE:
<223> OTHER INFORMATION: Synthetic Sequence_h1705_VL.1

<400> SEQUENCE: 46

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ala Asn Tyr

```
            20                  25                  30

Leu Ser Trp Tyr Gln Gln Lys Pro Gly Lys Ala Pro Lys Leu Leu Ile
        35                  40                  45

Tyr Gly Thr Ser Asn Leu Glu Val Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Lys Glu Phe Pro Arg
                85                  90                  95

Thr Phe Gly Gly Gly Thr Lys Val Glu Ile Lys
            100                 105


<210> SEQ ID NO 47
<211> LENGTH: 107
<212> TYPE: PRT
<213> ORGANISM: Artificial Sequence
<220> FEATURE:
<223> OTHER INFORMATION: Synthetic Sequence_h1705_VL.1A

<400> SEQUENCE: 47

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ala Asn Tyr
            20                  25                  30

Leu Ser Trp Tyr Gln Gln Lys Pro Gly Lys Ser Pro Lys Leu Leu Ile
        35                  40                  45

Tyr Gly Thr Ser Asn Leu Glu Val Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Lys Glu Phe Pro Arg
                85                  90                  95

Thr Phe Gly Gly Gly Thr Lys Val Glu Ile Lys
            100                 105


<210> SEQ ID NO 48
<211> LENGTH: 107
<212> TYPE: PRT
<213> ORGANISM: Artificial Sequence
<220> FEATURE:
<223> OTHER INFORMATION: Synthetic Sequence_h1705_VL.1B

<400> SEQUENCE: 48

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ala Asn Tyr
            20                  25                  30

Leu Ser Trp Tyr Gln Gln Lys Pro Gly Lys Ser Pro Lys Leu Val Ile
        35                  40                  45

Tyr Gly Thr Ser Asn Leu Glu Val Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Phe Cys Leu Gln Asp Lys Glu Phe Pro Arg
                85                  90                  95

Thr Phe Gly Gly Gly Thr Lys Val Glu Ile Lys
            100                 105
```

-continued

<210> SEQ ID NO 49
<211> LENGTH: 118
<212> TYPE: PRT
<213> ORGANISM: Artificial Sequence
<220> FEATURE:
<223> OTHER INFORMATION: Synthetic Sequence_h1705_VH.1

<400> SEQUENCE: 49

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45

Ser Ser Ile Ser Tyr Glu Gly Asp Ile Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Thr Leu Arg Glu Ser Phe Asp Tyr Trp Gly Gln Gly Thr
            100                 105                 110

Leu Val Thr Val Ser Ser
        115
```

<210> SEQ ID NO 50
<211> LENGTH: 118
<212> TYPE: PRT
<213> ORGANISM: Artificial Sequence
<220> FEATURE:
<223> OTHER INFORMATION: Synthetic Sequence_h1705_VH.1A

<400> SEQUENCE: 50

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45

Ser Ser Ile Ser Tyr Glu Gly Asp Ile Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gln Thr Leu Arg Glu Ser Phe Asp Tyr Trp Gly Gln Gly Thr
            100                 105                 110

Leu Val Thr Val Ser Ser
        115
```

<210> SEQ ID NO 51
<211> LENGTH: 118
<212> TYPE: PRT
<213> ORGANISM: Artificial Sequence
<220> FEATURE:
<223> OTHER INFORMATION: Synthetic Sequence_h1705_VH.1B

<400> SEQUENCE: 51

```
Glu Val Gln Leu Val Glu Ser Gly Gly Gly Leu Val Gln Pro Gly Gly
```

-continued

```
1               5                   10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45

Thr Ser Ile Ser Tyr Glu Gly Asp Ile Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Ser Gln Thr Leu Arg Glu Ser Phe Asp Tyr Trp Gly Gln Gly Thr
            100                 105                 110

Leu Val Thr Val Ser Ser
        115


<210> SEQ ID NO 52
<211> LENGTH: 330
<212> TYPE: PRT
<213> ORGANISM: Artificial Sequence
<220> FEATURE:
<223> OTHER INFORMATION: Synthetic Sequence_Heavy chain IgG1 constant
      region

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

-continued

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 53
<211> LENGTH: 107
<212> TYPE: PRT
<213> ORGANISM: Artificial Sequence
<220> FEATURE:
<223> OTHER INFORMATION: Synthetic Sequence_Light chain kappa constant
      region

<400> SEQUENCE: 53

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 54
<211> LENGTH: 107
<212> TYPE: PRT
<213> ORGANISM: Artificial Sequence
<220> FEATURE:
<223> OTHER INFORMATION: Synthetic Sequence_h1706_VL.1

<400> SEQUENCE: 54

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Lys Leu Leu Ile
        35                  40                  45

Tyr Ser Ala Ser Asn Leu Glu Val Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Lys Gln Phe Pro Arg
                85                  90                  95

Thr Phe Gly Gly Gly Thr Lys Val Glu Ile Lys
```

100 105

<210> SEQ ID NO 55
<211> LENGTH: 107
<212> TYPE: PRT
<213> ORGANISM: Artificial Sequence
<220> FEATURE:
<223> OTHER INFORMATION: Synthetic Sequence_h1706_VL.1A

<400> SEQUENCE: 55

Asp Ile Gln Met Thr Gln Ser Pro Ser Ser Val Ser Ala Ser Val Gly
1 5 10 15

Asp Arg Val Thr Ile Thr Cys Arg Ala Ser Gln Asp Ile Gly Asn Tyr
20 25 30

Leu Ser Trp Tyr Gln Gln Lys Pro Gly Lys Ser Pro Lys Leu Leu Ile
35 40 45

Tyr Ser Ala Ser Asn Leu Glu Val Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln His Lys Gln Phe Pro Arg
85 90 95

Thr Phe Gly Gly Gly Thr Lys Val Glu Ile Lys
100 105

<210> SEQ ID NO 56
<211> LENGTH: 107
<212> TYPE: PRT
<213> ORGANISM: Artificial Sequence
<220> FEATURE:
<223> OTHER INFORMATION: Synthetic Sequence_h1706_VL.1B

<400> SEQUENCE: 56

Asp Ile Gln Met Thr Gln Ser Pro Ser Ser Val Ser Ala Ser Val Gly
1 5 10 15

Asp Arg Val Thr Ile Thr Cys Arg Ala Ser Gln Asp Ile Gly Asn Tyr
20 25 30

Leu Ser Trp Tyr Gln Gln Lys Pro Gly Lys Ser Pro Lys Leu Met Ile
35 40 45

Tyr Ser Ala Ser Asn Leu Glu Val Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Phe Cys Leu Gln His Lys Gln Phe Pro Arg
85 90 95

Thr Phe Gly Gly Gly Thr Lys Val Glu Ile Lys
100 105

<210> SEQ ID NO 57
<211> LENGTH: 118
<212> TYPE: PRT
<213> ORGANISM: Artificial Sequence
<220> FEATURE:
<223> OTHER INFORMATION: Synthetic Sequence_h1706_VH.1

<400> SEQUENCE: 57

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser His Tyr
20 25 30

-continued

```
Tyr Met Ala Trp Val Arg Gln Ala Pro Gly Lys Gly Leu Glu Trp Val
        35                  40                  45

Ser Ser Ile Asn Tyr Glu Gly Asn Ser Ala Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Thr Leu Arg Glu Ser Leu Asp Tyr Trp Gly Gln Gly Thr
            100                 105                 110

Met Val Thr Val Ser Ser
        115


<210> SEQ ID NO 58
<211> LENGTH: 118
<212> TYPE: PRT
<213> ORGANISM: Artificial Sequence
<220> FEATURE:
<223> OTHER INFORMATION: Synthetic Sequence_h1706_VH.1A

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45

Ser Ser Ile Asn Tyr Glu Gly Asn Ser Ala Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Thr Leu Arg Glu Ser Leu Asp Tyr Trp Gly Gln Gly Thr
            100                 105                 110

Met Val Thr Val Ser Ser
        115


<210> SEQ ID NO 59
<211> LENGTH: 118
<212> TYPE: PRT
<213> ORGANISM: Artificial Sequence
<220> FEATURE:
<223> OTHER INFORMATION: Synthetic Sequence_h1706_VH.1B

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45

Thr Ser Ile Asn Tyr Glu Gly Asn Ser Ala Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
```

```
                85                  90                  95

Ala Thr Glu Thr Leu Arg Glu Ser Leu Asp Tyr Trp Gly Gln Gly Thr
            100                 105                 110

Met Val Thr Val Ser Ser
        115


<210> SEQ ID NO 60
<211> LENGTH: 107
<212> TYPE: PRT
<213> ORGANISM: Artificial Sequence
<220> FEATURE:
<223> OTHER INFORMATION: Synthetic Sequence_h1780_VL.1

<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Gly Leu Thr Ser Tyr
            20                  25                  30

Met His Trp Tyr Gln Gln Lys Pro Gly Gln Ala Pro Arg Leu Leu Ile
        35                  40                  45

Tyr Lys Ala Ser Asn Leu Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asn Trp Asn Asp Pro Trp
                85                  90                  95

Thr Phe Gly Gly Gly Thr Lys Val Glu Ile Lys
            100                 105


<210> SEQ ID NO 61
<211> LENGTH: 107
<212> TYPE: PRT
<213> ORGANISM: Artificial Sequence
<220> FEATURE:
<223> OTHER INFORMATION: Synthetic Sequence_h1780_VL.1A

<400> SEQUENCE: 61

Asp Thr Val Leu Thr Gln Ser Pro Ala Thr Leu Ser Leu Ser Pro Gly
1               5                   10                  15

Glu Arg Ala Thr Leu Ser Cys Arg Ala Ser Glu Gly Leu Thr Ser Tyr
            20                  25                  30

Met His Trp Tyr Gln Gln Lys Pro Gly Gln Ala Pro Arg Leu Leu Ile
        35                  40                  45

Tyr Lys Ala Ser Asn Leu Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asn Trp Asn Asp Pro Trp
                85                  90                  95

Thr Phe Gly Gly Gly Thr Lys Val Glu Ile Lys
            100                 105


<210> SEQ ID NO 62
<211> LENGTH: 107
<212> TYPE: PRT
<213> ORGANISM: Artificial Sequence
<220> FEATURE:
<223> OTHER INFORMATION: Synthetic Sequence_h1780_VL.1B

<400> SEQUENCE: 62
```

```
Asp Thr Val Leu Thr Gln Ser Pro Ala Thr Leu Ser Leu Ser Pro Gly
1               5                   10                  15

Glu Arg Ala Thr Leu Ser Cys Arg Ala Ser Glu Gly Leu Thr Ser Tyr
            20                  25                  30

Met His Trp Tyr Gln Gln Lys Pro Gly Gln Ala Pro Arg Leu Leu Ile
        35                  40                  45

Tyr Lys Ala Ser Asn Leu Ala Ser Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Phe Cys Gln Gln Asn Trp Asn Asp Pro Trp
                85                  90                  95

Thr Phe Gly Gly Gly Thr Lys Val Glu Ile Lys
            100                 105


<210> SEQ ID NO 63
<211> LENGTH: 119
<212> TYPE: PRT
<213> ORGANISM: Artificial Sequence
<220> FEATURE:
<223> OTHER INFORMATION: Synthetic Sequence_h1780_VH.1

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Leu Ile His Trp Val Arg Gln Ala Pro Gly Gln Gly Leu Glu Trp Met
        35                  40                  45

Gly Tyr Ile Asn Pro Tyr Ser Gly Gly Thr Val Tyr Asn Glu Lys Phe
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Gly Tyr Ser Asp Pro Leu Asp Tyr Trp Gly Gln Gly
            100                 105                 110

Thr Met Val Thr Val Ser Ser
        115


<210> SEQ ID NO 64
<211> LENGTH: 119
<212> TYPE: PRT
<213> ORGANISM: Artificial Sequence
<220> FEATURE:
<223> OTHER INFORMATION: Synthetic Sequence_h1780_VH.1A

<400> SEQUENCE: 64

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Leu Ile His Trp Val Arg Gln Ala Pro Gly Gln Gly Leu Glu Trp Met
        35                  40                  45

Gly Tyr Ile Asn Pro Tyr Ser Gly Gly Thr Val Tyr Asn Glu Lys Phe
    50                  55                  60

Lys Ser Arg Val Thr Leu Thr Val Asp Lys Ser Ile Ser Thr Ala Tyr
```

```
65                  70                  75                  80

Met Glu Leu Ser Arg Leu Arg Ser Asp Asp Thr Ala Val Tyr Tyr Cys
                85                  90                  95

Ala Arg Asp Gly Gly Tyr Ser Asp Pro Leu Asp Tyr Trp Gly Gln Gly
            100                 105                 110

Thr Met Val Thr Val Ser Ser
        115


<210> SEQ ID NO 65
<211> LENGTH: 119
<212> TYPE: PRT
<213> ORGANISM: Artificial Sequence
<220> FEATURE:
<223> OTHER INFORMATION: Synthetic Sequence_h1780_VH.1B

<400> SEQUENCE: 65

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Leu Ile His Trp Val Arg Gln Ala Pro Gly Gln Gly Leu Glu Trp Ile
        35                  40                  45

Gly Tyr Ile Asn Pro Tyr Ser Gly Gly Thr Val Tyr Asn Glu Lys Phe
    50                  55                  60

Lys Ser Arg Ala Thr Leu Thr Val Asp Lys Ser Ile Ser Thr Ala Tyr
65                  70                  75                  80

Met Glu Phe Ser Arg Leu Arg Ser Asp Asp Thr Ala Val Tyr Tyr Cys
                85                  90                  95

Ala Arg Asp Gly Gly Tyr Ser Asp Pro Leu Asp Tyr Trp Gly Gln Gly
            100                 105                 110

Thr Met Val Thr Val Ser Ser
        115


<210> SEQ ID NO 66
<211> LENGTH: 119
<212> TYPE: PRT
<213> ORGANISM: Artificial Sequence
<220> FEATURE:
<223> OTHER INFORMATION: Synthetic Sequence_h1780_VH.1C

<400> SEQUENCE: 66

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Leu Ile His Trp Val Lys Gln Ala Pro Gly Gln Gly Leu Glu Trp Ile
        35                  40                  45

Gly Tyr Ile Asn Pro Tyr Ser Gly Gly Thr Val Tyr Asn Glu Lys Phe
    50                  55                  60

Lys Ser Lys Ala Thr Leu Thr Val Asp Lys Ser Ile Ser Thr Ala Tyr
65                  70                  75                  80

Met Glu Phe Ser Arg Leu Arg Ser Asp Asp Thr Ala Val Tyr Tyr Cys
                85                  90                  95

Ala Arg Asp Gly Gly Tyr Ser Asp Pro Leu Asp Tyr Trp Gly Gln Gly
            100                 105                 110

Thr Met Val Thr Val Ser Ser
        115
```

<210> SEQ ID NO 67
<211> LENGTH: 106
<212> TYPE: PRT
<213> ORGANISM: Artificial Sequence
<220> FEATURE:
<223> OTHER INFORMATION: Synthetic Sequence_h1773_VL.1

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Asn Tyr Ile
            20                  25                  30

Tyr Trp Tyr Gln Gln Lys Pro Gly Lys Ala Pro Lys Leu Leu Ile Tyr
        35                  40                  45

Leu Thr Ala Thr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asn Ser Tyr Pro Tyr Thr
                85                  90                  95

Phe Gly Gly Gly Thr Lys Val Glu Ile Lys
            100                 105
```

<210> SEQ ID NO 68
<211> LENGTH: 106
<212> TYPE: PRT
<213> ORGANISM: Artificial Sequence
<220> FEATURE:
<223> OTHER INFORMATION: Synthetic Sequence_h1773_VL.1A

<400> SEQUENCE: 68

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn Tyr Ile
            20                  25                  30

Tyr Trp Tyr Gln Gln Lys Pro Gly Lys Ser Pro Lys Pro Trp Ile Tyr
        35                  40                  45

Leu Thr Ala Thr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asn Ser Tyr Pro Tyr Thr
                85                  90                  95

Phe Gly Gly Gly Thr Lys Val Glu Ile Lys
            100                 105
```

<210> SEQ ID NO 69
<211> LENGTH: 116
<212> TYPE: PRT
<213> ORGANISM: Artificial Sequence
<220> FEATURE:
<223> OTHER INFORMATION: Synthetic Sequence_h1773_VH.1

<400> SEQUENCE: 69

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Thr
            20                  25                  30

Tyr Ile His Trp Val Arg Gln Ala Ser Gly Lys Gly Leu Glu Trp Val
```

```
        35                  40                  45

Gly Arg Ile Asp Pro Ala Val Gly Asp Thr Lys His Gly Pro Lys Phe
    50                  55                  60

Gln Gly Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Thr Arg Tyr Gly Ile Tyr Pro Asp His Trp Gly Gln Gly Thr Leu Val
            100                 105                 110

Thr Val Ser Ser
        115


<210> SEQ ID NO 70
<211> LENGTH: 116
<212> TYPE: PRT
<213> ORGANISM: Artificial Sequence
<220> FEATURE:
<223> OTHER INFORMATION: Synthetic Sequence_h1773_VH.1A

<400> SEQUENCE: 70

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Ile Ser Asn Thr
            20                  25                  30

Tyr Ile His Trp Val Arg Gln Ala Ser Gly Lys Gly Leu Glu Trp Val
        35                  40                  45

Gly Arg Ile Asp Pro Ala Val Gly Asp Thr Lys His Gly Pro Lys Phe
    50                  55                  60

Gln Gly Arg Phe Thr Ile Ser Ala Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Phe Arg Tyr Gly Ile Tyr Pro Asp His Trp Gly Gln Gly Thr Leu Val
            100                 105                 110

Thr Val Ser Ser
        115


<210> SEQ ID NO 71
<211> LENGTH: 116
<212> TYPE: PRT
<213> ORGANISM: Artificial Sequence
<220> FEATURE:
<223> OTHER INFORMATION: Synthetic Sequence_h1773_VH.1B

<400> SEQUENCE: 71

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Ile Ser Asn Thr
            20                  25                  30

Tyr Ile His Trp Val Lys Gln Ala Ser Gly Lys Gly Leu Glu Trp Ile
        35                  40                  45

Gly Arg Ile Asp Pro Ala Val Gly Asp Thr Lys His Gly Pro Lys Phe
    50                  55                  60

Gln Gly Arg Phe Thr Ile Ser Ala Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95
```

```
Phe Arg Tyr Gly Ile Tyr Pro Asp His Trp Gly Gln Gly Thr Leu Val
            100                 105                 110

Thr Val Ser Ser
        115


<210> SEQ ID NO 72
<211> LENGTH: 107
<212> TYPE: PRT
<213> ORGANISM: Artificial Sequence
<220> FEATURE:
<223> OTHER INFORMATION: Synthetic Sequence_h1779_VL.1

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Asn Asp
            20                  25                  30

Val Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Tyr Lys Thr Pro Leu
                85                  90                  95

Thr Phe Gly Gln Gly Thr Lys Leu Glu Ile Lys
            100                 105


<210> SEQ ID NO 73
<211> LENGTH: 107
<212> TYPE: PRT
<213> ORGANISM: Artificial Sequence
<220> FEATURE:
<223> OTHER INFORMATION: Synthetic Sequence_h1779_VL.1A

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Asn Asp
            20                  25                  30

Val Ala Trp Tyr Gln Gln Lys Pro Gly Lys Ser Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Tyr Lys Thr Pro Leu
                85                  90                  95

Thr Phe Gly Gln Gly Thr Lys Leu Glu Ile Lys
            100                 105


<210> SEQ ID NO 74
<211> LENGTH: 107
<212> TYPE: PRT
<213> ORGANISM: Artificial Sequence
<220> FEATURE:
<223> OTHER INFORMATION: Synthetic Sequence_h1779_VL.1B

<400> SEQUENCE: 74

Asp Ile Gln Met Thr Gln Ser Pro Ser Ser Leu Ser Ala Ser Val Gly
```

-continued

```
1               5                   10                  15

Asp Arg Val Thr Ile Thr Cys Leu Ala Ser Glu Gly Ile Ser Asn Asp
            20                  25                  30

Val Ala Trp Tyr Gln Gln Lys Pro Gly Lys Ser Pro Lys Leu Leu Val
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Tyr Lys Thr Pro Leu
                85                  90                  95

Thr Phe Gly Gln Gly Thr Lys Leu Glu Ile Lys
            100                 105


<210> SEQ ID NO 75
<211> LENGTH: 120
<212> TYPE: PRT
<213> ORGANISM: Artificial Sequence
<220> FEATURE:
<223> OTHER INFORMATION: Synthetic Sequence_h1779_VH.1

<400> SEQUENCE: 75

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Ile His Trp Val Arg Gln Ala Pro Gly Gln Gly Leu Glu Trp Met
        35                  40                  45

Gly Tyr Phe Asn Pro Asn Ser Gly Gly Ser Asn Tyr Asn Glu Asn Phe
    50                  55                  60

Lys Arg Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Arg Ile Ala Trp Asp His Trp Tyr Phe Asp Phe Trp Gly Gln
            100                 105                 110

Gly Thr Met Val Thr Val Ser Ser
        115                 120


<210> SEQ ID NO 76
<211> LENGTH: 120
<212> TYPE: PRT
<213> ORGANISM: Artificial Sequence
<220> FEATURE:
<223> OTHER INFORMATION: Synthetic Sequence_h1779_VH.1A

<400> SEQUENCE: 76

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Ile His Trp Val Arg Gln Ala Pro Gly Gln Gly Leu Glu Trp Met
        35                  40                  45

Gly Tyr Phe Asn Pro Asn Ser Gly Gly Ser Asn Tyr Asn Glu Asn Phe
    50                  55                  60

Lys Arg Arg Val Thr Met Thr Ala Asp Lys Ser Ile Ser Thr Ala Tyr
65                  70                  75                  80
```

```
Met Glu Leu Ser Arg Leu Arg Ser Glu Asp Thr Ala Val Tyr Tyr Cys
                85                  90                  95

Ala Arg Arg Ile Ala Trp Asp His Trp Tyr Phe Asp Phe Trp Gly Gln
            100                 105                 110

Gly Thr Met Val Thr Val Ser Ser
        115                 120


<210> SEQ ID NO 77
<211> LENGTH: 120
<212> TYPE: PRT
<213> ORGANISM: Artificial Sequence
<220> FEATURE:
<223> OTHER INFORMATION: Synthetic Sequence_h1779_VH.1B

<400> SEQUENCE: 77

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Ile His Trp Val Arg Gln Ala Pro Gly Gln Gly Leu Glu Trp Ile
        35                  40                  45

Gly Tyr Phe Asn Pro Asn Ser Gly Gly Ser Asn Tyr Asn Glu Asn Phe
    50                  55                  60

Lys Arg Arg Ala Thr Met Thr Ala Asp Lys Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Arg Ile Ala Trp Asp His Trp Tyr Phe Asp Phe Trp Gly Gln
            100                 105                 110

Gly Thr Met Val Thr Val Ser Ser
        115                 120


<210> SEQ ID NO 78
<211> LENGTH: 120
<212> TYPE: PRT
<213> ORGANISM: Artificial Sequence
<220> FEATURE:
<223> OTHER INFORMATION: Synthetic Sequence_h1779_VH.1C

<400> SEQUENCE: 78

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Ile His Trp Val Arg Gln Ala Pro Gly Gln Gly Leu Glu Trp Ile
        35                  40                  45

Gly Tyr Phe Asn Pro Asn Ser Gly Gly Ser Asn Tyr Asn Glu Asn Phe
    50                  55                  60

Lys Arg Arg Ala Thr Met Thr Ala Asp Lys Ser Ile Ser Thr Ala Tyr
65                  70                  75                  80

Leu Glu Phe Ser Arg Leu Arg Ser Glu Asp Thr Ala Val Tyr Tyr Cys
                85                  90                  95

Ala Arg Arg Ile Ala Trp Asp His Trp Tyr Phe Asp Phe Trp Gly Gln
            100                 105                 110

Gly Thr Met Val Thr Val Ser Ser
        115                 120


<210> SEQ ID NO 79
```

<211> LENGTH: 120
<212> TYPE: PRT
<213> ORGANISM: Artificial Sequence
<220> FEATURE:
<223> OTHER INFORMATION: Synthetic Sequence_h1779_VH.1D

<400> SEQUENCE: 79

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Ile His Trp Val Lys Gln Ala Pro Gly Gln Gly Leu Glu Trp Ile
        35                  40                  45

Gly Tyr Phe Asn Pro Asn Ser Gly Gly Ser Asn Tyr Asn Glu Asn Phe
    50                  55                  60

Lys Arg Lys Ala Thr Met Thr Ala Asp Lys Ser Ile Ser Thr Ala Tyr
65                  70                  75                  80

Leu Glu Phe Ser Arg Leu Arg Ser Glu Asp Thr Ala Val Tyr Tyr Cys
                85                  90                  95

Ala Arg Arg Ile Ala Trp Asp His Trp Tyr Phe Asp Phe Trp Gly Gln
            100                 105                 110

Gly Thr Met Val Thr Val Ser Ser
        115                 120
```

<210> SEQ ID NO 80
<211> LENGTH: 443
<212> TYPE: PRT
<213> ORGANISM: Artificial Sequence
<220> FEATURE:
<223> OTHER INFORMATION: Synthetic Sequence_The sequence for hu39D10
      heavy chain

<400> SEQUENCE: 80

```
Glu Val Gln Leu Val Glu Ser Gly Gly Gly Leu Val Gln Pro Gly Gly
1               5                   10                  15

Ser Leu Arg Leu Ser Cys Ala Val Ser Gly Leu Ser Leu Thr Ser Asn
            20                  25                  30

Ser Val Asn Trp Ile Arg Gln Ala Pro Gly Lys Gly Leu Glu Trp Val
        35                  40                  45

Gly Leu Ile Trp Ser Asn Gly Asp Thr Asp Tyr Asn Ser Ala Ile Lys
    50                  55                  60

Ser Arg Phe Thr Ile Ser Arg Asp Thr Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Arg Glu Tyr Tyr Gly Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440
```

<210> SEQ ID NO 81
<211> LENGTH: 214
<212> TYPE: PRT
<213> ORGANISM: Artificial Sequence
<220> FEATURE:
<223> OTHER INFORMATION: Synthetic Sequence_The sequence for hu39D10 light chain

<400> SEQUENCE: 81

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Asn Ser Leu Gln Thr Gly Val Pro Ser Arg Phe Ser Gly
    50                  55                  60

Ser Gly Ser Ala Thr Asp Tyr Thr Leu Thr Ile Ser Ser Leu Gln Pro
65                  70                  75                  80

Glu Asp Phe Ala Thr Tyr Tyr Cys Gln Gln Ser Tyr Lys Phe Pro Asn
                85                  90                  95

Thr Phe Gly Gln Gly Thr Lys Val Glu Val Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 82
<211> LENGTH: 17
<212> TYPE: PRT
<213> ORGANISM: Artificial Sequence
<220> FEATURE:
<223> OTHER INFORMATION: Synthetic Sequence_HCDR2 variant of heavy chain
      of h1773 antibody

<400> SEQUENCE: 82

Arg Ile Asp Pro Ala Val Gly Asp Thr Lys His Gly Pro Lys Phe Gln
1               5                   10                  15

Gly


<210> SEQ ID NO 83
<211> LENGTH: 448
<212> TYPE: PRT
<213> ORGANISM: Artificial Sequence
<220> FEATURE:
<223> OTHER INFORMATION: Synthetic Sequence_h1705-008 heavy chain

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45

Thr Ser Ile Ser Tyr Glu Gly Asp Ile Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Ser Gln Thr Leu Arg Glu Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

-continued

```
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 84
<211> LENGTH: 214
<212> TYPE: PRT
<213> ORGANISM: Artificial Sequence
<220> FEATURE:
<223> OTHER INFORMATION: Synthetic Sequence_h1705-008 light chain

<400> SEQUENCE: 84

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ala Asn Tyr
            20                  25                  30

Leu Ser Trp Tyr Gln Gln Lys Pro Gly Lys Ser Pro Lys Leu Leu Ile
        35                  40                  45

Tyr Gly Thr Ser Asn Leu Glu Val Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Lys Glu Phe Pro Arg
```

-continued

```
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 85
<211> LENGTH: 448
<212> TYPE: PRT
<213> ORGANISM: Artificial Sequence
<220> FEATURE:
<223> OTHER INFORMATION: Synthetic Sequence_h1706-009 heavy chain

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45

Ser Ser Ile Asn Tyr Glu Gly Asn Ser Ala Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Thr Leu Arg Glu Ser Leu Asp Tyr Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
```

```
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 86
<211> LENGTH: 214
<212> TYPE: PRT
<213> ORGANISM: Artificial Sequence
<220> FEATURE:
<223> OTHER INFORMATION: Synthetic Sequence_h1706-009 light chain

<400> SEQUENCE: 86

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ser Pro Lys Leu Met Ile
        35                  40                  45

Tyr Ser Ala Ser Asn Leu Glu Val Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Lys Gln Phe Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

-continued

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 87
<211> LENGTH: 449
<212> TYPE: PRT
<213> ORGANISM: Artificial Sequence
<220> FEATURE:
<223> OTHER INFORMATION: Synthetic Sequence_h1780-017 heavy chain

<400> SEQUENCE: 87

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Leu Ile His Trp Val Arg Gln Ala Pro Gly Gln Gly Leu Glu Trp Ile
        35                  40                  45

Gly Tyr Ile Asn Pro Tyr Ser Gly Gly Thr Val Tyr Asn Glu Lys Phe
    50                  55                  60

Lys Ser Arg Ala Thr Leu Thr Val Asp Lys Ser Ile Ser Thr Ala Tyr
65                  70                  75                  80

Met Glu Phe Ser Arg Leu Arg Ser Asp Asp Thr Ala Val Tyr Tyr Cys
                85                  90                  95

Ala Arg Asp Gly Gly Tyr Ser Asp Pro Leu Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Thr
                245                 250                 255

Arg Glu Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 88
<211> LENGTH: 214
<212> TYPE: PRT
<213> ORGANISM: Artificial Sequence
<220> FEATURE:
<223> OTHER INFORMATION: Synthetic Sequence_h1780-017 light chain

<400> SEQUENCE: 88

Asp Thr Val Leu Thr Gln Ser Pro Ala Thr Leu Ser Leu Ser Pro Gly
1               5                   10                  15

Glu Arg Ala Thr Leu Ser Cys Arg Ala Ser Glu Gly Leu Thr Ser Tyr
            20                  25                  30

Met His Trp Tyr Gln Gln Lys Pro Gly Gln Ala Pro Arg Leu Leu Ile
        35                  40                  45

Tyr Lys Ala Ser Asn Leu Ala Ser Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Phe Cys Gln Gln Asn Trp Asn Asp Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 89
<211> LENGTH: 446
<212> TYPE: PRT
<213> ORGANISM: Artificial Sequence
<220> FEATURE:
<223> OTHER INFORMATION: Synthetic Sequence_h1773-007 heavy chain

<400> SEQUENCE: 89

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Ile Ser Asn Thr
            20                  25                  30

Tyr Ile His Trp Val Lys Gln Ala Ser Gly Lys Gly Leu Glu Trp Ile
        35                  40                  45

Gly Arg Ile Asp Pro Ala Val Gly Asp Thr Lys His Gly Pro Lys Phe
    50                  55                  60

Gln Gly Arg Phe Thr Ile Ser Ala Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Phe Arg Tyr Gly Ile Tyr Pro Asp His Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Tyr Ile Thr Arg Glu Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350
```

-continued

```
Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 90
<211> LENGTH: 213
<212> TYPE: PRT
<213> ORGANISM: Artificial Sequence
<220> FEATURE:
<223> OTHER INFORMATION: Synthetic Sequence_h1773-007 light chain

<400> SEQUENCE: 90

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn Tyr Ile
            20                  25                  30

Tyr Trp Tyr Gln Gln Lys Pro Gly Lys Ser Pro Lys Pro Trp Ile Tyr
        35                  40                  45

Leu Thr Ala Thr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asn Ser Tyr Pro Tyr Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 91
<211> LENGTH: 450
<212> TYPE: PRT
<213> ORGANISM: Artificial Sequence
<220> FEATURE:
<223> OTHER INFORMATION: Synthetic Sequence_h1779-014 heavy chain
```

<400> SEQUENCE: 91

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Ile His Trp Val Lys Gln Ala Pro Gly Gln Gly Leu Glu Trp Ile
        35                  40                  45

Gly Tyr Phe Asn Pro Asn Ser Gly Gly Ser Asn Tyr Asn Glu Asn Phe
    50                  55                  60

Lys Arg Lys Ala Thr Met Thr Ala Asp Lys Ser Ile Ser Thr Ala Tyr
65                  70                  75                  80

Leu Glu Phe Ser Arg Leu Arg Ser Glu Asp Thr Ala Val Tyr Tyr Cys
                85                  90                  95

Ala Arg Arg Ile Ala Trp Asp His Trp Tyr Phe Asp Phe Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

-continued

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 92
<211> LENGTH: 214
<212> TYPE: PRT
<213> ORGANISM: Artificial Sequence
<220> FEATURE:
<223> OTHER INFORMATION: Synthetic Sequence_h1779-014 light chain

<400> SEQUENCE: 92

Asp Ile Gln Met Thr Gln Ser Pro Ser Ser Leu Ser Ala Ser Val Gly
1 5 10 15

Asp Arg Val Thr Ile Thr Cys Leu Ala Ser Glu Gly Ile Ser Asn Asp
20 25 30

Val Ala Trp Tyr Gln Gln Lys Pro Gly Lys Ser Pro Lys Leu Leu Val
35 40 45

Tyr Ala Ala Ser Arg Leu Gln Asp Gly Val Pro Ser Arg Phe Ser Gly
50 55 60

Ser Gly Ser Gly Thr Asp Tyr Thr Phe Thr Ile Ser Ser Leu Gln Pro
65 70 75 80

Glu Asp Ile Ala Thr Tyr Tyr Cys Gln Gln Gly Tyr Lys Thr Pro Leu
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210